United States Patent
Rothbard et al.

(10) Patent No.: US 6,669,951 B2
(45) Date of Patent: *Dec. 30, 2003

(54) COMPOSITIONS AND METHODS FOR ENHANCING DRUG DELIVERY ACROSS AND INTO EPITHELIAL TISSUES

(75) Inventors: Jonathan B. Rothbard, Cupertino, CA (US); Paul A. Wender, Menlo Park, CA (US); P. Leo McGrane, Mountain View, CA (US); Lalitha V. S. Sista, Sunnyvale, CA (US); Thorsten A. Kirschberg, Mountain View, CA (US)

(73) Assignee: CellGate, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/792,480

(22) Filed: Feb. 23, 2001

(65) Prior Publication Data

US 2002/0127198 A1 Sep. 12, 2002

Related U.S. Application Data

(63) Continuation-in-part of application No. 09/648,400, filed on Aug. 24, 2000, now Pat. No. 6,593,292.
(60) Provisional application No. 60/150,510, filed on Aug. 24, 1999.

(51) Int. Cl.$^7$ ............... A61K 9/02; A61K 38/03; A61K 38/08; A61K 38/13; A61K 47/42
(52) U.S. Cl. ............... 424/436; 514/2; 514/11; 514/16; 514/169; 514/634; 514/636; 530/300; 530/329; 564/236; 564/243
(58) Field of Search ............... 424/433, 434, 424/435, 436, 437, 427, 424, 449; 514/2, 11, 12, 13, 14, 15, 16, 17, 169, 634, 635, 636; 530/300, 317, 321, 324, 325, 326, 327, 328, 329, 330; 564/225, 230, 233, 236, 243

(56) References Cited

U.S. PATENT DOCUMENTS

| 4,046,722 A | 9/1977 | Rowland | 530/362 |
| 4,532,207 A | 7/1985 | Brewer et al. | 435/68 |

(List continued on next page.)

FOREIGN PATENT DOCUMENTS

| CA | 2094658 | 10/1993 |
| DE | GB 744 988 | 2/1956 |

(List continued on next page.)

OTHER PUBLICATIONS

Arbuck, et al. "Taxol: Clinical Results and Current Issues in Development"; Chapter 14 in TAXOL©: *Science and Applications*, M. Suffness ed., CRC Press (New York), pp. 379–415 (1995).

(List continued on next page.)

*Primary Examiner*—Jeffrey E. Russel
(74) *Attorney, Agent, or Firm*—Townsend and Townsend and Crew LLP

(57) ABSTRACT

This invention provides compositions and methods for enhancing delivery of drugs and other agents across epithelial tissues, including the skin, gastrointestinal tract, pulmonary epithelium, ocular tissues and the like. The compositions and methods are also useful for delivery across endothelial tissues, including the blood brain barrier. The compositions and methods employ a delivery enhancing transporter that has sufficient guanidino or amidino sidechain moieties to enhance delivery of a compound conjugated to the reagent across one or more layers of the tissue, compared to the non-conjugated compound. The delivery-enhancing polymers include, for example, polyarginine molecules that are preferably between about 6 and 25 residues in length.

88 Claims, 34 Drawing Sheets

U.S. PATENT DOCUMENTS

| | | | | |
|---|---|---|---|---|
| 4,631,190 | A | 12/1986 | Shen et al. | 424/85 |
| 4,701,521 | A | 10/1987 | Ryser et al. | 530/322 |
| 4,847,240 | A | 7/1989 | Ryser et al. | 514/12 |
| 4,880,911 | A | 11/1989 | Brewer et al. | 530/351 |
| 5,028,707 | A | 7/1991 | Nichols et al. | 546/156 |
| 5,162,505 | A | 11/1992 | Dean et al. | 530/391.5 |
| 5,354,844 | A | 10/1994 | Beug et al. | 530/345 |
| 5,362,831 | A | 11/1994 | Mongelli et al. | 526/304 |
| 5,633,230 | A | 5/1997 | Twist et al. | 514/15 |
| 5,646,120 | A | 7/1997 | Sumner-Smith et al. | 514/14 |
| 5,674,849 | A | 10/1997 | Twist et al. | 514/15 |
| 5,716,614 | A | 2/1998 | Katz et al. | 424/94.3 |
| 5,783,178 | A | 7/1998 | Kabanov et al. | 424/78.31 |
| 5,789,531 | A | 8/1998 | Sumner-Smith et al. | 530/328 |
| 5,795,909 | A | 8/1998 | Shashoua | 514/449 |
| 5,804,604 | A | 9/1998 | Frankel et al. | 530/324 |
| 5,831,001 | A | 11/1998 | Twist et al. | 530/328 |
| 5,977,163 | A | 11/1999 | Li et al. | 514/449 |
| 6,077,835 | A | 6/2000 | Hanson et al. | 514/44 |
| 6,089,234 | A | 7/2000 | Bretton | 128/898 |
| 6,306,993 | B1 * | 10/2001 | Rothbard et al. | 526/304 |

FOREIGN PATENT DOCUMENTS

| | | |
|---|---|---|
| EP | 0009498 | 4/1980 |
| EP | 0 599 303 | 6/1994 |
| JP | 10 095738 | 4/1998 |
| WO | WO 79/00515 | 8/1979 |
| WO | WO 91/09958 | 7/1991 |
| WO | WO 92/07871 | 5/1992 |
| WO | WO 93/04701 | 3/1993 |
| WO | WO 93/21941 | 11/1993 |
| WO | WO 94/04686 | 3/1994 |
| WO | WO 94/14464 | 7/1994 |
| WO | WO 95/11038 | 4/1995 |
| WO | WO 96/21036 | 7/1996 |
| WO | WO 97/33552 | 9/1997 |
| WO | WO 97/40854 | 11/1997 |
| WO | WO 98/52614 | 11/1998 |
| WO | WO 01/13957 | 3/2001 |
| WO | WO 02/07773 | 1/2002 |

OTHER PUBLICATIONS

Balicki, et al. "Histone H2A Significantly Enhances In Vitro DNA Transfection"; *Molecular Medicine* vol. 3, No. 11 pp. 782–787 (1997).

Boussif, et al. "A versatile vector for gene and oligonucleotide transfer into cells in culture and in vivo: Polyethylenimine"; *Proc. Natl. Acad. Sci. USA* vol. 92, pp. 7297–7301 (Aug. 1995).

Burton, et al. "Basic polyelectrolytes and protein transport across the new–born pig intestine"; *Physiological Society* pp. 27P–28P (Dec. 1970), vol. 211, No. 2.

Brugidou, et al., "The Retro–Inverso Form of a Homeobox–Derived Short Peptide is Rapidly Internalised by Cultured Neurones: A New Basis For An Efficient Intracellular Delivery System"; *Biochemical and Biophysical Research Communications* vol. 214, No. 2 pp. 685–693 (Sep. 1995).

Buschle, et al. "Transloading of tumor antigen–derived peptides into antigen–presenting cells"; *PNAS* vol. 94, pp. 3256–3261 (Apr. 1997).

Chen, et al. "Galactosylated Histone–Mediated Gene Transfer and Expression"; *Human Gene Therapy* vol. 5, pp. 429–435 (1994).

Cooke, et al. "Nitric Oxide Synthase: Role in the Genesis of Vascular Disease"; *Annu. Rev. Med.* vol. 48, pp. 489–509 (1997).

Dattilo, et al. "Inducible Nitric Oxide Synthase Expression in Human Vein Grafts"; *Am J Surg.* vol. 174, pp. 177–180 (1997).

de Bont, et al. "Synthesis and Biological Activity of β–Glucuronyl Carbamate–Based Prodrugs of Paclitaxel as Potential Candidates for ADEPT"; *Biorganic & Medicinal Chemistry* vol. 5, No. 2 pp. 405–414 (1997).

Derossi, et al. "The Third Helix of the Antennapedia Homeodomain Translocates through Biological Membranes"; *The Journal of Biological Chemistry* vol. 269, No. 14 pp. 10444–10450 (1994).

Elferink, "Changes of Plasma Membrane Permeability in Neutrophils Treated With Polycations"; *Inflammation* vol. 15, No. 2 pp. 103–115 (Apr. 1991).

Emi, et al. "Gene Transfer Mediated by Polyarginine Requires a Formation of Big Carrier–Complex of DNA Aggregate"; *Biochemical and Biophysical Research Communications* vol. 231, pp. 421–424 (1997).

Fawell, et al. "Tat–mediated delivery of heterologous proteins into cells"; *Proc. Natl. Acad. Sci. USA* vol. 91, pp. 664–668 (Jan.. 1994).

Fletcher, et al. "Partially Modified Retro–Inverso Peptides: Development, Synthesis, and Conformational Behavior"; *Chem. Rev.* vol. 96 pp. 763–795 (1998).

Garg, et al. "Nitric Oxide–generating Vasodilators and 8–Bromo–Cyclic Guanosine Monophosphate Inhibit Mitogenesis and Proliferation of Cultured Rat Vascular Smooth Muscle Cells"; *J. Clin. Invest.* vol. 83, pp. 1774–1777 (May 1989).

Georg, et al. "The Medicinal Chemistry of Taxol"; Chapter 13 in TAXOL© *Science and Applications*, M. Suffness ed., CRC Press (New York), pp. 317–375 (1995).

Golik et al. "Synthesis and Antitumor Evaluation of Paclitaxel Phosphonooxymethyl Ethers: A Novel Class of Water Soluble Paclitaaxel Pro–Drugs" *Bioorganic & Medicinal Chemistry Letters* vol. 6, No. 15 pp. 1837–1842 (1996).

Greenwald, et al. "Drug Delivery Systems: Water Soluble Taxol 2'–Poly(ethylene glycol) Ester Prodrugs–Design and in Vivo Effectiveness"; *J. Med. Chem.* 39(2):424–431 (Jan. 1996).

Kessler "Peptoids—A New Approach to the Development of Pharmaceuticals"; *Angew Chem. Int. Ed. Engl.* vol. 32, No. 4 p. 543–544 (1993).

Kingston "Natural Toxoids: Structure and Chemistry"; Chapter 12 in TAXOL©: *Science & Applications*, M. Suffness ed, CRC Press (New York), pp. 287–315 (1995).

Lam, et al. "The "One–Bead–One–Compound" Combinatorial Library Method"; *Chem. Rev.* vol. 97, pp. 411–448 (1997).

Lloyd–Jones, M.D., et al. "The Vascular Biology of Nitric Oxide and Its Role in Atherogenesis"; *Annu. Rev. Med.* vol. 47, pp. 365–375 (1996).

Mauersberger, et al. "Untersuchungen zur Zytotoxizität von Poly–L–Arginin, Poly–L–Lysin and DEAE–Dextran bei L–Zellen und Mäuseembryofibroblasten"; *Exp. Path* vol. 18 pp. 268–274 (1977).

Murphy, et al. "A combinatorial approach to the discovery of efficient cationic peptiod reagents for gene delivery"; *Proc. Natl. Acad. Sci. USA* vol. 95, pp. 1517–1522 (Feb. 1998).

Natsume, et al. "Screening of Absorption Enhancers for Nasal Peptide and Protein Delivery"; *Proceed. Intern. Symp. Conrol. Rel. Bioact. Mater.* vol. 23, pp. 481–482 (Jul. 1996).

Nicolaou, et al. "Design, synthesis and biological activity of protaxols"; *Nature* vol. 364, pp. 464–466 (Jul. 1993).

Rodrigues, et al. "Synthesis and β–lactamase–mediated activation of a cephalosporin–taxol prodrug" *Chemistry and Biology* vol. 2, pp. 223–227 (Apr. 1995).

Rose, "Preclinical Antitumor Activity or Taxanes"; Chapter 8 in TAXOL©: *Science & Applications*, M. Suffness ed., CRC Press (New York), pp. 209–235 (1995).

Simon, et al. "Peptoids: A modular approach to drug discovery"; *Proc. Natl. Acad. Sci. USA* vol. 89 p. 9367–9371 (Oct. 1992).

Straubinger "Biopharmaceutics of Paclitaxel (Taxol): Formulation, Activity, and Pharmacokinetics"; Chapter 9 in TAXOL© *Science and Applications*, M. Suffness ed., CRC Press (New York), p. 237–258 (1995).

Sumner–Smith, et al. "123: 79357m Antiherpetic activities of N–α–acetyl–nona–D–=arginine amide acetate"; *6001 Chemical Abstracts* vol. 123, No. 7 pp. 606 (1995).

Thompson, et al. "Synthesis and Applications of Small Molecule Libraries"; *Chem. Rev.* 96:555–600 (1996).

Tsao, et al. "Nitric Oxide Regulates Monocyte Chemotactic Protein–1"; *Circulation* 96;, 934–940 (1997).

Uchida, et al. "Polycations Decrease the Transepithelial Resistance of Cultured Tracheal Epithelial Cells"; *Chest* vol. 101, No. 3, p. 33S (Mar. 1992).

Ueda, et al. "Synthesis and Antitumor Evaluation of 2'–Oxycarbonylpaclitaxels (Paclitaxel–2'–Carbonates)"; *Bioorganic & Medicinal Chemistry Letters* vol. 4 No. 15 pp. 1861–1864 (Aug.1994).

Ueda, et al. "Novel Water Soluble Phosphate Prodrugs of Taxol© Possesing In Vivo Antitumor Activity"; *Boorganic & Medicinal Chemistry Letters* vol. 3, No. 8:1761–1766 (May 1993).

Vyas, et al. "Synthesis and Antitumor Evaluation of Water Soluble Taxol Phosphates"; *Bioorganic & Medicinal Chemistry Letters* vol. 3, No. 6 pp. 1357–1360 (1993).

Vyas, et al. "Phosphatase–Activated Prodrugs of Paclitaxel"; Chapter 9 in *Taxane Anticancer Agents* American Chemical Society p. 124 (1995).

Wolf, et al. "Dietary L–Arginine Supplementation Normalizes Platelet Aggregation in Hypercholesterolemic Humans"; *JACC* vol. 29, No. 3 pp. 479–485 (Mar. 1997).

Zuckermann, et al. "Efficient Method for the Preparation of Peptoids [Oligo(N–substituted glycines)] by Submonomer Solid–Phase Synthesis"; *Chemtracts—Macromolecular Chemistry* vol. 4 pp. 80–83 (1993).

Aoyagi, et al. "Polymerization of Benzalkonium Chloride–Type Monomer and Application to Percutaneous Drug Absorption Enhancer"; *Journal of Controlled Release*, vol. 13, No. 1 pp. 63–71 (Jul. 1990).

Babiuk, et al., "Cutaneous vaccination: the skin as an immunologically active tissue and the challenge of antigen delivery"; *Journal of Controlled Release* vol. 66 pp. 199–214 (2000).

Colin, et al. "Liposomes enhance delivery and expression of an RGD–oligolysine gene transfer vector in human tracheal cells"; *Gene Therapy* vol. 5 pp. 1488–1498 (1998).

Coyle, e tal. "Role of Cationic Proteins in the Airway Hyperresponsiveness Due to Airway Inflammation"; *Am. Respir. Crit. Care Med.* vol. 150 pp. 563–571 (1994).

Gama, et al. "$Ca^{2+}$ –sensing receptors in intestinal epithelium"; *American Journal of Physiology* vol. 273, No. 4, Part 1 pp. C1168–C1175 (Oct. 1997).

Hosoya, et al. "Effect of Several Hydrophilic Polymers on the Permeation of Morphine and Salicylic Acid through Excised Hairless Rat Skin"; *Chem. Pharm. Bull.* 46(5) 882–885 (1998).

Hulsmann, "Permeability of Human Isolated Airways Increases after Hydrogen Peroxide and Poly–L–arginine"; *Am. J. Respir. Crit. Care Med.* vol. 153 pp. 841–846 (1996).

Koji Kobayashi, "Composition for Transmucosally Absorbable Preparation"; Patent Abstracts of Japan, Publication No. 10095738, Publication Date Apr. 4, 1998.

Perr, et al. "Protamine Selectively Inhibits Collagen Synthesis by Human Intestinal Smooth Muscle Cells and Other Mesenchymal Cells"; *Journal of Cellular Physiology* 140:463–470 (1989).

Peterson, et al. "Polyamino Acid Enhancement of Bacterial Phagocytosis by Human Polymorphonuclear Leukocytes and Peritoneal Macrophages"; *Infection and Immunity* vol. 43, No. 2, pp. 561–566 (Feb. 1984).

Santana, et al., "Inflammatory responses induced by poly–L–arginine in rat lungs in vivo"; *Agents Actions* vol. 39, No. 3–4 pp. 104–110 (1993).

Tzan, et al. "Mammalian urinary bladder permeability is altered by cationic proteins modulation by divalent cations"; *American Journal of Physiology* vol. 267, No. 4, Part 1, pp. C1013–C1026 (1994).

Tzan, et al., "Modification of Epithelial Permeability by Cationic Polypeptides"; *American Journal of Physiology* vol. 265, No. 6, Part 1, pp. C1637–C1647 (1993).

Uchida, et. al., Cationic Proteins Increase the Permeability of Cultured Rabbit Tracheal Eptihelial Cells: Modification by Heparin and Extracellular Calcium: *Experimental Lung Research* vol. 22, No. 1, pp. 85–99 (1996).

Wei, et al. "synthesis of Oligoarginine–Oligonucleotide Conjugates and Oligoarginine–Bridge Oligonucleotide Pairs"; *Bioconjugate Chem.* vol. 5, pp. 468–474 (Sep./Oct. 1994).

* cited by examiner n = 5, 7, 9, 0 (control)

I

II

III

IV

A.

B.

n = 5 and 7 n = 1, 2
R = H, Ac

Synthetic Schemes for FK 506 Conjugates

Synthetic Schemes for FK 506 Conjugates (contd.)

SEQUENCE LISTING

```
<160> NUMBER OF SEQ ID NOS: 57

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence:Arg
      homopolymer R5, Arg oligomer

<400> SEQUENCE: 1

Arg Arg Arg Arg Arg
  1               5

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence:Arg
      homopolymer R6, Arg oligomer

<400> SEQUENCE: 2

Arg Arg Arg Arg Arg Arg
  1               5

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence:Arg
      homopolymer R7, heptamer of L-Arg, hepta-L-Arg, Arg oligomer

<400> SEQUENCE: 3

Arg Arg Arg Arg Arg Arg Arg
```

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence:Arg
      homopolymer R8, Arg oligomer

<400> SEQUENCE: 4

Arg Arg Arg Arg Arg Arg Arg Arg
 1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence:Arg
      homopolymer R9, Arg oligomer

<400> SEQUENCE: 5

Arg Arg Arg Arg Arg Arg Arg Arg Arg
 1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence:heptamer of
      L-Arg chemical after pH dependent chemical release
<221> NAME/KEY: MOD_RES
<222> LOCATION: (1)
<223> OTHER INFORMATION: Xaa =
      2-[4-benzyl-2,5-diketopiperazinyl]-acetyl-Arg

<400> SEQUENCE: 6

Xaa Arg Arg Arg Arg Arg Arg
 1               5

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence:unlabeled
      peptide
<221> NAME/KEY: MOD_RES
<222> LOCATION: (10)
<223> OTHER INFORMATION: Xaa = cysteinamine

<400> SEQUENCE: 7

Arg Arg Arg Arg Arg Arg Arg Gly Gly Xaa
 1               5                  10

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence:analog of
      HIV-1 tat protein basic region Tat-49-57
<221> NAME/KEY: MOD_RES
<222> LOCATION: (1)
<223> OTHER INFORMATION: Xaa = fluorescein linked to amino group of
      aminohexanoic acid (Fl-ahx) attached to the
      N-terminal amino group of Arg

```
<400> SEQUENCE: 8

Xaa Lys Lys Arg Arg Gln Arg Arg Arg
 1               5

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence:Tat-49-56
      truncated analog of HIV-1 tat protein basic region
      Tat-49-57
<221> NAME/KEY: MOD_RES
<222> LOCATION: (1)
<223> OTHER INFORMATION: Xaa = fluorescein linked to amino group of
      aminohexanoic acid (Fl-ahx) attached to the
      N-terminal amino group of Arg

<400> SEQUENCE: 9

Xaa Lys Lys Arg Arg Gln Arg Arg
 1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence:Tat-49-55
      truncated analog of HIV-1 tat protein basic region
      Tat-49-57
<221> NAME/KEY: MOD_RES
<222> LOCATION: (1)
<223> OTHER INFORMATION: Xaa = fluorescein linked to amino group of
      aminohexanoic acid (Fl-ahx) attached to the
      N-terminal amino group of Arg

<400> SEQUENCE: 10

Xaa Lys Lys Arg Arg Gln Arg
 1               5

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence:Tat-50-57
      truncated analog of HIV-1 tat protein basic region
      Tat-49-57
<221> NAME/KEY: MOD_RES
<222> LOCATION: (1)
<223> OTHER INFORMATION: Xaa = fluorescein linked to amino group of
      aminohexanoic acid (Fl-ahx) attached to the
      N-terminal amino group of Lys

<400> SEQUENCE: 11

Xaa Lys Arg Arg Gln Arg Arg Arg
 1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence:Tat-51-57
      truncated analog of HIV-1 tat protein basic region
      Tat-49-57
<221> NAME/KEY: MOD_RES
<222> LOCATION: (1)
<223> OTHER INFORMATION: Xaa = fluorescein linked to amino group of
      aminohexanoic acid (Fl-ahx) attached to the
      N-terminal amino group of Lys
```

```
<400> SEQUENCE: 12

Xaa Arg Arg Gln Arg Arg Arg
 1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence:A-49
      Ala-substituted analog of HIV-1 tat protein basic
      region Tat-49-57
<221> NAME/KEY: MOD_RES
<222> LOCATION: (1)
<223> OTHER INFORMATION: Xaa = fluorescein linked to amino group of
      aminohexanoic acid (Fl-ahx) attached to the
      N-terminal amino group of Ala

<400> SEQUENCE: 13

Xaa Lys Lys Arg Arg Gln Arg Arg Arg
 1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence:A-50
      Ala-substituted analog of HIV-1 tat protein basic
      region Tat-49-57
<221> NAME/KEY: MOD_RES
<222> LOCATION: (1)
<223> OTHER INFORMATION: Xaa = fluorescein linked to amino group of
      aminohexanoic acid (Fl-ahx) attached to the
      N-terminal amino group of Arg

<400> SEQUENCE: 14

Xaa Ala Lys Arg Arg Gln Arg Arg Arg
 1               5

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence:A-51
      Ala-substituted analog of HIV-1 tat protein basic
      region Tat-49-57
<221> NAME/KEY: MOD_RES
<222> LOCATION: (1)
<223> OTHER INFORMATION: Xaa = fluorescein linked to amino group of
      aminohexanoic acid (Fl-ahx) attached to the
      N-terminal amino group of Arg

<400> SEQUENCE: 15

Xaa Lys Ala Arg Arg Gln Arg Arg Arg
 1               5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence:A-52
      Ala-substituted analog of HIV-1 tat protein basic
      region Tat-49-57
<221> NAME/KEY: MOD_RES
<222> LOCATION: (1)
<223> OTHER INFORMATION: Xaa = fluorescein linked to amino group of
      aminohexanoic acid (Fl-ahx) attached to the
```

```
                N-terminal amino group of Arg

<400> SEQUENCE: 16

Xaa Lys Lys Ala Arg Gln Arg Arg Arg
 1               5

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence:A-53
      Ala-substituted analog of HIV-1 tat protein basic
      region Tat-49-57
<221> NAME/KEY: MOD_RES
<222> LOCATION: (1)
<223> OTHER INFORMATION: Xaa = fluorescein linked to amino group of
      aminohexanoic acid (Fl-ahx) attached to the
      N-terminal amino group of Arg

<400> SEQUENCE: 17

Xaa Lys Lys Arg Ala Gln Arg Arg Arg
 1               5

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence:A-54
      Ala-substituted analog of HIV-1 tat protein basic
      region Tat-49-57
<221> NAME/KEY: MOD_RES
<222> LOCATION: (1)
<223> OTHER INFORMATION: Xaa = fluorescein linked to amino group of
      aminohexanoic acid (Fl-ahx) attached to the
      N-terminal amino group of Arg

<400> SEQUENCE: 18

Xaa Lys Lys Arg Arg Ala Arg Arg Arg
 1               5

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence:A-55
      Ala-substituted analog of HIV-1 tat protein basic
      region Tat-49-57
<221> NAME/KEY: MOD_RES
<222> LOCATION: (1)
<223> OTHER INFORMATION: Xaa = fluorescein linked to amino group of
      aminohexanoic acid (Fl-ahx) attached to the
      N-terminal amino group of Arg

<400> SEQUENCE: 19

Xaa Lys Lys Arg Arg Gln Ala Arg Arg
 1               5

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence:A-56
      Ala-substituted analog of HIV-1 tat protein basic
      region Tat-49-57
<221> NAME/KEY: MOD_RES
<222> LOCATION: (1)
<223> OTHER INFORMATION: Xaa = fluorescein linked to amino group of
```

```
        aminohexanoic acid (Fl-ahx) attached to the
        N-terminal amino group of Arg

<400> SEQUENCE: 20

Xaa Lys Lys Arg Arg Gln Arg Ala Arg
 1               5

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence:A-57
        Ala-substituted analog of HIV-1 tat protein basic
        region Tat-49-57
<221> NAME/KEY: MOD_RES
<222> LOCATION: (1)
<223> OTHER INFORMATION: Xaa = fluorescein linked to amino group of
        aminohexanoic acid (Fl-ahx) attached to the
        N-terminal amino group of Arg

<400> SEQUENCE: 21

Xaa Lys Lys Arg Arg Gln Arg Arg Ala
 1               5

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence:Tat-57-49
        retro-isomer of HIV-1 tat protein basic region
        Tat-49-57
<221> NAME/KEY: MOD_RES
<222> LOCATION: (1)
<223> OTHER INFORMATION: Xaa = fluorescein linked to amino group of
        aminohexanoic acid (Fl-ahx) attached to the
        N-terminal amino group of Arg

<400> SEQUENCE: 22

Xaa Arg Arg Gln Arg Arg Lys Lys Arg
 1               5

<210> SEQ ID NO 23
<211> LENGTH: 5
<212> TYPE: PRT
<213> ORGANISM: Artificial Sequence
<220> FEATURE:
<223> OTHER INFORMATION: Description of Artificial Sequence:Arg oligomer
        R5, Arg homopolymer
<221> NAME/KEY: MOD_RES
<222> LOCATION: (1)
<223> OTHER INFORMATION: Xaa = fluorescein linked to amino group of
        aminohexanoic acid (Fl-ahx) attached to the
        N-terminal amino group of Arg

<400> SEQUENCE: 23

Xaa Arg Arg Arg Arg
 1               5

<210> SEQ ID NO 24
<211> LENGTH: 6
<212> TYPE: PRT
<213> ORGANISM: Artificial Sequence
<220> FEATURE:
<223> OTHER INFORMATION: Description of Artificial Sequence:Arg oligomer
        R6, Arg homopolymer
<221> NAME/KEY: MOD_RES
<222> LOCATION: (1)
<223> OTHER INFORMATION: Xaa = fluorescein linked to amino group of
        aminohexanoic acid (Fl-ahx) attached to the
```

-continued

```
      N-terminal amino group of Arg

<400> SEQUENCE: 24

Xaa Arg Arg Arg Arg Arg
  1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence:Arg oligomer
      R7, Arg homopolymer
<221> NAME/KEY: MOD_RES
<222> LOCATION: (1)
<223> OTHER INFORMATION: Xaa = fluorescein linked to amino group of
      aminohexanoic acid (Fl-ahx) attached to the
      N-terminal amino group of Arg

<400> SEQUENCE: 25

Xaa Arg Arg Arg Arg Arg Arg
  1               5

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence:Arg oligomer
      R8, Arg homopolymer
<221> NAME/KEY: MOD_RES
<222> LOCATION: (1)
<223> OTHER INFORMATION: Xaa = fluorescein linked to amino group of
      aminohexanoic acid (Fl-ahx) attached to the
      N-terminal amino group of Arg

<400> SEQUENCE: 26

Xaa Arg Arg Arg Arg Arg Arg Arg
  1               5

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence:Arg oligomer
      R9, Arg homopolymer
<221> NAME/KEY: MOD_RES
<222> LOCATION: (1)
<223> OTHER INFORMATION: Xaa = fluorescein linked to amino group of
      aminohexanoic acid (Fl-ahx) attached to the
      N-terminal amino group of Arg

<400> SEQUENCE: 27

Xaa Arg Arg Arg Arg Arg Arg Arg Arg
  1               5

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence:HIV-1 tat
      protein basic region Tat-49-57

<400> SEQUENCE: 28

Arg Lys Lys Arg Arg Gln Arg Arg Arg
  1               5
```

```
<210> SEQ ID NO 29
<211> LENGTH: 16
<212> TYPE: PRT
<213> ORGANISM: Artificial Sequence
<220> FEATURE:
<223> OTHER INFORMATION: Description of Artificial Sequence:Antennapedia
      homeodomain, Antennapedia-43-58

<400> SEQUENCE: 29

Arg Gln Ile Lys Ile Trp Phe Gln Asn Arg Arg Met Lys Trp Lys Lys
  1               5                  10                  15

<210> SEQ ID NO 30
<211> LENGTH: 16
<212> TYPE: PRT
<213> ORGANISM: Artificial Sequence
<220> FEATURE:
<223> OTHER INFORMATION: Description of Artificial Sequence:Antennapedia
      homeodomain, Antennapedia-43-58
<221> NAME/KEY: MOD_RES
<222> LOCATION: (1)
<223> OTHER INFORMATION: Xaa = fluorescein linked to amino group of
      aminohexanoic acid (Fl-ahx) attached to the
      N-terminal amino group of Arg

<400> SEQUENCE: 30

Xaa Gln Ile Lys Ile Trp Phe Gln Asn Arg Arg Met Lys Trp Lys Lys
  1               5                  10                  15

<210> SEQ ID NO 31
<211> LENGTH: 7
<212> TYPE: PRT
<213> ORGANISM: Artificial Sequence
<220> FEATURE:
<223> OTHER INFORMATION: Description of Artificial
      Sequence:peptide-aminocaproic acid-DTPA complex
<221> NAME/KEY: MOD_RES
<222> LOCATION: (1)
<223> OTHER INFORMATION: Xaa = diethylenetriaminepentaacetic acid
      attached to Arg using aminocaproic acid spacer

<400> SEQUENCE: 31

Xaa Arg Arg Arg Arg Arg Arg
  1               5

<210> SEQ ID NO 32
<211> LENGTH: 7
<212> TYPE: PRT
<213> ORGANISM: Artificial Sequence
<220> FEATURE:
<223> OTHER INFORMATION: Description of Artificial
      Sequence:NH-2R-7CCONH-2.8TFA transporter conjugate
<221> NAME/KEY: MOD_RES
<222> LOCATION: (7)
<223> OTHER INFORMATION: Xaa = Arg modified by -CCONH-2.8trifluoroacetic
      acid (TFA)

<400> SEQUENCE: 32

Arg Arg Arg Arg Arg Arg Xaa
  1               5

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence:amino acid
      oligomer delivery enhancing transport moiety
<221> NAME/KEY: MOD_RES
<222> LOCATION: (2)
<223> OTHER INFORMATION: Xaa = Gly, beta-alanine, gamma-amino butyric
```

```
      acid or eta-amino caproic acid
<221> NAME/KEY: MOD_RES
<222> LOCATION: (5)
<223> OTHER INFORMATION: Xaa = Gly, beta-alanine, gamma-amino butyric
      acid or eta-amino caproic acid

<400> SEQUENCE: 33

Arg Xaa Arg Arg Xaa Arg Arg
  1               5

<210> SEQ ID NO 34
<211> LENGTH: 10
<212> TYPE: PRT
<213> ORGANISM: Artificial Sequence
<220> FEATURE:
<223> OTHER INFORMATION: Description of Artificial Sequence:amino acid
      oligomer delivery enhancing transport moiety
<221> NAME/KEY: MOD_RES
<222> LOCATION: (2)
<223> OTHER INFORMATION: Xaa = Gly, beta-alanine, gamma-amino butyric
      acid or eta-amino caproic acid
<221> NAME/KEY: MOD_RES
<222> LOCATION: (5)
<223> OTHER INFORMATION: Xaa = Gly, beta-alanine, gamma-amino butyric
      acid or eta-amino caproic acid
<221> NAME/KEY: MOD_RES
<222> LOCATION: (8)
<223> OTHER INFORMATION: Xaa = Gly, beta-alanine, gamma-amino butyric
      acid or eta-amino caproic acid

<400> SEQUENCE: 34

Arg Xaa Arg Arg Xaa Arg Arg Xaa Arg Arg
  1               5                  10

<210> SEQ ID NO 35
<211> LENGTH: 13
<212> TYPE: PRT
<213> ORGANISM: Artificial Sequence
<220> FEATURE:
<223> OTHER INFORMATION: Description of Artificial Sequence:amino acid
      oligomer delivery enhancing transport moiety
<221> NAME/KEY: MOD_RES
<222> LOCATION: (2)
<223> OTHER INFORMATION: Xaa = Gly, beta-alanine, gamma-amino butyric
      acid or eta-amino caproic acid
<221> NAME/KEY: MOD_RES
<222> LOCATION: (5)
<223> OTHER INFORMATION: Xaa = Gly, beta-alanine, gamma-amino butyric
      acid or eta-amino caproic acid
<221> NAME/KEY: MOD_RES
<222> LOCATION: (8)
<223> OTHER INFORMATION: Xaa = Gly, beta-alanine, gamma-amino butyric
      acid or eta-amino caproic acid
<221> NAME/KEY: MOD_RES
<222> LOCATION: (11)
<223> OTHER INFORMATION: Xaa = Gly, beta-alanine, gamma-amino butyric
      acid or eta-amino caproic acid

<400> SEQUENCE: 35

Arg Xaa Arg Arg Xaa Arg Arg Xaa Arg Arg Xaa Arg Arg
  1               5                  10

<210> SEQ ID NO 36
<211> LENGTH: 16
<212> TYPE: PRT
<213> ORGANISM: Artificial Sequence
<220> FEATURE:
<223> OTHER INFORMATION: Description of Artificial Sequence:amino acid
      oligomer delivery enhancing transport moiety
<221> NAME/KEY: MOD_RES
<222> LOCATION: (2)
<223> OTHER INFORMATION: Xaa = Gly, beta-alanine, gamma-amino butyric
      acid or eta-amino caproic acid
```

```
<221> NAME/KEY: MOD_RES
<222> LOCATION: (5)
<223> OTHER INFORMATION: Xaa = Gly, beta-alanine, gamma-amino butyric
      acid or eta-amino caproic acid
<221> NAME/KEY: MOD_RES
<222> LOCATION: (8)
<223> OTHER INFORMATION: Xaa = Gly, beta-alanine, gamma-amino butyric
      acid or eta-amino caproic acid
<221> NAME/KEY: MOD_RES
<222> LOCATION: (11)
<223> OTHER INFORMATION: Xaa = Gly, beta-alanine, gamma-amino butyric
      acid or eta-amino caproic acid
<221> NAME/KEY: MOD_RES
<222> LOCATION: (14)
<223> OTHER INFORMATION: Xaa = Gly, beta-alanine, gamma-amino butyric
      acid or eta-amino caproic acid

<400> SEQUENCE: 36

Arg Xaa Arg Arg Xaa Arg Arg Xaa Arg Arg Xaa Arg Arg Xaa Arg Arg
 1               5                  10                  15

<210> SEQ ID NO 37
<211> LENGTH: 9
<212> TYPE: PRT
<213> ORGANISM: Artificial Sequence
<220> FEATURE:
<223> OTHER INFORMATION: Description of Artificial Sequence:amino acid
      oligomer delivery enhancing transport moiety
<221> NAME/KEY: MOD_RES
<222> LOCATION: (2)
<223> OTHER INFORMATION: Xaa = Gly, beta-alanine, gamma-amino butyric
      acid or eta-amino caproic acid
<221> NAME/KEY: MOD_RES
<222> LOCATION: (4)
<223> OTHER INFORMATION: Xaa = Gly, beta-alanine, gamma-amino butyric
      acid or eta-amino caproic acid
<221> NAME/KEY: MOD_RES
<222> LOCATION: (6)
<223> OTHER INFORMATION: Xaa = Gly, beta-alanine, gamma-amino butyric
      acid or eta-amino caproic acid
<221> NAME/KEY: MOD_RES
<222> LOCATION: (8)
<223> OTHER INFORMATION: Xaa = Gly, beta-alanine, gamma-amino butyric
      acid or eta-amino caproic acid

<400> SEQUENCE: 37

Arg Xaa Arg Xaa Arg Xaa Arg Xaa Arg
 1               5

<210> SEQ ID NO 38
<211> LENGTH: 11
<212> TYPE: PRT
<213> ORGANISM: Artificial Sequence
<220> FEATURE:
<223> OTHER INFORMATION: Description of Artificial Sequence:amino acid
      oligomer delivery enhancing transport moiety
<221> NAME/KEY: MOD_RES
<222> LOCATION: (2)
<223> OTHER INFORMATION: Xaa = Gly, beta-alanine, gamma-amino butyric
      acid or eta-amino caproic acid
<221> NAME/KEY: MOD_RES
<222> LOCATION: (4)
<223> OTHER INFORMATION: Xaa = Gly, beta-alanine, gamma-amino butyric
      acid or eta-amino caproic acid
<221> NAME/KEY: MOD_RES
<222> LOCATION: (6)
<223> OTHER INFORMATION: Xaa = Gly, beta-alanine, gamma-amino butyric
      acid or eta-amino caproic acid
<221> NAME/KEY: MOD_RES
<222> LOCATION: (8)
<223> OTHER INFORMATION: Xaa = Gly, beta-alanine, gamma-amino butyric
      acid or eta-amino caproic acid
<221> NAME/KEY: MOD_RES
<222> LOCATION: (10)
<223> OTHER INFORMATION: Xaa = Gly, beta-alanine, gamma-amino butyric
``` acid or eta-amino caproic acid

<400> SEQUENCE: 38

Arg Xaa Arg Xaa Arg Xaa Arg Xaa Arg Xaa Arg
 1               5                   10

<210> SEQ ID NO 39
<211> LENGTH: 13
<212> TYPE: PRT
<213> ORGANISM: Artificial Sequence
<220> FEATURE:
<223> OTHER INFORMATION: Description of Artificial Sequence:amino acid
      oligomer delivery enhancing transport moiety
<221> NAME/KEY: MOD_RES
<222> LOCATION: (2)
<223> OTHER INFORMATION: Xaa = Gly, beta-alanine, gamma-amino butyric
      acid or eta-amino caproic acid
<221> NAME/KEY: MOD_RES
<222> LOCATION: (4)
<223> OTHER INFORMATION: Xaa = Gly, beta-alanine, gamma-amino butyric
      acid or eta-amino caproic acid
<221> NAME/KEY: MOD_RES
<222> LOCATION: (6)
<223> OTHER INFORMATION: Xaa = Gly, beta-alanine, gamma-amino butyric
      acid or eta-amino caproic acid
<221> NAME/KEY: MOD_RES
<222> LOCATION: (8)
<223> OTHER INFORMATION: Xaa = Gly, beta-alanine, gamma-amino butyric
      acid or eta-amino caproic acid
<221> NAME/KEY: MOD_RES
<222> LOCATION: (10)
<223> OTHER INFORMATION: Xaa = Gly, beta-alanine, gamma-amino butyric
      acid or eta-amino caproic acid
<221> NAME/KEY: MOD_RES
<222> LOCATION: (12)
<223> OTHER INFORMATION: Xaa = Gly, beta-alanine, gamma-amino butyric
      acid or eta-amino caproic acid

<400> SEQUENCE: 39

Arg Xaa Arg Xaa Arg Xaa Arg Xaa Arg Xaa Arg Xaa Arg
 1               5                   10

<210> SEQ ID NO 40
<211> LENGTH: 15
<212> TYPE: PRT
<213> ORGANISM: Artificial Sequence
<220> FEATURE:
<223> OTHER INFORMATION: Description of Artificial Sequence:amino acid
      oligomer delivery enhancing transport moiety
<221> NAME/KEY: MOD_RES
<222> LOCATION: (2)
<223> OTHER INFORMATION: Xaa = Gly, beta-alanine, gamma-amino butyric
      acid or eta-amino caproic acid
<221> NAME/KEY: MOD_RES
<222> LOCATION: (4)
<223> OTHER INFORMATION: Xaa = Gly, beta-alanine, gamma-amino butyric
      acid or eta-amino caproic acid
<221> NAME/KEY: MOD_RES
<222> LOCATION: (6)
<223> OTHER INFORMATION: Xaa = Gly, beta-alanine, gamma-amino butyric
      acid or eta-amino caproic acid
<221> NAME/KEY: MOD_RES
<222> LOCATION: (8)
<223> OTHER INFORMATION: Xaa = Gly, beta-alanine, gamma-amino butyric
      acid or eta-amino caproic acid
<221> NAME/KEY: MOD_RES
<222> LOCATION: (10)
<223> OTHER INFORMATION: Xaa = Gly, beta-alanine, gamma-amino butyric
      acid or eta-amino caproic acid
<221> NAME/KEY: MOD_RES
<222> LOCATION: (12)
<223> OTHER INFORMATION: Xaa = Gly, beta-alanine, gamma-amino butyric
      acid or eta-amino caproic acid
<221> NAME/KEY: MOD_RES
<222> LOCATION: (14)

```
<223> OTHER INFORMATION: Xaa = Gly, beta-alanine, gamma-amino butyric
      acid or eta-amino caproic acid

<400> SEQUENCE: 40

Arg Xaa Arg Xaa Arg Xaa Arg Xaa Arg Xaa Arg Xaa Arg Xaa Arg
  1               5                  10                  15

<210> SEQ ID NO 41
<211> LENGTH: 17
<212> TYPE: PRT
<213> ORGANISM: Artificial Sequence
<220> FEATURE:
<223> OTHER INFORMATION: Description of Artificial Sequence:amino acid
      oligomer delivery enhancing transport moiety
<221> NAME/KEY: MOD_RES
<222> LOCATION: (2)
<223> OTHER INFORMATION: Xaa = Gly, beta-alanine, gamma-amino butyric
      acid or eta-amino caproic acid
<221> NAME/KEY: MOD_RES
<222> LOCATION: (4)
<223> OTHER INFORMATION: Xaa = Gly, beta-alanine, gamma-amino butyric
      acid or eta-amino caproic acid
<221> NAME/KEY: MOD_RES
<222> LOCATION: (6)
<223> OTHER INFORMATION: Xaa = Gly, beta-alanine, gamma-amino butyric
      acid or eta-amino caproic acid
<221> NAME/KEY: MOD_RES
<222> LOCATION: (8)
<223> OTHER INFORMATION: Xaa = Gly, beta-alanine, gamma-amino butyric
      acid or eta-amino caproic acid
<221> NAME/KEY: MOD_RES
<222> LOCATION: (10)
<223> OTHER INFORMATION: Xaa = Gly, beta-alanine, gamma-amino butyric
      acid or eta-amino caproic acid
<221> NAME/KEY: MOD_RES
<222> LOCATION: (12)
<223> OTHER INFORMATION: Xaa = Gly, beta-alanine, gamma-amino butyric
      acid or eta-amino caproic acid
<221> NAME/KEY: MOD_RES
<222> LOCATION: (14)
<223> OTHER INFORMATION: Xaa = Gly, beta-alanine, gamma-amino butyric
      acid or eta-amino caproic acid
<221> NAME/KEY: MOD_RES
<222> LOCATION: (16)
<223> OTHER INFORMATION: Xaa = Gly, beta-alanine, gamma-amino butyric
      acid or eta-amino caproic acid

<400> SEQUENCE: 41

Arg Xaa Arg Xaa Arg Xaa Arg Xaa Arg Xaa Arg Xaa Arg Xaa Arg Xaa
  1               5                  10                  15

Arg

<210> SEQ ID NO 42
<211> LENGTH: 19
<212> TYPE: PRT
<213> ORGANISM: Artificial Sequence
<220> FEATURE:
<223> OTHER INFORMATION: Description of Artificial Sequence:amino acid
      oligomer delivery enhancing transport moiety
<221> NAME/KEY: MOD_RES
<222> LOCATION: (2)
<223> OTHER INFORMATION: Xaa = Gly, beta-alanine, gamma-amino butyric
      acid or eta-amino caproic acid
<221> NAME/KEY: MOD_RES
<222> LOCATION: (4)
<223> OTHER INFORMATION: Xaa = Gly, beta-alanine, gamma-amino butyric
      acid or eta-amino caproic acid
<221> NAME/KEY: MOD_RES
<222> LOCATION: (6)
<223> OTHER INFORMATION: Xaa = Gly, beta-alanine, gamma-amino butyric
      acid or eta-amino caproic acid
<221> NAME/KEY: MOD_RES
<222> LOCATION: (8)
<223> OTHER INFORMATION: Xaa = Gly, beta-alanine, gamma-amino butyric
```

```
            acid or eta-amino caproic acid
<221> NAME/KEY: MOD_RES
<222> LOCATION: (10)
<223> OTHER INFORMATION: Xaa = Gly, beta-alanine, gamma-amino butyric
            acid or eta-amino caproic acid
<221> NAME/KEY: MOD_RES
<222> LOCATION: (12)
<223> OTHER INFORMATION: Xaa = Gly, beta-alanine, gamma-amino butyric
            acid or eta-amino caproic acid
<221> NAME/KEY: MOD_RES
<222> LOCATION: (14)
<223> OTHER INFORMATION: Xaa = Gly, beta-alanine, gamma-amino butyric
            acid or eta-amino caproic acid
<221> NAME/KEY: MOD_RES
<222> LOCATION: (16)
<223> OTHER INFORMATION: Xaa = Gly, beta-alanine, gamma-amino butyric
            acid or eta-amino caproic acid
<221> NAME/KEY: MOD_RES
<222> LOCATION: (18)
<223> OTHER INFORMATION: Xaa = Gly, beta-alanine, gamma-amino butyric
            acid or eta-amino caproic acid

<400> SEQUENCE: 42

Arg Xaa Arg Xaa Arg Xaa Arg Xaa Arg Xaa Arg Xaa Arg Xaa Arg Xaa
  1               5                  10                  15

Arg Xaa Arg

<210> SEQ ID NO 43
<211> LENGTH: 21
<212> TYPE: PRT
<213> ORGANISM: Artificial Sequence
<220> FEATURE:
<223> OTHER INFORMATION: Description of Artificial Sequence:amino acid
            oligomer delivery enhancing transport moiety
<221> NAME/KEY: MOD_RES
<222> LOCATION: (2)
<223> OTHER INFORMATION: Xaa = Gly, beta-alanine, gamma-amino butyric
            acid or eta-amino caproic acid
<221> NAME/KEY: MOD_RES
<222> LOCATION: (4)
<223> OTHER INFORMATION: Xaa = Gly, beta-alanine, gamma-amino butyric
            acid or eta-amino caproic acid
<221> NAME/KEY: MOD_RES
<222> LOCATION: (6)
<223> OTHER INFORMATION: Xaa = Gly, beta-alanine, gamma-amino butyric
            acid or eta-amino caproic acid
<221> NAME/KEY: MOD_RES
<222> LOCATION: (8)
<223> OTHER INFORMATION: Xaa = Gly, beta-alanine, gamma-amino butyric
            acid or eta-amino caproic acid
<221> NAME/KEY: MOD_RES
<222> LOCATION: (10)
<223> OTHER INFORMATION: Xaa = Gly, beta-alanine, gamma-amino butyric
            acid or eta-amino caproic acid
<221> NAME/KEY: MOD_RES
<222> LOCATION: (12)
<223> OTHER INFORMATION: Xaa = Gly, beta-alanine, gamma-amino butyric
            acid or eta-amino caproic acid
<221> NAME/KEY: MOD_RES
<222> LOCATION: (14)
<223> OTHER INFORMATION: Xaa = Gly, beta-alanine, gamma-amino butyric
            acid or eta-amino caproic acid
<221> NAME/KEY: MOD_RES
<222> LOCATION: (16)
<223> OTHER INFORMATION: Xaa = Gly, beta-alanine, gamma-amino butyric
            acid or eta-amino caproic acid
<221> NAME/KEY: MOD_RES
<222> LOCATION: (18)
<223> OTHER INFORMATION: Xaa = Gly, beta-alanine, gamma-amino butyric
            acid or eta-amino caproic acid
<221> NAME/KEY: MOD_RES
<222> LOCATION: (20)
<223> OTHER INFORMATION: Xaa = Gly, beta-alanine, gamma-amino butyric
            acid or eta-amino caproic acid

<400> SEQUENCE: 43
```

Arg Xaa Arg Xaa Arg Xaa Arg Xaa Arg Xaa Arg Xaa Arg Xaa Arg Xaa
1               5                   10                  15

Arg Xaa Arg Xaa Arg
            20

<210> SEQ ID NO 44
<211> LENGTH: 13
<212> TYPE: PRT
<213> ORGANISM: Artificial Sequence
<220> FEATURE:
<223> OTHER INFORMATION: Description of Artificial Sequence:amino acid
      oligomer delivery enhancing transport moiety
<221> NAME/KEY: MOD_RES
<222> LOCATION: (2..3)
<223> OTHER INFORMATION: Xaa = Gly, beta-alanine, gamma-amino butyric
      acid or eta-amino caproic acid
<221> NAME/KEY: MOD_RES
<222> LOCATION: (5..6)
<223> OTHER INFORMATION: Xaa = Gly, beta-alanine, gamma-amino butyric
      acid or eta-amino caproic acid
<221> NAME/KEY: MOD_RES
<222> LOCATION: (8..9)
<223> OTHER INFORMATION: Xaa = Gly, beta-alanine, gamma-amino butyric
      acid or eta-amino caproic acid
<221> NAME/KEY: MOD_RES
<222> LOCATION: (11..12)
<223> OTHER INFORMATION: Xaa = Gly, beta-alanine, gamma-amino butyric
      acid or eta-amino caproic acid

<400> SEQUENCE: 44

Arg Xaa Xaa Arg Xaa Xaa Arg Xaa Xaa Arg Xaa Xaa Arg
1               5                   10

<210> SEQ ID NO 45
<211> LENGTH: 16
<212> TYPE: PRT
<213> ORGANISM: Artificial Sequence
<220> FEATURE:
<223> OTHER INFORMATION: Description of Artificial Sequence:amino acid
      oligomer delivery enhancing transport moiety
<221> NAME/KEY: MOD_RES
<222> LOCATION: (2..3)
<223> OTHER INFORMATION: Xaa = Gly, beta-alanine, gamma-amino butyric
      acid or eta-amino caproic acid
<221> NAME/KEY: MOD_RES
<222> LOCATION: (5..6)
<223> OTHER INFORMATION: Xaa = Gly, beta-alanine, gamma-amino butyric
      acid or eta-amino caproic acid
<221> NAME/KEY: MOD_RES
<222> LOCATION: (8..9)
<223> OTHER INFORMATION: Xaa = Gly, beta-alanine, gamma-amino butyric
      acid or eta-amino caproic acid
<221> NAME/KEY: MOD_RES
<222> LOCATION: (11..12)
<223> OTHER INFORMATION: Xaa = Gly, beta-alanine, gamma-amino butyric
      acid or eta-amino caproic acid
<221> NAME/KEY: MOD_RES
<222> LOCATION: (14..15)
<223> OTHER INFORMATION: Xaa = Gly, beta-alanine, gamma-amino butyric
      acid or eta-amino caproic acid

<400> SEQUENCE: 45

Arg Xaa Xaa Arg Xaa Xaa Arg Xaa Xaa Arg Xaa Xaa Arg Xaa Xaa Arg
1               5                   10                  15

<210> SEQ ID NO 46
<211> LENGTH: 19
<212> TYPE: PRT
<213> ORGANISM: Artificial Sequence
<220> FEATURE:
<223> OTHER INFORMATION: Description of Artificial Sequence:amino acid
      oligomer delivery enhancing transport moiety

```
<221> NAME/KEY: MOD_RES
<222> LOCATION: (2..3)
<223> OTHER INFORMATION: Xaa = Gly, beta-alanine, gamma-amino butyric
      acid or eta-amino caproic acid
<221> NAME/KEY: MOD_RES
<222> LOCATION: (5..6)
<223> OTHER INFORMATION: Xaa = Gly, beta-alanine, gamma-amino butyric
      acid or eta-amino caproic acid
<221> NAME/KEY: MOD_RES
<222> LOCATION: (8..9)
<223> OTHER INFORMATION: Xaa = Gly, beta-alanine, gamma-amino butyric
      acid or eta-amino caproic acid
<221> NAME/KEY: MOD_RES
<222> LOCATION: (11..12)
<223> OTHER INFORMATION: Xaa = Gly, beta-alanine, gamma-amino butyric
      acid or eta-amino caproic acid
<221> NAME/KEY: MOD_RES
<222> LOCATION: (14..15)
<223> OTHER INFORMATION: Xaa = Gly, beta-alanine, gamma-amino butyric
      acid or eta-amino caproic acid
<221> NAME/KEY: MOD_RES
<222> LOCATION: (17..18)
<223> OTHER INFORMATION: Xaa = Gly, beta-alanine, gamma-amino butyric
      acid or eta-amino caproic acid

<400> SEQUENCE: 46

Arg Xaa Xaa Arg Xaa Xaa Arg Xaa Xaa Arg Xaa Xaa Arg Xaa Xaa Arg
 1               5                  10                  15

Xaa Xaa Arg

<210> SEQ ID NO 47
<211> LENGTH: 22
<212> TYPE: PRT
<213> ORGANISM: Artificial Sequence
<220> FEATURE:
<223> OTHER INFORMATION: Description of Artificial Sequence:amino acid
      oligomer delivery enhancing transport moiety
<221> NAME/KEY: MOD_RES
<222> LOCATION: (2..3)
<223> OTHER INFORMATION: Xaa = Gly, beta-alanine, gamma-amino butyric
      acid or eta-amino caproic acid
<221> NAME/KEY: MOD_RES
<222> LOCATION: (5..6)
<223> OTHER INFORMATION: Xaa = Gly, beta-alanine, gamma-amino butyric
      acid or eta-amino caproic acid
<221> NAME/KEY: MOD_RES
<222> LOCATION: (8..9)
<223> OTHER INFORMATION: Xaa = Gly, beta-alanine, gamma-amino butyric
      acid or eta-amino caproic acid
<221> NAME/KEY: MOD_RES
<222> LOCATION: (11..12)
<223> OTHER INFORMATION: Xaa = Gly, beta-alanine, gamma-amino butyric
      acid or eta-amino caproic acid
<221> NAME/KEY: MOD_RES
<222> LOCATION: (14..15)
<223> OTHER INFORMATION: Xaa = Gly, beta-alanine, gamma-amino butyric
      acid or eta-amino caproic acid
<221> NAME/KEY: MOD_RES
<222> LOCATION: (17..18)
<223> OTHER INFORMATION: Xaa = Gly, beta-alanine, gamma-amino butyric
      acid or eta-amino caproic acid
<221> NAME/KEY: MOD_RES
<222> LOCATION: (20..21)
<223> OTHER INFORMATION: Xaa = Gly, beta-alanine, gamma-amino butyric
      acid or eta-amino caproic acid

<400> SEQUENCE: 47

Arg Xaa Xaa Arg Xaa Xaa Arg Xaa Xaa Arg Xaa Xaa Arg Xaa Xaa Arg
 1               5                  10                  15

Xaa Xaa Arg Xaa Xaa Arg
            20

<210> SEQ ID NO 48
```

```
<211> LENGTH: 25
<212> TYPE: PRT
<213> ORGANISM: Artificial Sequence
<220> FEATURE:
<223> OTHER INFORMATION: Description of Artificial Sequence:amino acid
      oligomer delivery enhancing transport moiety
<221> NAME/KEY: MOD_RES
<222> LOCATION: (2..3)
<223> OTHER INFORMATION: Xaa = Gly, beta-alanine, gamma-amino butyric
      acid or eta-amino caproic acid
<221> NAME/KEY: MOD_RES
<222> LOCATION: (5..6)
<223> OTHER INFORMATION: Xaa = Gly, beta-alanine, gamma-amino butyric
      acid or eta-amino caproic acid
<221> NAME/KEY: MOD_RES
<222> LOCATION: (8..9)
<223> OTHER INFORMATION: Xaa = Gly, beta-alanine, gamma-amino butyric
      acid or eta-amino caproic acid
<221> NAME/KEY: MOD_RES
<222> LOCATION: (11..12)
<223> OTHER INFORMATION: Xaa = Gly, beta-alanine, gamma-amino butyric
      acid or eta-amino caproic acid
<221> NAME/KEY: MOD_RES
<222> LOCATION: (14..15)
<223> OTHER INFORMATION: Xaa = Gly, beta-alanine, gamma-amino butyric
      acid or eta-amino caproic acid
<221> NAME/KEY: MOD_RES
<222> LOCATION: (17..18)
<223> OTHER INFORMATION: Xaa = Gly, beta-alanine, gamma-amino butyric
      acid or eta-amino caproic acid
<221> NAME/KEY: MOD_RES
<222> LOCATION: (20..21)
<223> OTHER INFORMATION: Xaa = Gly, beta-alanine, gamma-amino butyric
      acid or eta-amino caproic acid
<221> NAME/KEY: MOD_RES
<222> LOCATION: (23..24)
<223> OTHER INFORMATION: Xaa = Gly, beta-alanine, gamma-amino butyric
      acid or eta-amino caproic acid

<400> SEQUENCE: 48

Arg Xaa Xaa Arg Xaa Xaa Arg Xaa Xaa Arg Xaa Xaa Arg Xaa Xaa Arg
 1               5                  10                  15

Xaa Xaa Arg Xaa Xaa Arg Xaa Xaa Arg
            20                  25

<210> SEQ ID NO 49
<211> LENGTH: 28
<212> TYPE: PRT
<213> ORGANISM: Artificial Sequence
<220> FEATURE:
<223> OTHER INFORMATION: Description of Artificial Sequence:amino acid
      oligomer delivery enhancing transport moiety
<221> NAME/KEY: MOD_RES
<222> LOCATION: (2..3)
<223> OTHER INFORMATION: Xaa = Gly, beta-alanine, gamma-amino butyric
      acid or eta-amino caproic acid
<221> NAME/KEY: MOD_RES
<222> LOCATION: (5..6)
<223> OTHER INFORMATION: Xaa = Gly, beta-alanine, gamma-amino butyric
      acid or eta-amino caproic acid
<221> NAME/KEY: MOD_RES
<222> LOCATION: (8..9)
<223> OTHER INFORMATION: Xaa = Gly, beta-alanine, gamma-amino butyric
      acid or eta-amino caproic acid
<221> NAME/KEY: MOD_RES
<222> LOCATION: (11..12)
<223> OTHER INFORMATION: Xaa = Gly, beta-alanine, gamma-amino butyric
      acid or eta-amino caproic acid
<221> NAME/KEY: MOD_RES
<222> LOCATION: (14..15)
<223> OTHER INFORMATION: Xaa = Gly, beta-alanine, gamma-amino butyric
      acid or eta-amino caproic acid
<221> NAME/KEY: MOD_RES
<222> LOCATION: (17..18)
<223> OTHER INFORMATION: Xaa = Gly, beta-alanine, gamma-amino butyric
      acid or eta-amino caproic acid
```

```
<221> NAME/KEY: MOD_RES
<222> LOCATION: (20..21)
<223> OTHER INFORMATION: Xaa = Gly, beta-alanine, gamma-amino butyric
      acid or eta-amino caproic acid
<221> NAME/KEY: MOD_RES
<222> LOCATION: (23..24)
<223> OTHER INFORMATION: Xaa = Gly, beta-alanine, gamma-amino butyric
      acid or eta-amino caproic acid
<221> NAME/KEY: MOD_RES
<222> LOCATION: (26..27)
<223> OTHER INFORMATION: Xaa = Gly, beta-alanine, gamma-amino butyric
      acid or eta-amino caproic acid

<400> SEQUENCE: 49

Arg Xaa Xaa Arg Xaa Xaa Arg Xaa Xaa Arg Xaa Xaa Arg Xaa Xaa Arg
 1               5                  10                  15

Xaa Xaa Arg Xaa Xaa Arg Xaa Xaa Arg Xaa Xaa Arg
            20                  25

<210> SEQ ID NO 50
<211> LENGTH: 31
<212> TYPE: PRT
<213> ORGANISM: Artificial Sequence
<220> FEATURE:
<223> OTHER INFORMATION: Description of Artificial Sequence:amino acid
      oligomer delivery enhancing transport moiety
<221> NAME/KEY: MOD_RES
<222> LOCATION: (2..3)
<223> OTHER INFORMATION: Xaa = Gly, beta-alanine, gamma-amino butyric
      acid or eta-amino caproic acid
<221> NAME/KEY: MOD_RES
<222> LOCATION: (5..6)
<223> OTHER INFORMATION: Xaa = Gly, beta-alanine, gamma-amino butyric
      acid or eta-amino caproic acid
<221> NAME/KEY: MOD_RES
<222> LOCATION: (8..9)
<223> OTHER INFORMATION: Xaa = Gly, beta-alanine, gamma-amino butyric
      acid or eta-amino caproic acid
<221> NAME/KEY: MOD_RES
<222> LOCATION: (11..12)
<223> OTHER INFORMATION: Xaa = Gly, beta-alanine, gamma-amino butyric
      acid or eta-amino caproic acid
<221> NAME/KEY: MOD_RES
<222> LOCATION: (14..15)
<223> OTHER INFORMATION: Xaa = Gly, beta-alanine, gamma-amino butyric
      acid or eta-amino caproic acid
<221> NAME/KEY: MOD_RES
<222> LOCATION: (17..18)
<223> OTHER INFORMATION: Xaa = Gly, beta-alanine, gamma-amino butyric
      acid or eta-amino caproic acid
<221> NAME/KEY: MOD_RES
<222> LOCATION: (20..21)
<223> OTHER INFORMATION: Xaa = Gly, beta-alanine, gamma-amino butyric
      acid or eta-amino caproic acid
<221> NAME/KEY: MOD_RES
<222> LOCATION: (23..24)
<223> OTHER INFORMATION: Xaa = Gly, beta-alanine, gamma-amino butyric
      acid or eta-amino caproic acid
<221> NAME/KEY: MOD_RES
<222> LOCATION: (26..27)
<223> OTHER INFORMATION: Xaa = Gly, beta-alanine, gamma-amino butyric
      acid or eta-amino caproic acid
<221> NAME/KEY: MOD_RES
<222> LOCATION: (29..30)
<223> OTHER INFORMATION: Xaa = Gly, beta-alanine, gamma-amino butyric
      acid or eta-amino caproic acid

<400> SEQUENCE: 50

Arg Xaa Xaa Arg Xaa Xaa Arg Xaa Xaa Arg Xaa Xaa Arg Xaa Xaa Arg
 1               5                  10                  15

Xaa Xaa Arg Xaa Xaa Arg Xaa Xaa Arg Xaa Xaa Arg Xaa Xaa Arg
            20                  25                  30
```

```
<210> SEQ ID NO 51
<211> LENGTH: 17
<212> TYPE: PRT
<213> ORGANISM: Artificial Sequence
<220> FEATURE:
<223> OTHER INFORMATION: Description of Artificial Sequence:amino acid
      oligomer delivery enhancing transport moiety
<221> NAME/KEY: MOD_RES
<222> LOCATION: (2..4)
<223> OTHER INFORMATION: Xaa = Gly, beta-alanine, gamma-amino butyric
      acid or eta-amino caproic acid
<221> NAME/KEY: MOD_RES
<222> LOCATION: (6..8)
<223> OTHER INFORMATION: Xaa = Gly, beta-alanine, gamma-amino butyric
      acid or eta-amino caproic acid
<221> NAME/KEY: MOD_RES
<222> LOCATION: (10..12)
<223> OTHER INFORMATION: Xaa = Gly, beta-alanine, gamma-amino butyric
      acid or eta-amino caproic acid
<221> NAME/KEY: MOD_RES
<222> LOCATION: (14..16)
<223> OTHER INFORMATION: Xaa = Gly, beta-alanine, gamma-amino butyric
      acid or eta-amino caproic acid

<400> SEQUENCE: 51

Arg Xaa Xaa Xaa Arg Xaa Xaa Xaa Arg Xaa Xaa Xaa Arg Xaa Xaa Xaa
 1               5                  10                  15

Arg

<210> SEQ ID NO 52
<211> LENGTH: 21
<212> TYPE: PRT
<213> ORGANISM: Artificial Sequence
<220> FEATURE:
<223> OTHER INFORMATION: Description of Artificial Sequence:amino acid
      oligomer delivery enhancing transport moiety
<221> NAME/KEY: MOD_RES
<222> LOCATION: (2..4)
<223> OTHER INFORMATION: Xaa = Gly, beta-alanine, gamma-amino butyric
      acid or eta-amino caproic acid
<221> NAME/KEY: MOD_RES
<222> LOCATION: (6..8)
<223> OTHER INFORMATION: Xaa = Gly, beta-alanine, gamma-amino butyric
      acid or eta-amino caproic acid
<221> NAME/KEY: MOD_RES
<222> LOCATION: (10..12)
<223> OTHER INFORMATION: Xaa = Gly, beta-alanine, gamma-amino butyric
      acid or eta-amino caproic acid
<221> NAME/KEY: MOD_RES
<222> LOCATION: (14..16)
<223> OTHER INFORMATION: Xaa = Gly, beta-alanine, gamma-amino butyric
      acid or eta-amino caproic acid
<221> NAME/KEY: MOD_RES
<222> LOCATION: (18..20)
<223> OTHER INFORMATION: Xaa = Gly, beta-alanine, gamma-amino butyric
      acid or eta-amino caproic acid

<400> SEQUENCE: 52

Arg Xaa Xaa Xaa Arg Xaa Xaa Xaa Arg Xaa Xaa Xaa Arg Xaa Xaa Xaa
 1               5                  10                  15

Arg Xaa Xaa Xaa Arg
            20

<210> SEQ ID NO 53
<211> LENGTH: 25
<212> TYPE: PRT
<213> ORGANISM: Artificial Sequence
<220> FEATURE:
<223> OTHER INFORMATION: Description of Artificial Sequence:amino acid
      oligomer delivery enhancing transport moiety
<221> NAME/KEY: MOD_RES
<222> LOCATION: (2..4)
<223> OTHER INFORMATION: Xaa = Gly, beta-alanine, gamma-amino butyric
```

```
        acid or eta-amino caproic acid
<221> NAME/KEY: MOD_RES
<222> LOCATION: (6..8)
<223> OTHER INFORMATION: Xaa = Gly, beta-alanine, gamma-amino butyric
        acid or eta-amino caproic acid
<221> NAME/KEY: MOD_RES
<222> LOCATION: (10..12)
<223> OTHER INFORMATION: Xaa = Gly, beta-alanine, gamma-amino butyric
        acid or eta-amino caproic acid
<221> NAME/KEY: MOD_RES
<222> LOCATION: (14..16)
<223> OTHER INFORMATION: Xaa = Gly, beta-alanine, gamma-amino butyric
        acid or eta-amino caproic acid
<221> NAME/KEY: MOD_RES
<222> LOCATION: (18..20)
<223> OTHER INFORMATION: Xaa = Gly, beta-alanine, gamma-amino butyric
        acid or eta-amino caproic acid
<221> NAME/KEY: MOD_RES
<222> LOCATION: (22..24)
<223> OTHER INFORMATION: Xaa = Gly, beta-alanine, gamma-amino butyric
        acid or eta-amino caproic acid

<400> SEQUENCE: 53

Arg Xaa Xaa Xaa Arg Xaa Xaa Xaa Arg Xaa Xaa Xaa Arg Xaa Xaa Xaa
 1               5                  10                  15

Arg Xaa Xaa Xaa Arg Xaa Xaa Xaa Arg
            20                  25

<210> SEQ ID NO 54
<211> LENGTH: 29
<212> TYPE: PRT
<213> ORGANISM: Artificial Sequence
<220> FEATURE:
<223> OTHER INFORMATION: Description of Artificial Sequence:amino acid
        oligomer delivery enhancing transport moiety
<221> NAME/KEY: MOD_RES
<222> LOCATION: (2..4)
<223> OTHER INFORMATION: Xaa = Gly, beta-alanine, gamma-amino butyric
        acid or eta-amino caproic acid
<221> NAME/KEY: MOD_RES
<222> LOCATION: (6..8)
<223> OTHER INFORMATION: Xaa = Gly, beta-alanine, gamma-amino butyric
        acid or eta-amino caproic acid
<221> NAME/KEY: MOD_RES
<222> LOCATION: (10..12)
<223> OTHER INFORMATION: Xaa = Gly, beta-alanine, gamma-amino butyric
        acid or eta-amino caproic acid
<221> NAME/KEY: MOD_RES
<222> LOCATION: (14..16)
<223> OTHER INFORMATION: Xaa = Gly, beta-alanine, gamma-amino butyric
        acid or eta-amino caproic acid
<221> NAME/KEY: MOD_RES
<222> LOCATION: (18..20)
<223> OTHER INFORMATION: Xaa = Gly, beta-alanine, gamma-amino butyric
        acid or eta-amino caproic acid
<221> NAME/KEY: MOD_RES
<222> LOCATION: (22..24)
<223> OTHER INFORMATION: Xaa = Gly, beta-alanine, gamma-amino butyric
        acid or eta-amino caproic acid
<221> NAME/KEY: MOD_RES
<222> LOCATION: (26..28)
<223> OTHER INFORMATION: Xaa = Gly, beta-alanine, gamma-amino butyric
        acid or eta-amino caproic acid

<400> SEQUENCE: 54

Arg Xaa Xaa Xaa Arg Xaa Xaa Xaa Arg Xaa Xaa Xaa Arg Xaa Xaa Xaa
 1               5                  10                  15

Arg Xaa Xaa Xaa Arg Xaa Xaa Xaa Arg Xaa Xaa Xaa Arg
            20                  25

<210> SEQ ID NO 55
<211> LENGTH: 33
<212> TYPE: PRT
```

```
<213> ORGANISM: Artificial Sequence
<220> FEATURE:
<223> OTHER INFORMATION: Description of Artificial Sequence:amino acid
      oligomer delivery enhancing transport moiety
<221> NAME/KEY: MOD_RES
<222> LOCATION: (2..4)
<223> OTHER INFORMATION: Xaa = Gly, beta-alanine, gamma-amino butyric
      acid or eta-amino caproic acid
<221> NAME/KEY: MOD_RES
<222> LOCATION: (6..8)
<223> OTHER INFORMATION: Xaa = Gly, beta-alanine, gamma-amino butyric
      acid or eta-amino caproic acid
<221> NAME/KEY: MOD_RES
<222> LOCATION: (10..12)
<223> OTHER INFORMATION: Xaa = Gly, beta-alanine, gamma-amino butyric
      acid or eta-amino caproic acid
<221> NAME/KEY: MOD_RES
<222> LOCATION: (14..16)
<223> OTHER INFORMATION: Xaa = Gly, beta-alanine, gamma-amino butyric
      acid or eta-amino caproic acid
<221> NAME/KEY: MOD_RES
<222> LOCATION: (18..20)
<223> OTHER INFORMATION: Xaa = Gly, beta-alanine, gamma-amino butyric
      acid or eta-amino caproic acid
<221> NAME/KEY: MOD_RES
<222> LOCATION: (22..24)
<223> OTHER INFORMATION: Xaa = Gly, beta-alanine, gamma-amino butyric
      acid or eta-amino caproic acid
<221> NAME/KEY: MOD_RES
<222> LOCATION: (26..28)
<223> OTHER INFORMATION: Xaa = Gly, beta-alanine, gamma-amino butyric
      acid or eta-amino caproic acid
<221> NAME/KEY: MOD_RES
<222> LOCATION: (30..32)
<223> OTHER INFORMATION: Xaa = Gly, beta-alanine, gamma-amino butyric
      acid or eta-amino caproic acid

<400> SEQUENCE: 55

Arg Xaa Xaa Xaa Arg Xaa Xaa Xaa Arg Xaa Xaa Xaa Arg Xaa Xaa Xaa
 1               5                  10                  15

Arg Xaa Xaa Xaa Arg Xaa Xaa Xaa Arg Xaa Xaa Xaa Arg Xaa Xaa Xaa
            20                  25                  30

Arg

<210> SEQ ID NO 56
<211> LENGTH: 37
<212> TYPE: PRT
<213> ORGANISM: Artificial Sequence
<220> FEATURE:
<223> OTHER INFORMATION: Description of Artificial Sequence:amino acid
      oligomer delivery enhancing transport moiety
<221> NAME/KEY: MOD_RES
<222> LOCATION: (2..4)
<223> OTHER INFORMATION: Xaa = Gly, beta-alanine, gamma-amino butyric
      acid or eta-amino caproic acid
<221> NAME/KEY: MOD_RES
<222> LOCATION: (6..8)
<223> OTHER INFORMATION: Xaa = Gly, beta-alanine, gamma-amino butyric
      acid or eta-amino caproic acid
<221> NAME/KEY: MOD_RES
<222> LOCATION: (10..12)
<223> OTHER INFORMATION: Xaa = Gly, beta-alanine, gamma-amino butyric
      acid or eta-amino caproic acid
<221> NAME/KEY: MOD_RES
<222> LOCATION: (14..16)
<223> OTHER INFORMATION: Xaa = Gly, beta-alanine, gamma-amino butyric
      acid or eta-amino caproic acid
<221> NAME/KEY: MOD_RES
<222> LOCATION: (18..20)
<223> OTHER INFORMATION: Xaa = Gly, beta-alanine, gamma-amino butyric
      acid or eta-amino caproic acid
<221> NAME/KEY: MOD_RES
<222> LOCATION: (22..24)
<223> OTHER INFORMATION: Xaa = Gly, beta-alanine, gamma-amino butyric
      acid or eta-amino caproic acid
```

<221> NAME/KEY: MOD_RES
<222> LOCATION: (26..28)
<223> OTHER INFORMATION: Xaa = Gly, beta-alanine, gamma-amino butyric
      acid or eta-amino caproic acid
<221> NAME/KEY: MOD_RES
<222> LOCATION: (30..32)
<223> OTHER INFORMATION: Xaa = Gly, beta-alanine, gamma-amino butyric
      acid or eta-amino caproic acid
<221> NAME/KEY: MOD_RES
<222> LOCATION: (34..36)
<223> OTHER INFORMATION: Xaa = Gly, beta-alanine, gamma-amino butyric
      acid or eta-amino caproic acid

<400> SEQUENCE: 56

Arg Xaa Xaa Xaa Arg Xaa Xaa Xaa Arg Xaa Xaa Xaa Arg Xaa Xaa Xaa
 1               5                   10                  15

Arg Xaa Xaa Xaa Arg Xaa Xaa Xaa Arg Xaa Xaa Xaa Arg Xaa Xaa Xaa
             20                  25                  30

Arg Xaa Xaa Xaa Arg
         35

<210> SEQ ID NO 57
<211> LENGTH: 41
<212> TYPE: PRT
<213> ORGANISM: Artificial Sequence
<220> FEATURE:
<223> OTHER INFORMATION: Description of Artificial Sequence:amino acid
      oligomer delivery enhancing transport moiety
<221> NAME/KEY: MOD_RES
<222> LOCATION: (2..4)
<223> OTHER INFORMATION: Xaa = Gly, beta-alanine, gamma-amino butyric
      acid or eta-amino caproic acid
<221> NAME/KEY: MOD_RES
<222> LOCATION: (6..8)
<223> OTHER INFORMATION: Xaa = Gly, beta-alanine, gamma-amino butyric
      acid or eta-amino caproic acid
<221> NAME/KEY: MOD_RES
<222> LOCATION: (10..12)
<223> OTHER INFORMATION: Xaa = Gly, beta-alanine, gamma-amino butyric
      acid or eta-amino caproic acid
<221> NAME/KEY: MOD_RES
<222> LOCATION: (14..16)
<223> OTHER INFORMATION: Xaa = Gly, beta-alanine, gamma-amino butyric
      acid or eta-amino caproic acid
<221> NAME/KEY: MOD_RES
<222> LOCATION: (18..20)
<223> OTHER INFORMATION: Xaa = Gly, beta-alanine, gamma-amino butyric
      acid or eta-amino caproic acid
<221> NAME/KEY: MOD_RES
<222> LOCATION: (22..24)
<223> OTHER INFORMATION: Xaa = Gly, beta-alanine, gamma-amino butyric
      acid or eta-amino caproic acid
<221> NAME/KEY: MOD_RES
<222> LOCATION: (26..28)
<223> OTHER INFORMATION: Xaa = Gly, beta-alanine, gamma-amino butyric
      acid or eta-amino caproic acid
<221> NAME/KEY: MOD_RES
<222> LOCATION: (30..32)
<223> OTHER INFORMATION: Xaa = Gly, beta-alanine, gamma-amino butyric
      acid or eta-amino caproic acid
<221> NAME/KEY: MOD_RES
<222> LOCATION: (34..36)
<223> OTHER INFORMATION: Xaa = Gly, beta-alanine, gamma-amino butyric
      acid or eta-amino caproic acid
<221> NAME/KEY: MOD_RES
<222> LOCATION: (38..40)
<223> OTHER INFORMATION: Xaa = Gly, beta-alanine, gamma-amino butyric
      acid or eta-amino caproic acid

<400> SEQUENCE: 57

Arg Xaa Xaa Xaa Arg Xaa Xaa Xaa Arg Xaa Xaa Xaa Arg Xaa Xaa Xaa
 1               5                   10                  15

-continued

```
Arg Xaa Xaa Xaa Arg Xaa Xaa Xaa Arg Xaa Xaa Xaa Arg Xaa Xaa Xaa
             20                  25                  30

Arg Xaa Xaa Xaa Arg Xaa Xaa Xaa Arg
             35                  40
```

COMPOSITIONS AND METHODS FOR ENHANCING DRUG DELIVERY ACROSS AND INTO EPITHELIAL TISSUES

CROSS-REFERENCE TO RELATED APPLICATIONS

This application is a continuation-in-part application of U.S. patent application Ser. No. 09/648,400, Aug. 24, 2000, now U.S. Pat. No. 6,593,292, which claims priority to U.S. Provisional Patent Application No. 60/150,510, filed Aug. 24, 1999. Both of these applications are incorporated herein by reference for all purposes.

BACKGROUND OF THE INVENTION

1. Field of the Invention

This invention pertains to the field of compositions and methods that enhance the delivery of drugs and other compounds across the dermal and epithelial membranes, including, for example, skin, the gastrointestinal epithelium and the bronchial epithelium.

2. Background

Transdermal or transmucosal drug delivery is an attractive route of drug delivery for several reasons. Gastrointestinal drug degradation and the hepatic first-pass effect are avoided. In addition, transdermal and transmucosal drug delivery is well-suited to controlled, sustained delivery (see, e.g., Elias, In *Percutaneous Absorption: Mechanisms-Methodology-Drug Delivery*, Bronaugh & Maibach, Eds., pp 1–12, Marcel Dekker, New York, 1989.). For many applications, traditional methods of administering drugs are not optimal because of the very large initial concentration of the drug. Transdermal delivery could allow a more uniform, slower rate of delivery of a drug. Moreover, patient compliance is encouraged because such delivery methods are easy to use, comfortable, convenient and non-invasive.

These advantages of transdermal and transmucosal delivery have not led to many clinical applications because of the low permeability of epithelial membranes, the skin in particular, to drugs. The difficulties in delivering drugs across the skin result from the barrier property of skin. Skin is a structurally complex thick membrane that represents the body's border to the external hostile environment. The skin is composed of the epidermis, the dermis, the hypodermis, and the adenexal structures (epidermal appendages). The epidermis, the outermost epithelial tissue of the skin, is itself composed of several layers—the stratum corneum, the stratum granulosum, the stratum spinosum, and the stratum basale.

Compounds that move from the environment into and through intact skin must first penetrate the stratum corneum, the outermost layer of skin, which is compact and highly keratinized. The stratum corneum is composed of several layers of keratin-filled skin cells that are tightly bound together by a "glue" composed of cholesterol and fatty acids. The thickness of the stratum corneum varies depending upon body location. It is the presence of stratum corneum that results in the impermeability of the skin to pharmaceutical agents. The stratum corneum is formed naturally by cells migrating from the basal layer toward the skin surface where they are eventually sloughed off. As the cells progress toward the surface, they become progressively more dehydrated and keratinized. The penetration across the stratum corneum layer is generally the rate-limiting step of drug permeation across skin. See, e.g., Flynn, G. L., In *Percutaneous Absorption: Mechanisms-Methodology-Drug Delivery*, supra, at pages 27–53.

After penetration through the stratum corneum layer, systemically acting drug molecules then must pass into and through the epidermis, the dermis, and finally through the capillary walls of the bloodstream. The epidermis, which lies under the stratum corneum, is composed of three layers. The outermost of these layers is the stratum granulosum, which lies adjacent to the stratum corneum, is composed of cells that are differentiated from basal cells and keratinocytes, which make up the underlying layers. having acquired additional keratin and a more flattened shape. The cells of this layer of the epidermis, which contain granules that are composed largely of the protein filaggrin. This protein is believed to bind to the keratin filaments to form the keratin complex. The cells also synthesize lipids that function as a "cement" to hold the cells together. The epidermis, in particular the stratum granulosum, contains enzymes such as aminopeptidases.

The next-outermost layer of the epidermis is the stratum spinosum, the principal cells of which are keratinocytes, which are derived from basal cells that comprise the basal cell layer. Langerhans cells, which are also found in the stratum spinosum, are antigen-presenting cells and thus are involved in the mounting of an immune response against antigens that pass into the skin. The cells of this layer are generally involved in contact sensitivity dermatitis.

The innermost epidermal layer is the stratum basale, or basal cell layer, which consists of one cell layer of cuboidal cells that are attached by hemi-desmosomes to a thin basement membrane which separates the basal cell layer from the underlying dermis. The cells of the basal layer are relatively undifferentiated, proliferating cells that serve as a progenitor of the outer layers of the epidermis. The basal cell layer includes, in addition to the basal cells, melanocytes.

The dermis is found under the epidermis, which is separated from the dermis by a basement membrane that consists of interlocking rete ridges and dermal papillae. The dermis itself is composed of two layers, the papillary dermis and the reticular dermis. The dermis consists of fibroblasts, histiocytes, endothelial cells, perivascular macrophages and dendritic cells, mast cells, smooth muscle cells, and cells of peripheral nerves and their end-organ receptors. The dermis also includes fibrous materials such as collagen and reticulin, as well as a ground substance (principally glycosaminoglycans, including hyaluronic acid, chondroitin sulfate, and dermatan sulfate).

Several methods have been proposed to enhance transdermal transport of drugs. For example, chemical enhancers (Burnette, R. R. In *Developmental Issues and Research Initiatives*; Hadgraft J., Ed., Marcel Dekker: 1989; pp. 247–288), iontophoresis, and others have been used. However, in spite of the more than thirty years of research that has gone into delivery of drugs across the skin in particular, fewer than a dozen drugs are now available for transdermal administration in, for example, skin patches.

Transport of drugs and other molecules across the blood-brain barrier is also problematic. The brain capillaries that make up the blood-brain barrier are composed of endothelial cells that form tight junctions between themselves (Goldstein et al., *Scientific American* 255:74–83 (1986); Pardridge, W. M., *Endocrin. Rev.* 7: 314–330 (1986)). The endothelial cells and the tight intercellular junctions that join the cells form a barrier against the passive movement of many molecules from the blood to the brain. The endothelial cells of the blood-brain barrier have few pinocytotic vesicles, which in other tissues can allow somewhat unselective transport across the capillary wall. Nor is the blood-brain barrier interrupted by continuous gaps or channels that run through the cells, thus allowing for unrestrained passage of drugs and other molecules.

Thus, a need exists for improved reagents and methods for enhancing delivery of compounds, including drugs, across epithelial tissues and endothelial tissues such as the skin, the gastrointestinal tract, the eye and the blood-brain barrier. The present invention fulfills this and other needs.

SUMMARY OF THE INVENTION

The present invention provides methods of targeting a compound to a gastrointestinal epithelium of an animal. The methods involve administering to the gastrointestinal epithelium a conjugate that includes the compound and a delivery-enhancing transporter. The delivery-enhancing transporters, which are also provided by the invention, have sufficient guanidino or amidino moieties to increase delivery of the conjugate into the gastrointestinal epithelium or ocular tissues compared to delivery of the compound in the absence of the delivery-enhancing transporter. In some embodiments, delivery of the conjugate into the gastrointestinal epithelium or ocular tissue is increased at least two-fold compared to delivery of the compound in the absence of the delivery-enhancing transporter. In more preferred embodiments, delivery of the conjugate into the gastrointestinal epithelium is increased at least ten-fold compared to delivery of the compound in the absence of the delivery-enhancing transporter. The delivery-enhancing transporter and the compound are typically attached through a linker. In addition, the conjugate can comprise two or more delivery-enhancing transporters linked to the compound.

Typically, the delivery-enhancing transporters comprise fewer than 50 subunits and comprise at least 6 guanidino or amidino moieties. In some embodiments, the subunits are amino acids. In some embodiments, the delivery-enhancing transporters have from 6 to 25 guanidino or amidino moieties, and more preferably between 7 and 15 guanidino moieties and still more preferably, at least six contiguous guanidino and/or amidino moieties. In some embodiments, the delivery-enhancing transporters consist essentially of 5 to 50 subunits, at least 50 of which comprise guanidino or amidino residues. In some of these embodiments, the subunits are natural or non-natural amino acids. For example, in some embodiments, the delivery-enhancing transporter comprises 5 to 25 arginine residues or analogs thereof. For example, the transporter can comprise seven contiguous D-arginines.

In some embodiments, the delivery-enhancing transporter comprises 7–15 arginine residues or analogs of arginine. The delivery-enhancing transporter can have at least one arginine that is a D-arginine and in some embodiments, all arginines are D-arginine. In some embodiments, at least 70% of the amino acids are arginines or arginine analogs. In some embodiments, the delivery-enhancing transporter comprises at least 5 contiguous arginines or arginine analogs. The delivery-enhancing transporters can comprise non-peptide backbones. In addition, in some aspects, the transporter is not attached to an amino acid sequence to which the delivery-enhancing molecule is attached in a naturally occurring protein.

The delivery-enhancing transporters and methods of the invention are useful for delivering drugs, diagnostic agents, and other compounds of interest to the gastrointestinal epithelium. The methods and compositions of the invention can be used not only to deliver the compounds to the particular site of administration, but also provide systemic delivery. In some embodiments, the conjugate is administered bucally or as a suppository. The compounds of the conjugate can be a therapeutic for a disease such as inflammatory bowel disease, colon cancer, ulcerative colitis, gastrointestinal ulcers, constipation and imbalance of salt and water absorption. Thus, the compounds can include immunosuppressives, ascomycins, corticosteroids, laxatives, antibiotics or anti-neoplastic agents. In some aspects of the invention, the compound is targeted to the iliem and/or colon.

The delivery-enhancing transporters and methods of the invention are useful for delivering drugs, diagnostic agents, and other compounds of interest to the eye and other ocular tissues. In some embodiments, the conjugate is administered as eye drops or as an injection. The compounds of the conjugate include therapeutics for a disease such as conjunctivitis, bacterial infections, viral infections, dry eye and glaucoma. Thus, the compounds can include antibacterial compounds, antiviral compounds, cyclosporin, ascomycins and corticosteroids.

As discussed above, the compound to be delivered can be connected to the delivery-enhancing transporter by a linker. In some embodiments, the linker is a releasable linker which releases the compound, in biologically active form, from the delivery-enhancing transporter after the compound has passed into and/or through one or more layers of the epithelial and/or endothelial tissue. In some embodiments, the compound is released from the linker by solvent-mediated cleavage. The conjugate is, in some embodiments, substantially stable at acidic pH but the compound is substantially released from the delivery-enhancing transporter at physiological pH. In some embodiments, the half-life of the conjugate is between 5 minutes and 24 hours upon contact with the skin or other epithelial or endothelial tissue. For example, the half-life can be between 30 minutes and 2 hours upon contact with the skin or other epithelial or endothelial tissue.

Examples of conjugate structures of the invention include those having structures such as 3, 4, or 5, as follows:

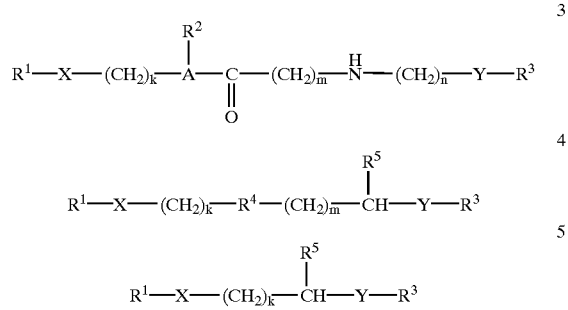

wherein $R^1$ comprises the compound; X is a linkage formed between a functional group on the biologically active compound and a terminal functional group on the linking moiety; Y is a linkage formed from a functional group on the transport moiety and a functional group on the linking moiety; A is N or CH; $R^2$ is hydrogen, alkyl, aryl, acyl, or allyl; $R^3$ comprises the delivery-enhancing transporter; $R^4$ is S, O, $NR^6$ or $CR^7R^8$; $R^5$ is H, OH, SH or $NHR^6$; $R^6$ is hydrogen, alkyl, aryl, acyl or allyl; k and m are each independently selected from 1 and 2; and n 1 is 1 to 10.

Preferably, X is selected from the group consisting of —C(O)O—, —C(O)NH—, —OC(O)NH—, —S—S—, —C(S)O—, —C(S)NH—, —NHC(O)NH—, —SO$_2$NH—, —SONH—, phosphate, phosphonate phosphinate, and CR⁷R⁸, wherein R⁷ and R⁸ are each independently selected from the group consisting of H and alkyl. In some embodiments, $R_4$ is S; $R_5$ is $NHR_6$; and $R_6$ is hydrogen, methyl, allyl, butyl or phenyl. In some embodiments, $R_2$ is benzyl; k, m, and n are each 1, and X is O. In some embodiments, the conjugate comprises structure 3, Y is N, and $R^2$ is methyl, ethyl, propyl, butyl, allyl, benzyl or phenyl. In some embodiments, $R^2$ is benzyl; k, m, and n are each 1, and X is —OC(O)—. In some embodiments, the conjugate comprises structure 4; $R^4$ is S; $R^5$ is $NHR^6$; and $R^6$ is hydrogen, methyl, allyl, butyl or phenyl. In some embodiments, the conjugate comprises structure 4; $R^5$ is $NHR^6$; $R^6$ is hydrogen, methyl, allyl, butyl or phenyl; and k and m are each 1.

The invention also provides conjugates in which the release of the linker from the biological agent involves a first, rate-limiting intramolecular reaction, followed by a faster intramolecular reaction that results in release of the linker. The rate-limiting reaction can, by appropriate choice of substituents of the linker, be made to be stable at a pH that is higher or lower than physiological pH. However, once the conjugate has passed into and across one or more layers of an epithelial or endothelial tissue, the linker will be cleaved from the agent. An example of a compound that has this type of linker is structure 6, as follows:

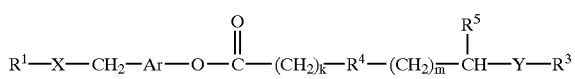

6 wherein $R^1$ comprises the compound; X is a linkage formed between a functional group on the biologically active compound and a terminal functional group on the linking moiety; Y is a linkage formed from a functional group on the transport moiety and a functional group on the linking moiety; Ar is an aryl group having the attached radicals arranged in an ortho or para configuration, which aryl group can be substituted or unsubstituted; $R^3$ comprises the delivery-enhancing transporter; $R^4$ is S, O, $NR^6$ or $CR^7R^8$; $R^5$ is H, OH, SH or $NHR_6$; $R^6$ is hydrogen, alkyl, aryl, arylalkyl, acyl or allyl; $R^7$ and $R^8$ are independently selected from hydrogen or alkyl; and k and m are each independently selected from 1 and 2.

In some embodiments, X is selected from the group consisting of —C(O)O—, —C(O)NH—, —OC(O)NH—, —S—S—, —C(S)O—, —C(S)NH—, —NHC(O)NH—, —SO₂NH—, —SONH—, phosphate, phosphonate phosphinate, and CR⁷R⁸, wherein R⁷ and R⁸ are each independently selected from the group consisting of H and alkyl. In some embodiments, $R^4$ is S; $R^5$ is $NHR^6$; and $R^6$ is hydrogen, methyl, allyl, butyl or phenyl.

In preferred embodiments, the compositions of the invention comprise a linker susceptible to solvent-mediated cleavage. For example, a preferred linker is substantially stable at acidic pH but is substantially cleaved at physiological pH.

BRIEF DESCRIPTION OF THE FIGURES

FIG. 5A shows an example of a disulfide linkage. FIG. 5B shows a photocleavable linker which is cleaved upon exposure to electromagnetic radiation. FIG. 5C shows a modified lysyl residue used as a cleavable linker. FIG. 5D shows a conjugate in which the delivery-enhancing transporter T is linked to the 2'-oxygen of the anticancer agent, paclitaxel. The linking moiety includes (i) a nitrogen atom attached to the delivery-enhancing transporter, (ii) a phosphate monoester located para to the nitrogen atom, and (iii) a carboxymethyl group meta to the nitrogen atom, which is joined to the 2'-oxygen of paclitaxel by a carboxylate ester linkage. FIG. 5E a linkage of a delivery-enhancing transporter to a biologically active agent, e.g., paclitaxel, by an aminoalkyl carboxylic acid; a linker amino group is joined to a delivery-enhancing transporter by an amide linkage and to a paclitaxel moiety by an ester linkage. FIGS. 5F and G show chemical structures and conventional numbering of constituent backbone atoms for paclitaxel and "TAXOTERE™" (R'=H, R"=BOC). FIG. 5G shows the general chemical structure and ring atom numbering for taxoid compounds.

DETAILED DESCRIPTION

Definitions

Figure 1:
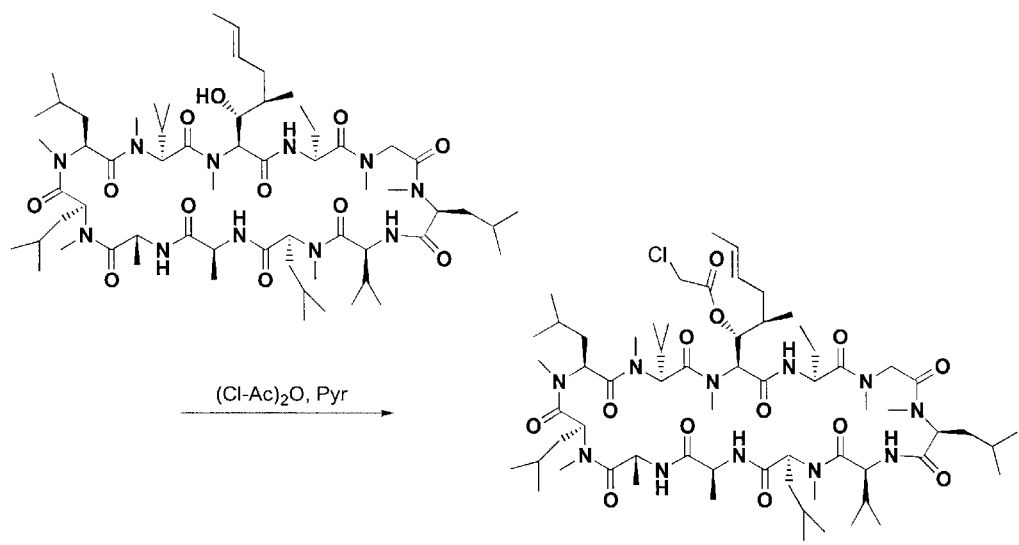
FIG. 1 shows a reaction scheme for the preparation of an α-chloroacetyl cyclosporin A derivative.

An "epithelial tissue" is the basic tissue that covers surface areas of the surface, spaces, and cavities of the body. Epithelial tissues are composed primarily of epithelial cells that are attached to one another and rest on an extracellular matrix (basement membrane) that is typically produced by the cells. Epithelial tissues include three general types based on cell shape: squamous, cuboidal, and columnar epithelium. Squamous epithelium, which lines lungs and blood vessels, is made up of flat cells. Cuboidal epithelium lines kidney tubules and is composed of cube shaped cells, while columnar epithelium cells line the digestive tract and have a columnar appearance. Epithelial tissues can also be classified based on the number of cell layers in the tissue. For example, a simple epithelial tissue is composed of a single layer of cells, each of which sits on the basement membrane. A "stratified" epithelial tissue is composed of several cells stacked upon one another; not all cells contact the basement membrane. A "pseudostratified" epithelial tissue has cells that, although all contact the basement membrane, appear to be stratified because the nuclei are at various levels.

The term "trans-epithelial" delivery or administration refers to the delivery or administration of agents by permeation through one or more layers of a body surface or tissue, such as intact skin or a mucous membrane, by topical administration. Thus, the term is intended to include both transdermal (e.g., percutaneous adsorption) and transmucosal administration. Delivery can be to a deeper layer of the tissue, for example, and/or delivery to the bloodstream.

"Delivery enhancement, "penetration enhancement" or "permeation enhancement" as used herein relates to an increase in amount and/or rate of delivery of a compound that is delivered into and across one or more layers of an epithelial or endothelial tissue. An enhancement of delivery can be observed by measuring the rate and/or amount of the compound that passes through one or more layers of animal or human skin or other tissue. Delivery enhancement also can involve an increase in the depth into the tissue to which the compound is delivered, and/or the extent of delivery to one or more cell types of the epithelial or other tissue (e.g., increased delivery to fibroblasts, immune cells, and endothelial cells of the skin or other tissue). Such measurements are readily obtained by, for example, using a diffusion cell apparatus as described in U.S. Pat. No. 5,891,462.

The amount or rate of delivery of an agent across and/or into skin or other epithelial or endothelial membrane is sometimes quantitated in terms of the amount of compound passing through a predetermined area of skin or other tissue, which is a defined area of intact unbroken living skin or mucosal tissue. That area will usually be in the range of about 5 $cm^2$ to about 100 $cm^2$, more usually in the range of about 10 $cm^2$ to about 100 $cm^2$, still more usually in the range of about 20 $cm^2$ to about 60 $cm^2$.

The terms "guanidyl," guanidinyl" and "guanidino" are used interchangeably to refer to a moiety having the formula —HN=C(NH$_2$)NH (unprotonated form). As an example, arginine contains a guanidyl (guanidino) moiety, and is also referred to as 2-amino-5-guanidinovaleric acid or α-amino-δ-guanidinovaleric acid. "Guanidium" refers to the positively charged conjugate acid form. The term "guanidino moiety" includes, for example, guanidine, guanidinium, guanidine derivatives such as (RNHC(NH)NHR'), mono-substituted guanidines, monoguanides, biguanides, biguanide derivatives such as (RNHC(NH)NHC(NH)NHR'), and the like. In addition, the term "guanidino moiety" encompasses any one or more of a guanide alone or a combination of different guanides.

"Amidinyl" and "amidino" refer to a moiety having the formula —C(=NH)(NH$_2$). "Amidinium" refers to the positively charged conjugate acid form.

The term "trans-barrier concentration" or "trans-tissue concentration" refers to the concentration of a compound present on the side of one or more layers of an epithelial or endothelial barrier tissue that is opposite or "trans" to the side of the tissue to which a particular composition has been added. For example, when a compound is applied to the skin, the amount of the compound measured subsequently across one or more layers of the skin is the trans-barrier concentration of the compound.

"Biologically active agent" or "biologically active substance" refers to a chemical substance, such as a small molecule, macromolecule, or metal ion, that causes an observable change in the structure, function, or composition of a cell upon uptake by the cell. Observable changes include increased or decreased expression of one or more mRNAs, increased or decreased expression of one or more proteins, phosphorylation of a protein or other cell component, inhibition or activation of an enzyme, inhibition or activation of binding between members of a binding pair, an increased or decreased rate of synthesis of a metabolite, increased or decreased cell proliferation, and the like.

The terms "therapeutic agent", "therapeutic composition", and "therapeutic substance" refer, without limitation, to any composition that can be used to the benefit of a mammalian species. Such agents may take the form of ions, small organic molecules, peptides, proteins or polypeptides, oligonucleotides, and oligosaccharides, for example.

The term "macromolecule" as used herein refers to large molecules (MW greater than 1000 daltons) exemplified by, but not limited to, peptides, proteins, oligonucleotides and polynucleotides of biological or synthetic origin.

"Small organic molecule" refers to a carbon-containing agent having a molecular weight (MW) of less than or equal to 1000 daltons.

The terms "non-polypeptide agent" and "non-polypeptide therapeutic agent" refer to the portion of a conjugate that does not include the delivery-enhancing transporter, and that is a biologically active agent other than a polypeptide. An example of a non-polypeptide agent is an anti-sense oligonucleotide, which can be conjugated to a poly-arginine peptide to form a conjugate for enhanced delivery into and across one or more layers of an epithelial or endothelial tissue.

A "subunit," as used herein, is a monomeric unit that are joined to form a larger polymeric compound. The set of amino acids are an example of subunits. Each amino acid shares a common backbone (—C—C—N—), and the different amino acids differ in their sidechains. The backbone is repeated in a polypeptide. A subunit represents the shortest repeating pattern of elements in a polymer backbone. For example, two amino acids of a peptide are not considered a peptide because two amino acids would not have the shortest repeating pattern of elements in the polymer backbone.

The term "polymer" refers to a linear chain of two or more identical or non-identical subunits joined by covalent bonds. A peptide is an example of a polymer; peptides can be composed of identical or non-identical amino acid subunits that are joined by peptide linkages (amide bonds).

The term "peptide" as used herein refers to a compound made up of a single chain of D- or L-amino acids or a mixture of D- and L-amino acids joined by peptide bonds. Generally, peptides contain at least two amino acid residues and are less than about 50 amino acids in length. D-amino acids are represented herein by a lowercase one-letter amino acid symbol (e.g., r for D-arginine), whereas L-amino acids are represented by an upper case one-letter amino acid symbol (e.g., R for L-arginine). Homopolymer peptides are represented by a one-letter amino acid symbol followed by the number of consecutive occurrences of that amino acid in the peptide—(e.g., R7 represents a heptamer that consists of L-arginine residues; SEQ ID NO:3).

The term "protein" as used herein refers to a compound that is composed of linearly arranged amino acids linked by peptide bonds, but in contrast to peptides, has a well-defined conformation. Proteins, as opposed to peptides, generally consist of chains of 50 or more amino acids.

"Polypeptide" as used herein refers to a polymer of at least two amino acid residues and which contains one or more peptide bonds. "Polypeptide" encompasses peptides and proteins, regardless of whether the polypeptide has a well-defined conformation.

Description of the Preferred Embodiments

The present invention provides compositions and methods that enhance the transfer of compounds, including drugs and other biologically active compounds, into and across one or more layers of an animal epithelial or endothelial tissue. The methods involve contacting the tissue with a conjugate that includes the compound of interest linked to a delivery-enhancing transporter. The delivery enhancing transporters provided by the invention are molecules that include sufficient guanidino or amidino moieties to increase delivery of the conjugate into and across one or more intact epithelial and endothelial tissue layers. The methods and compositions are useful for trans-epithelial and trans-endothelial delivery of drugs and other biologically active molecules, and also for delivery of imaging and diagnostic molecules. The methods and compositions of the invention are particularly useful for delivery of compounds that require trans-epithelial or trans-endothelial transport to exhibit their biological effects, and that by themselves (without conjugation to a delivery-enhancing transporters or some other modification), are unable, or only poorly able, to cross such tissues and thus exhibit biological activity.

The delivery-enhancing transporters and methods of the invention provide significant advantages over previously available methods for obtaining trans-epithelial and trans-endothelial tissue delivery of compounds of interest. The transporters make possible the delivery of drugs and other agents across tissues that were previously impenetrable to the drug. For example, while delivery of drugs across skin was previously nearly impossible for all but a few compounds, the methods of the invention can deliver compounds not only into cells of a first layer of an epithelial tissue such as skin, but also across one or more layers of the skin. The blood brain barrier is also resistant to transport of drugs and other diagnostic and therapeutic reagents; the methods and transporters of the invention provide means to obtain such transport.

The delivery-enhancing transporters increase delivery of the conjugate into and across one or more intact epithelial or endothelial tissue layers compared to delivery of the compound in the absence of the delivery-enhancing transporter. The delivery-enhancing transporters can, in some embodiments, increase delivery of the conjugate significantly over that obtained using the tat protein of HIV-1 (Frankel et al. (1991) PCT Pub. No. WO 91/09958). Delivery is also increased significantly over the use of shorter fragments of the tat protein containing the tat basic region (residues 49–57 having the sequence RKKKRRQRRR; SEQ ID NO:28) (Barsoum et al. (1994) WO 94/04686 and Fawell et al. (1994) *Proc. Nat'l. Acad. Sci. USA* 91: 664–668). Preferably, delivery obtained using the transporters of the invention is increased more than 2-fold, still more preferably six-fold, still more preferably ten-fold, and still more preferably twenty-fold, over that obtained with tat residues 49–57.

Similarly, the delivery-enhancing transporters of the invention can provide increased delivery compared to a 16 amino acid peptide-cholesterol conjugate derived from the Antennapedia homeodomain that is rapidly internalized by cultured neurons (Brugidou et al. (1995) *Biochem. Biophys. Res. Commun.* 214: 685–93). This region, residues 43–58 at minimum, has the amino acid sequence RQIKIWFQNR-RMKWKK (SEQ ID NO:29). The Herpes simplex protein VP22, like tat and the Antennapedia domain, was previously known to enhance transport into cells, but was not known to enhance transport into and across endothelial and epithelial membranes (Elliot and O'Hare (1997) *Cell* 88: 223–33; Dilber et al. (1999) *Gene Ther.* 6:12–21; Phelan et al. (1998) *Nature Biotechnol.* 16: 440–3). In presently preferred embodiments, the delivery-enhancing transporters provide significantly increased delivery compared to the Antennapedia homeodomain and to the VP22 protein. In some embodiments, the compositions of the invention do not include the Antennapedia homeodomain, the VP22 protein or eight contiguous arginines (SEQ ID NO:4).

Structure of Delivery-Enhancing Transporters

The delivery-enhancing transporters of the invention are molecules that have sufficient guanidino and/or amidino moieties to increase delivery of a compound to which the delivery-enhancing transporter is attached into and across one or more layers of an epithelial tissue (e.g., skin or mucous membrane) or an endothelial tissue (e.g., the blood-brain barrier). The delivery-enhancing transporters generally include a backbone structure to which is attached the guanidino and/or amidino sidechain moieties. In some embodiments, the backbone is a polymer that consists of subunits (e.g., repeating monomer units), at least some of which subunits contain a guanidino or amidino moiety.

A. Guanidino and/or Amidino Moieties

The delivery-enhancing transporters typically display at least 5 guanidino and/or amidino moieties, and more preferably 7 or more such moieties. Preferably, the delivery-enhancing transporters have 25 or fewer guanidino and/or amidino moieties, and often have 15 or fewer of such moieties. In some embodiments, the delivery-enhancing transporter consists essentially of 50 or fewer subunits, and can consist essentially of 25 or fewer, 20 or fewer, or 15 or fewer subunits. The delivery-enhancing transporter can be as short as 5 subunits, in which case all subunits include a guanidino or amidino sidechain moiety. The delivery-enhancing transporters can have, for example, at least 6 subunits, and in some embodiments have at least 7 or 10 subunits. Generally, at least 50% of the subunits contain a guanidino or amidino sidechain moiety. More preferably, at least 70% of the subunits, and sometimes at least 90% of the subunits in the delivery-enhancing transporter contain a guanidino or amidino sidechain moiety.

Some or all of the guanidino and/or amidino moieties in the delivery-enhancing transporters can be contiguous. For example, the delivery-enhancing transporters can include from 6 to 25 contiguous guanidino and/or amidino-containing subunits. Seven or more contiguous guanidino and/or amidino-containing subunits are present in some embodiments. In some embodiments, each subunit that contains a guanidino moiety is contiguous, as exemplified by a polymer containing at least six contiguous arginine residues.

The delivery-enhancing transporters are exemplified by peptides. Arginine residues or analogs of arginine can constitute the subunits that have a guanidino moiety. Such an arginine-containing peptide can be composed of either all D-, all L- or mixed D- and L-amino acids, and can include additional amino acids, amino acid analogs, or other molecules between the arginine residues. Optionally, the delivery-enhancing transporter can also include a non-arginine residue to which a compound to be delivered is attached, either directly or through a linker. The use of at least one D-arginine in the delivery-enhancing transporters can enhance biological stability of the transporter during transit of the conjugate to its biological target. In some cases the delivery-enhancing transporters are at least about 50% D-arginine residues, and for even greater stability transporters in which all of the subunits are D-arginine residues are used. If the delivery enhancing transporter molecule is a peptide, the transporter is not attached to an amino acid sequence to which the amino acids that make up the delivery enhancing transporter molecule are attached in a naturally occurring protein.

Preferably, the delivery-enhancing transporter is linear. In a preferred embodiment, an agent to be delivered into and across one or more layers of an epithelial tissue is attached to a terminal end of the delivery-enhancing transporter. In some embodiments, the agent is linked to a single transport polymer to form a conjugate. In other embodiments, the conjugate can include more than one delivery-enhancing transporter linked to an agent, or multiple agents linked to a single delivery-enhancing transporter.

More generally, it is preferred that each subunit contains a highly basic sidechain moiety which (i) has a pKa of greater than 11, more preferably 12.5 or greater, and (ii) contains, in its protonated state, at least two geminal amino groups (NH$_2$) which share a resonance-stabilized positive charge, which gives the moiety a bidentate character.

The guanidino or amidino moieties extend away from the backbone by virtue of being linked to the backbone by a sidechain linker. The sidechain atoms are preferably provided as methylene carbon atoms, although one or more other atoms such as oxygen, sulfur or nitrogen can also be present. For example, a linker that attaches a guanidino moiety to a backbone can be shown as:

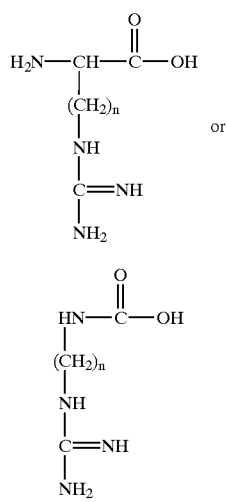

In these formulae, n is preferably at least 2, and is preferably between 2 and 7. In some embodiments, n is 3 (arginine for structure 1). In other embodiments, n is between 4 and 6; most preferably n is 5 or 6. Although the sidechain in the exemplified formulae is shown as being attached to a peptide backbone (i.e., a repeating amide to which the sidechain is attached to the carbon atom that is α to the carbonyl group, subunit 1) and a peptoid backbone (i.e., a repeating amide to which the sidechain is attached to the nitrogen atom that is β to the carbonyl group, subunit 2), other non-peptide backbones are also suitable, as discussed in more detail herein. Thus, similar sidechain linkers can be attached to nonpeptide backbones (e.g., peptoid backbones).

In some embodiments, the delivery-enhancing transporters are composed of linked subunits, at least some of which include a guanidino and/or amidino moiety. Examples of suitable subunits having guanidino and/or amidino moieties are described below.

Amino acids. In some embodiments, the delivery-enhancing transporters are composed of D or L amino acid residues. The amino acids can be naturally occurring or non-naturally occurring amino acids. Arginine (α-amino-δ-guanidinovaleric acid) and α-amino-ε-amidino-hexanoic acid (isosteric amidino analog) are examples of suitable guanidino- and amidino-containing amino acid subunits. The guanidinium group in arginine has a pKa of about 12.5. In some preferred embodiments the transporters are comprised of at least six contiguous arginine residues.

Other amino acids, such as α-amino-β-guanidino-propionic acid, α-amino-γ-guanidino-butyric acid, or α-amino-ε-guanidino-caproic acid (containing 2, 3 or 5 sidechain linker atoms, respectively, between the backbone chain and the central guanidinium carbon) can also be used.

D-amino acids can also be used in the delivery enhancing transporters. Compositions containing exclusively D-amino acids have the advantage of decreased enzymatic degradation. However, they can also remain largely intact within the target cell. Such stability is generally not problematic if the agent is biologically active when the polymer is still attached. For agents that are inactive in conjugate form, a linker that is cleavable at the site of action (e.g., by enzyme- or solvent-mediated cleavage within a cell) should be included within the conjugate to promote release of the agent in cells or organelles.

In addition, the transport moieties are amino acid oligomers of the following formulae: (ZYZ)$_n$Z, (ZY)$_n$Z, (ZYY)$_n$Z and (ZYYY)$_n$Z. See, U.S. patent application Ser. No. 60/269,627, filed Feb. 16, 2001. "Z" in the formulae is D or L-arginine. "Y" is an amino acid that does not contain a guanidyl or amidinyl moiety. The subscript "n" is an integer ran in from 2 to 25.

In the above transport moiety formulae, the letter "Y" represents a natural or non-natural amino acid. The amino acid can be essentially any compound having (prior to incorporation into the transport moiety) an amino group (NH$_2$ or NH-alkyl) and a carboxylic acid group (CO$_2$H) and not containing either a guanidyl or amidinyl moiety. Examples of such compounds include D and L-alanine, D and L-cysteine, D and L-aspartic acid, D and L-glutamic acid, D and L-phenylalanine, glycine, D and L-histidine, D and L-isoleucine, D and L-lysine, D and L-leucine, D and L-methionine, D and L-asparagine, D and L-proline, D and L-glutamine, D and L-serine, D and L-threonine, D and L-valine, D and L-tryptophan, D and L-hydroxyproline, D and L-tyrosine, sarcosine, β-alanine, γ-amino butyric acid and ε-amino caproic acid. In each of the above formulae, each Y will be independent of any other Y present in the transport moiety, though in some embodiments, all Y groups can be the same.

In one group of preferred embodiments, the transport moiety has the formula (ZYZ)$_n$Z (SEQ ID NOS:33–36), wherein each "Y" is independently selected from glycine, β-alanine, γ-amino butyric acid and ε-amino caproic acid, "Z" is preferably L-arginine, and n is preferably an integer ranging from 2 to 5. More preferably, each "Y" is glycine or ε-amino caproic acid and n is 3. Within this group of embodiments, the use of glycine is preferred for those compositions in which the transport moiety is fused or covalently attached directly to a polypeptide biological agent such that the entire composition can be prepared by recombinant methods. For those embodiments in which the transport moiety is to be assembled using, for example, solid phase methods, s-amino caproic acid is preferred.

In another group of preferred embodiments, the transport moiety has the formula $(ZY)_nZ$ (SEQ ID NOS:37–43), wherein each "Y" is preferably selected from glycine, β-alanine, γ-amino butyric acid and ε-amino caproic acid, "Z" is preferably L-arginine, and n is preferably an integer ranging from 4 to 10. More preferably, each "Y" is glycine or ε-amino caproic acid and n is 6. As with the above group of specific embodiments, the use of glycine is preferred for those compositions in which the transport moiety is fused or covalently attached directly to a polypeptide biological agent such that the entire composition can be prepared by recombinant methods. For solution or solid phase construction of the transport moiety, 6-amino caproic acid is preferred.

In yet another group of preferred embodiments, the transport moiety has the formula $(ZYY)_nZ$ (SEQ ID NOS:44–50), wherein each "Y" is preferably selected from glycine, β-alanine, γ-amino butyric acid and ε-amino caproic acid, "Z" is preferably L-arginine, and n is preferably an integer ranging from 4 to 10. More preferably, each "Y" is glycine or ε-amino caproic acid and n is 6.

In still another group of preferred embodiments, the transport moiety has the formula $(ZYYY)_nZ$ (SEQ ID NOS:51–57), wherein each "Y" is preferably selected from glycine, β-alanine, γ-amino butyric acid and ε-amino caproic acid, "Z" is preferably L-arginine, and n is preferably an integer ranging from 4 to 10. More preferably, "Y" is glycine and n is 6.

In other embodiments, each of the Y groups will be selected to enhance certain desired properties of the transport moeity. For example, when transport moeities having a more hydrophobic character are desired, each Y can be selected from those naturally occuring amino acids that are typically grouped together as hydrophobic amino acids (e.g., phenylalanine, phenylglycine, valine, leucine, isoleucine). Similarly, transport moieties having a more hydrophilic character can be prepared when some or all of the Y groups are hydrophilic amino acids (e.g., lysine, serine, threonine, glutamic acid, and the like).

One of skill in the art will appreciate that the transport moiety can be a polypeptide fragment within a larger polypeptide. For example, the transport moiety can be of the formula $(ZYY)_nZ$ yet have additional amino acids which flank this moiety (e.g., $X_m(ZYY)_nZ-X_p$ wherein the subscripts m and p represent integers of zero to about 10 and each X is independently a natural or non-natural amino acid).

Other Subunits. Subunits other than amino acids can also be selected for use in forming transport polymers. Such subunits can include, but are not limited to, hydroxy amino acids, N-methyl-amino acids amino aldehydes, and the like, which result in polymers with reduced peptide bonds. Other subunit types can be used, depending on the nature of the selected backbone, as discussed in the next section.

B. Backbones

The guanidino and/or amidino moieties that are included in the delivery-enhancing transporters are generally attached to a linear backbone. The backbone can comprise a variety of atom types, including carbon, nitrogen, oxygen, sulfur and phosphorus, with the majority of the backbone chain atoms typically consisting of carbon. A plurality of sidechain moieties that include a terminal guanidino or amidino group are attached to the backbone. Although spacing between adjacent sidechain moieties is typically consistent, the delivery-enhancing transporters used in the invention can also include variable spacing between sidechain moieties along the backbone.

A more detailed backbone list includes N-substituted amide (CONR replaces CONH linkages), esters ($CO_2$), keto-methylene ($COCH_2$) reduced or methyleneamino ($CH_2NH$), thioamide (CSNH), phosphinate ($PO_2RCH_2$), phosphonamidate and phosphonamidate ester ($PO_2RNH$), retropeptide (NHCO), trans-alkene (CR=CH), fluoroalkene (CF=CH), dimethylene ($CH_2CH_2$), thioether ($CH_2S$), hydroxyethylene ($CH(OH)CH_2$), methyleneoxy ($CH_2O$), tetrazole ($CN_4$), retrothioamide (NHCS), retroreduced ($NHCH_2$), sulfonamido ($SO_2NH$), methylenesulfonamido ($CHRSO_2NH$), retrosulfonamide ($NHSO_2$), and peptoids (N-substituted amides), and backbones with malonate and/or gem-diamino-alkyl subunits, for example, as reviewed by Fletcher et al. ((1998) *Chem. Rev.* 98:763) and detailed by references cited therein. Many of the foregoing substitutions result in approximately isosteric polymer backbones relative to backbones formed from α-amino acids.

As mentioned above, in a peptoid backbone, the sidechain is attached to the backbone nitrogen atoms rather than the carbon atoms. (See e.g., Kessler (1993) *Angew. Chem. Int. Ed. Engl.* 32:543; Zuckerman et al. (1992) *Chemtracts—Macromol. Chem.* 4:80; and Simon et al. (1992) *Proc. Nat'l. Acad. Sci. USA* 89:9367.) An example of a suitable peptoid backbone is poly-(N-substituted)glycine (poly-NSG). Synthesis of peptoids is described in, for example, U.S. Pat. No. 5,877,278. As the term is used herein, transporters that have a peptoid backbone are considered "non-peptide" transporters, because the transporters are not composed of amino acids having naturally occurring sidechain locations. Non-peptide backbones, including peptoid backbones, provide enhanced biological stability (for example, resistance to enzymatic degradation in vivo).

C. Synthesis of Delivery-Enhancing Transporters

Delivery-enhancing transporters are constructed by any method known in the art. Exemplary peptide polymers can be produced synthetically, preferably using a peptide synthesizer (e.g., an Applied Biosystems Model 433) or can be synthesized recombinantly by methods well known in the art. Recombinant synthesis is generally used when the delivery enhancing transporter is a peptide which is fused to a polypeptide or protein of interest.

N-methyl and hydroxy-amino acids can be substituted for conventional amino acids in solid phase peptide synthesis. However, production of delivery-enhancing transporters with reduced peptide bonds requires synthesis of the dimer of amino acids containing the reduced peptide bond. Such dimers are incorporated into polymers using standard solid phase synthesis procedures. Other synthesis procedures are well known and can be found, for example, in Fletcher et al. (1998) *Chem. Rev.* 98:763, Simon et al. (1992) *Proc. Nat'l. Acad. Sci. USA* 89:9367, and references cited therein.

The delivery-enhancing transporters of the invention can be flanked by one or more non-guanidino/non-amidino subunits (such as glycine, alanine, and cysteine, for example), or a linker (such as an aminocaproic acid group), that do not significantly affect the rate of trans-tissue layer transport of the corresponding delivery-enhancing transporter-containing conjugates. Also, any free amino terminal group can be capped with a blocking group, such as an acetyl or benzyl group, to prevent ubiquitination in vivo.

Where the transporter is a peptoid polymer, one synthetic method involves the following steps: 1) a peptoid polyamine is treated with a base and pyrazole-1-carboxamidine to provide a mixture; 2) the mixture is heated and then allowed to cool; 3) the cooled mixture is acidified; and 4) the acidified mixture is purified. Preferably the base used in step 1 is a carbonate, such as sodium carbonate, and heating step 2 involves heating the mixture to approximately 50° C. for between about 24 hours and about 48 hours. The purification step preferably involves chromatography (e.g., reverse-phase HPLC).

D. Attachment of Transport Polymers to Biologically Active Agents

The agent to be transported can be linked to the delivery-enhancing transporter according to a number of embodiments. In one embodiment, the agent is linked to a single delivery-enhancing transporter, either via linkage to a terminal end of the delivery-enhancing transporter or to an internal subunit within the reagent via a suitable linking group.

In a second embodiment, the agent is attached to more than one delivery-enhancing transporter, in the same manner as above. This embodiment is somewhat less preferred, since it can lead to crosslinking of adjacent cells.

In a third embodiment, the conjugate contains two agent moieties attached to each terminal end of the delivery-enhancing transporter. For this embodiment, it is presently preferred that the agent has a molecular weight of less than 10 kDa.

With regard to the first and third embodiments just mentioned, the agent is generally not attached to one any of the guanidino or amidino sidechains so that they are free to interact with the target membrane.

The conjugates of the invention can be prepared by straightforward synthetic schemes. Furthermore, the conjugate products are usually substantially homogeneous in length and composition, so that they provide greater consistency and reproducibility in their effects than heterogeneous mixtures.

According to an important aspect of the present invention, it has been found by the applicants that attachment of a single delivery-enhancing transporter to any of a variety of types of biologically active agents is sufficient to substantially enhance the rate of uptake of an agent into and across one or more layers of epithelial and endothelial tissues, even without requiring the presence of a large hydrophobic moiety in the conjugate. In fact, attaching a large hydrophobic moiety can significantly impede or prevent cross-layer transport due to adhesion of the hydrophobic moiety to the lipid bilayer of cells that make up the epithelial or endothelial tissue. Accordingly, the present invention includes conjugates that do not contain substantially hydrophobic moieties, such as lipid and fatty acid molecules.

Delivery-enhancing transporters of the invention can be attached covalently to biologically active agents by chemical or recombinant methods.

1. Chemical Linkages

Biologically active agents such as small organic molecules and macromolecules can be linked to delivery-enhancing transporters of the invention via a number of methods known in the art (see, for example, Wong, S. S., Ed., *Chemistry of Protein Conjugation and Cross-Linking*, CRC Press, Inc., Boca Raton, Fla. (1991), either directly (e.g., with a carbodiimide) or via a linking moiety. In particular, carbamate, ester, thioether, disulfide, and hydrazone linkages are generally easy to form and suitable for most applications. Ester and disulfide linkages are preferred if the linkage is to be readily degraded in the cytosol, after transport of the substance across the cell membrane.

Various functional groups (hydroxyl, amino, halogen, etc.) can be used to attach the biologically active agent to the transport polymer. Groups which are not known to be part of an active site of the biologically active agent are preferred, particularly if the polypeptide or any portion thereof is to remain attached to the substance after delivery.

Polymers, such as peptides produced as described in PCT application US98/10571 (Publication No. WO 9852614), are generally produced with an amino terminal protecting group, such as FMOC. For biologically active agents which can survive the conditions used to cleave the polypeptide from the synthesis resin and deprotect the sidechains, the FMOC may be cleaved from the N-terminus of the completed resin-bound polypeptide so that the agent can be linked to the free N-terminal amine. In such cases, the agent to be attached is typically activated by methods well known in the art to produce an active ester or active carbonate moiety effective to form an amide or carbamate linkage, respectively, with the polymer amino group. Of course, other linking chemistries can also be used.

To help minimize side-reactions, guanidino and amidino moieties can be blocked using conventional protecting groups, such as carbobenzyloxy groups (CBZ), di-t-BOC, PMC, Pbf, N—$NO_2$, and the like.

Coupling reactions are performed by known coupling methods in any of an array of solvents, such as N,N-dimethyl formamide (DMF), N-methyl pyrrolidinone, dichloromethane, water, and the like. Exemplary coupling reagents include, for example, O-benzotriazolyloxy tetramethyluronium hexafluorophosphate (HATU), dicyclohexyl carbodiimide, bromo-tris(pyrrolidino) phosphonium bromide (PyBroP), etc. Other reagents can be included, such as N,N-dimethylamino pyridine (DMAP), 4-pyrrolidino pyridine, N-hydroxy succinimide, N-hydroxy benzotriazole, and the like.

2. Fusion Polypeptides

Delivery-enhancing transporters of the invention can be attached to biologically active polypeptide agents by recombinant means by constructing vectors for fusion proteins comprising the polypeptide of interest and the delivery-enhancing transporter, according to methods well known in the art. Generally, the delivery-enhancing transporter component will be attached at the C-terminus or N-terminus of the polypeptide of interest, optionally via a short peptide linker.

3. Releasable Linkers

The biologically active agents are, in presently preferred embodiments, attached to the delivery-enhancing transporter using a linkage that is specifically cleavable or releasable. The use of such linkages is particularly important for biologically active agents that are inactive until the attached delivery-enhancing transporter is released. In some cases, such conjugates that consist of a drug molecule that is attached to a delivery-enhancing transporter can be referred to as prodrugs, in that the release of the delivery-enhancing transporter from the drug results in conversion of the drug from an inactive to an active form. As used herein, "cleaved" or "cleavage" of a conjugate or linker refers to release of a biological agent from a transporter molecule, thereby releasing an active biological agent. "Specifically cleavable" or "specifically releasable" refers to the linkage between the transporter and the agent being cleaved, rather than the transporter being degraded (e.g., by proteolytic degradation).

In some embodiments, the linkage is a readily cleavable linkage, meaning that it is susceptible to cleavage under conditions found in vivo. Thus, upon passing into and through one or more layers of an epithelial and/or endothelial tissue, the agent is released from the delivery-enhancing transporter. Readily cleavable linkages can be, for example, linkages that are cleaved by an enzyme having a specific activity (e.g., an esterase, protease, phosphatase, peptidase, and the like) or by hydrolysis. For this purpose, linkers containing carboxylic acid esters and disulfide bonds are sometimes preferred, where the former groups are hydrolyzed enzymatically or chemically, and the latter are severed by disulfide exchange, e.g., in the presence of glutathione. The linkage can be selected so it is cleavable by an enzymatic activity that is known to be present in one or more layers of an epithelial or endothelial tissue. For example, the stratum granulosum of skin has a relatively high concentration of N-peptidase activity.

A specifically cleavable linker can be engineered onto a transporter molecule. For example, amino acids that constitute a protease recognition site, or other such specifically recognized enzymatic cleavage site, can be used to link the transporter to the agent. Alternatively, chemical or other types of linkers that are cleavable by, for example, exposure to light or other stimulus can be used to link the transporter to the agent of interest.

A conjugate in which an agent to be delivered and a delivery-enhancing transporter are linked by a specifically cleavable or specifically releasable linker will have a half-life. The term "half-life" in this context refers to the amount of time required after applying the conjugate to an epithelial or endothelial membrane for one half of the amount of conjugate to become dissociated to release the free agent. The half-life for some embodiments is typically between 5 minutes and 24 hours, and more preferably is between 30 minutes and 2 hours. The half-life of a conjugate can be "tuned" or modified, according to the invention, as described below.

In some embodiments, the cleavage rate of the linkers is pH dependent. For example, a linker can form a stable linkage between an agent and a delivery-enhancing transporter at an acidic pH (e.g., pH 6.5 or less, more preferably about 6 or less, and still more preferably about 5.5 or less). However, when the conjugate is placed at physiological pH (e.g., pH 7 or greater, preferably about pH 7.4), the linker will undergo cleavage to release the agent. Such pH sensitivity can be obtained by, for example, including a functional group that, when protonated (i.e., at an acidic pH), does not act as a nucleophile. At a higher (e.g., physiological) pH, the functional group is no longer protonated and thus can act as a nucleophile. Examples of suitable functional groups include, for example, N and S. One can use such functional groups to fine-tune the pH at which self-cleavage occurs.

In another embodiment, the linking moiety is cleaved through self-immolation. Such linking moieties in a transport moiety-biologically active compound conjugate contain a nucleophile (e.g., oxygen, nitrogen and sulfur) distal to the biologically active compound and a cleavable group (e.g., ester, carbonate, carbamate and thiocarbamate) proximal to the biologically active compound. Intramolecular attack of the nucleophile on the cleavable group results in the scission of a covalent bond, thereby releasing the linking moiety from the biologically active compound.

Examples of conjugates containing self-immolating linking moieties (e.g., biologically active agent-L-transport moiety conjugates) are represented by structures 3, 4 and 5:

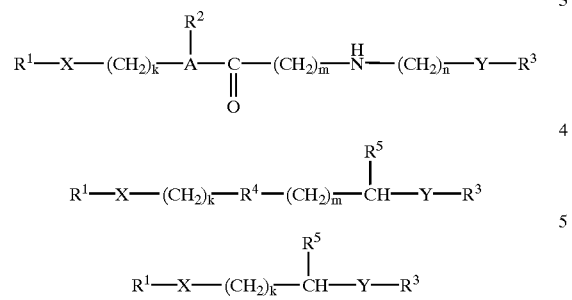

wherein: $R^1$ is the biologically active compound; X is a linkage formed between a functional group on the biologically active compound and a terminal functional group on the linking moiety; Y is a linkage formed from a functional group on the transport moiety and a functional group on the linking moiety; A is N or CH; $R^2$ is hydrogen, alkyl, aryl, arylalkyl, acyl or allyl; $R^3$ is the transport moiety; $R^4$ is S, O, NR or $CR^7R^8$; $R^5$ is H, OH, SH or $NHR^6$; $R^6$ is hydrogen, alkyl, aryl, acyl or allyl; $R^7$ and $R^8$ are independently hydrogen or alkyl; k and m are independently either 1 or 2; and n is an integer ranging from 1 to 10. Non-limiting examples of the X and Y linkages are (in either orientation): —C(O)O—, —C(O)NH—, —OC(O)NH—, —S—S—, —C(S)O—, —C(S)NH—, —NHC(O)NH—, —SO$_2$NH—, —SONH—, phosphate, phosphonate and phosphinate. One of skill in the art will appreciate that when the biological agent has a hydroxy functional group, then X will preferably be —OC(O)— or —OC(O)NH—. Similarly, when the linking group is attached to an amino terminus of the transport moiety, Y will preferably be —C(O)NH—, —NHC(O)NH—, —SO$_2$NH—, —SONH— or —OC(O)NH— and the like. In each of the groups provided above, NH is shown for brevity, but each of the linkages (X and Y) can contain substituted (e.g., N-alkyl or N-acyl) linkages as well.

Figure 6:
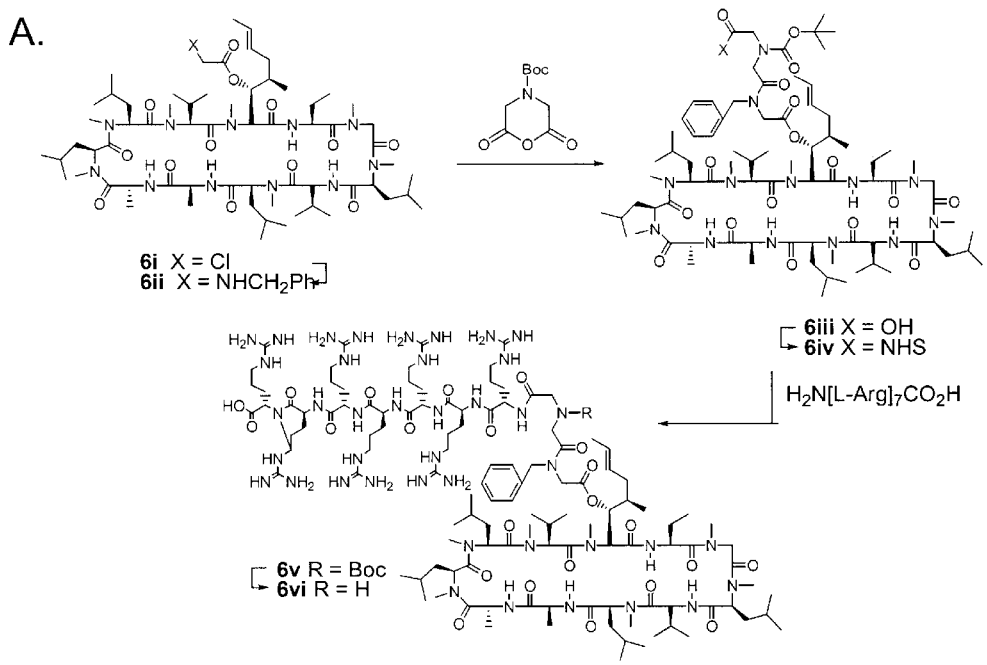
FIG. 6 displays a synthetic scheme for a chemical conjugate between a heptamer of L-arginine (SEQ ID NO:3) and cyclosporin A (panel A) and its pH dependent chemical release (SEQ ID NO:6) (panel B). The α-chloro ester (2) was treated with benzylamine in the presence of sodium iodide to effect substitution, giving the secondary amine (5). Amine (5) was treated with anhydride (6) and the resultant crude acid (7) was converted to its corresponding NHS ester (8). Ester (8) was then coupled with the amino terminus of hepta-L-arginine (SEQ ID NO:3), giving the N-Boc protected CsA conjugate (9). Finally, removal of the Boc protecting group with formic acid afforded the conjugate (10) as its octatrifluoroacetate salt after HPLC purification.
Figure 6:
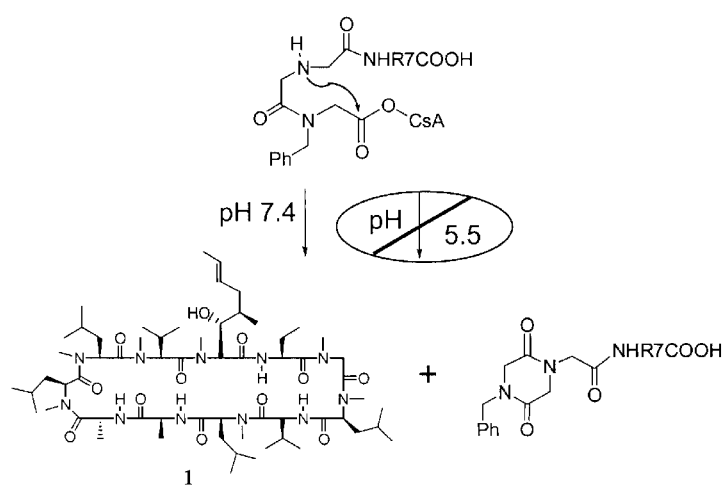

Turning first to linking groups illustrated by structure 3, an example and preferred embodiment is illustrated for formula 3a:

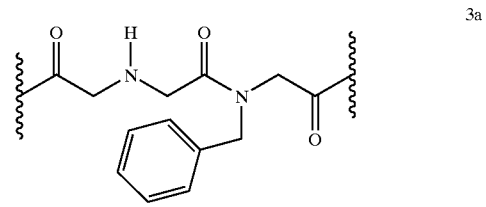

wherein the wavy lines indicate points of attachment to the transport moiety and to the biologically active compound. Preparation of a conjugate containing this linking group is illustrated in Example 20 (FIG. 6). In this Example and FIG. 6, cyclosporin A is treated with chloroacetic anhydride to form the chloroacetate ester 6i (numbering in FIG. 6) which is then combined with benzylamine to form the N-benzyl glycine conjugate 6ii. Condensation of the glycine conjugate with Boc-protected diglycine anhydride provides the acid 6iii which is converted to the more reactive N-hydroxy succinimide ester 6iv and then combined with the amino terminus of a transport moiety to form an amide linkage. One of skill in the art will appreciate that the N-benzyl group can be replaced with other groups (e.g., alkyl, aryl, allyl and the like) or that methylene groups can be replaced with, for example, ethylene, propylene and the like. Preferably, the methylene groups are retained as shown in 3a, to provide an appropriate steric or spatial orientation that allows the linkage to be cleaved in vivo (see FIG. 6B).

Accordingly, for structure 3, the following substituents are preferred: A is N; $R^2$ is benzyl; k, m and n are 1; X is —OC(O)— and Y is —C(O)NH—.

Linkages of structure 4, are exemplified by formula 4a:

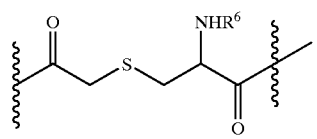

Figure 39:
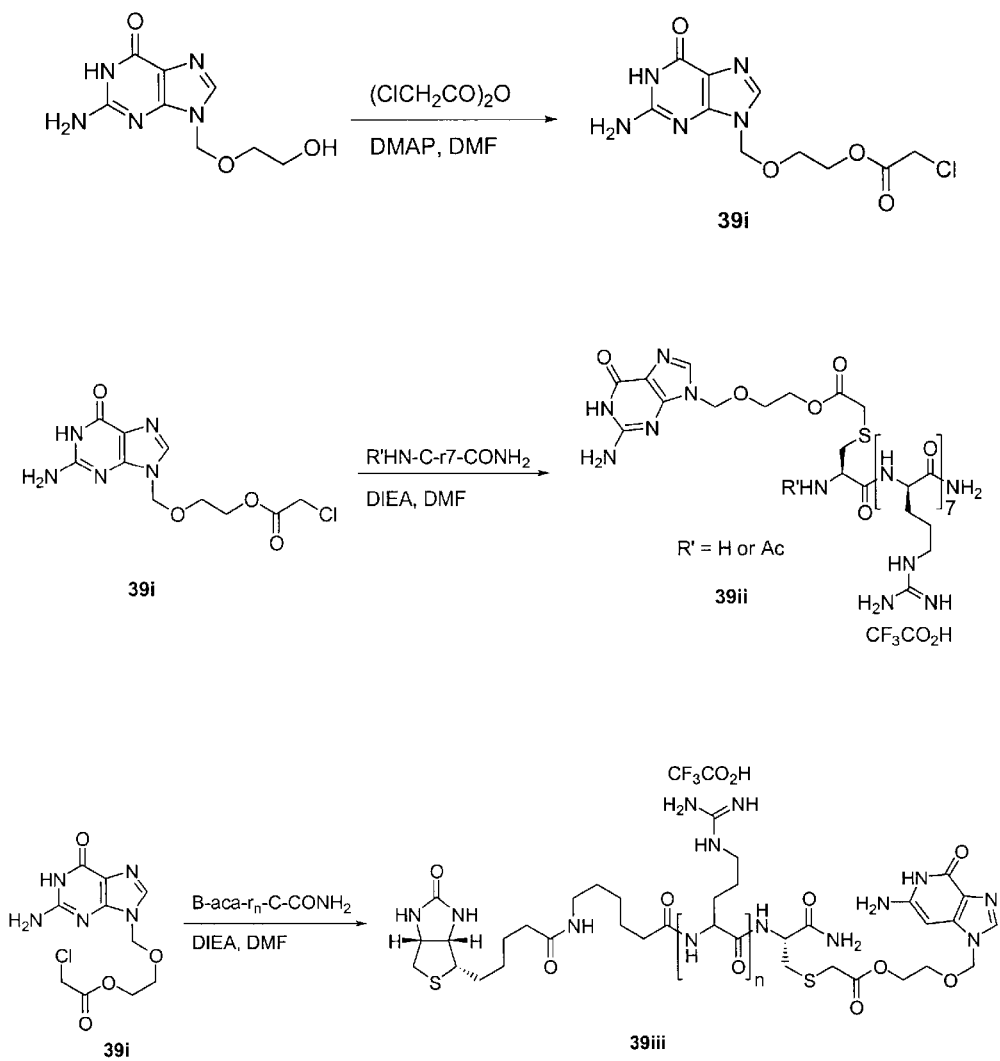
FIG. 39 illustrates the conjugation of acyclovir to r7-amide via an N-terminal cysteine group. Conjugation with a biotin-containing transporter is also shown.

4a wherein, as above, the wavy lines indicate the point of attachment to each of the transport moiety and the biologically active agent. The preparation of conjugates having linking groups of formula 4a are shown in Examples 20–22. In Example 20 (see scheme in FIG. 39), acyclovir is acylated with α-chloroacetic anhydride to form the α-chloroacetate ester 39i. Reaction of 39i with a heptamer of D-arginine having an N-terminal cysteine residue, provides the thioether product 39ii. Alternatively, acyclovir can be attached to the C-terminus of a transport moiety using a similar linkage formed between acyclovir α-chloroacetate ester and a heptamer of D-arginine having an C-terminal cysteine residue. In this instance, the cysteine residue is provided on the $r_7$ transport moiety as a C-terminal amide and the linkage has the form:

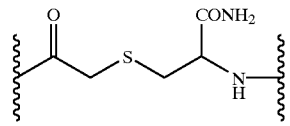

Accordingly, in one group of preferred embodiments, the conjugate is represented by formula 5, in which X is —OC(O)—; Y is —C(O)NH—; $R^4$ is S; $R^5$ is $NHR^6$; and the subscripts k and m are each 1. In another group of preferred embodiments, the conjugate is represented by formula 2, in which X is —OC(O)—; Y is —NHC(O)—; $R^4$ is S; $R^5$ is $CONH_2$; and the subscripts k and m are each 1. Particularly preferred conjugates are those in which $R^6$ is hydrogen, methyl, allyl, butyl or phenyl.

Linking groups represented by the conjugates shown in formula 6 are generally of the heterobifunctional type (e.g., ε-aminocaproic acid, serine, homoserine, γ-aminobutyric acid, and the like), although suitably protected dicarboxylic acids or diamines are also useful with certain biological agents.

For structure 6, the following substituents are preferred: $R^5$ is $NHR^6$, wherein $R^6$ is hydrogen, methyl, allyl, butyl or phenyl; k is 2; X is —C(O)O—; and Y is —C(O)NH—.

Self-immolating linkers typically undergo intramolecular cleavage with a half-life between about 10 minutes and about 24 hours in water at 37° C. at a pH of approximately 7.4. Preferably, the cleavage half-life is between about 20 minutes and about 4 hours in water at 37° C. at a pH of approximately 7.4. More preferably, the cleavage half-life is between about 30 minutes and about 2 hours in water at 37° C. at a pH of approximately 7.4.

For a conjugate having the structure 3, one can adjust the cleavage half-life by varying the $R^2$ substituent. By using an $R^2$ of increased or decreased size, one can obtain a conjugate having a longer or shorter half-life respectively. $R^2$ in structure 3 is preferably methyl, ethyl, propyl, butyl, allyl, benzyl or phenyl.

Where there is a basic or acidic group in a self-immolating linker, one can oftentimes adjust cleavage half-life according to the pH of the conjugate solution. For instance, the backbone amine group of structure 3 is protonated at acidic pH (e.g., pH 5.5). The amine cannot serve as a nucleophile inducing intramolecular cleavage when it is protonated. Upon introduction of the conjugate into a medium at physiological pH (7.4), however, the amine is unprotonated a significant portion of the time. The cleavage half-life is correspondingly reduced.

In one embodiment, cleavage of a self-immolating linker occurs in two steps: intramolecular reaction of a nucleophilic group resulting in the cleavage of a portion of the linking moiety; and, elimination of the remaining portion of the linking moiety. The first step of the cleavage is rate-limiting and can be fine-tuned for pH sensitivity and half-life.

Structure 6 is an example of a two-step, self-immolating moiety that is incorporated into a transport moiety-biologically active compound conjugate:

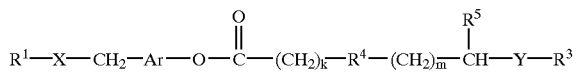

6 wherein: $R^1$ is the biologically active compound; X represents a linkage between a functional group on the biologically active compound and a functional group on the linking moiety; Ar is a substituted or unsubstituted aryl group, wherein the methylene substituent and phenolic oxygen atom are either ortho or para to one another; $R^3$ is the transport moiety; $R^4$ is S, O, $NR^6$ or $CR^7R^8$; $R^5$ is H, OH, SH or $NHR^6$; $R^6$ is hydrogen, alkyl, aryl, arylalkyl, acyl or allyl; $R^7$ and $R^8$ are independently hydrogen or alkyl; and, k and m are independently either 1 or 2.

An example of a suitable linking group to produce a conjugate of formula 6 is:

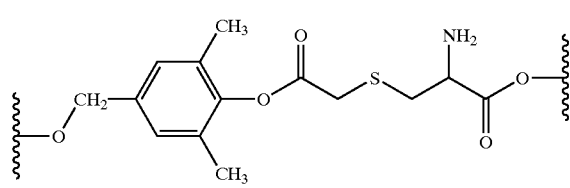

6a

Figure 14:
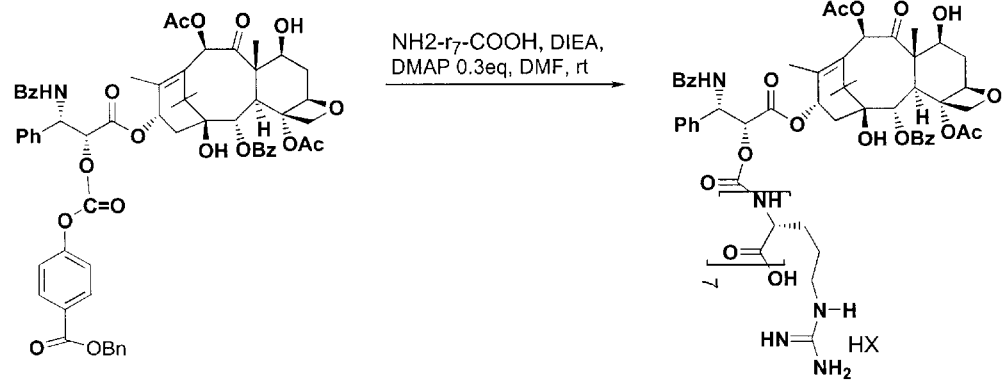
FIG. 14 shows a reaction for coupling of an unlabeled peptide to a C-2' derivative of taxol.

The construction of a conjugate containing a linking group of formula 6a is provided in Example 24 (see also FIG. 14). In this example (and Figure), the α-chloroacetate ester of 2,4-dimethyl-4-hydroxymethylphenol (41i) is coupled to retinoic acid (41ii) using dicyclohexylcarbodiimide (DCC) and 4-dimethylaminopyridine (DMAP) to provide the intermediate 41iii. Subsequent coupling of 41iii with a cysteine residue present on the N-terminus of an arginine heptamer transport moiety provides the target conjugate 41iv.

Preferably, the linking groups used in the conjugates of formula 6, are those in which Ar is an substituted or unsubstituted phenylene group; $R^4$ is S; $R^5$ is $NHR^6$, wherein $R^6$ is hydrogen, methyl, allyl, butyl, acetyl or phenyl; k and m are 1; X is —C(O)O—; and Y is —C(O) O— or —C(O)NH—. More preferably, $R^6$ is hydrogen or acetyl.

While linking groups above have been described with reference to conjugates containing arginine heptamers, one of skill in the art will understand that the technology is readily adapted to conjugates with the "spaced" arginine transport moieties of the present invention.

Still other useful linking groups for use in the present invention have been described in copending PCT applications. See, for example PCT applications US98/10571 (Publication No. WO 9852614) and US00/23440 (Publication No. WO 01/13957) which describe linking groups for similar compositions, e.g., conjugates of biologically active agents and transport oligomers. The linking technology described therein can be used in the present compositions in a similar manner.

Thus, in one group of embodiments, the linking moiety contains a first cleavable group distal to the biologically active compound and a second cleavable group proximal to the biologically active compound. Cleavage of the first cleavable group yields a nucleophile capable of reacting intramolecularly with the second cleavable group, thereby cleaving the linking moiety from the biologically active compound. Examples of methods by which the first group is cleaved include photo-illumination and enzyme mediated hydrolysis. This methodology has been illustrated for various related small molecule conjugates discussed in PCT application US98/10571 (Publication No. WO 9852614).

Figure 5A:
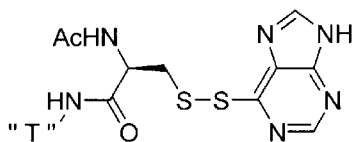
FIGS. 5A–H show various types of cleavable linkers that can be used to link a delivery-enhancing transporter to a biologically active agent or other molecule of interest.

In one approach, the conjugate can include a disulfide linkage, as illustrated in FIG. 5A of PCT application US00/23440 (Publication No. WO 01/13957), (see also, PCT application US98/10571 (Publication No. WO 9852614)), which shows a conjugate (I) containing a transport polymer T which is linked to a cytotoxic agent, 6-mercaptopurine, by an N-acetyl-protected cysteine group which serves as a linker. Thus, the cytotoxic agent is attached by a disulfide bond to the 6-mercapto group, and the transport polymer is bound to the cysteine carbonyl moiety via an amide linkage. Cleavage of the disulfide bond by reduction or disulfide exchange results in release of the free cytotoxic agent. A method for synthesizing a disulfide-containing conjugate is provided in Example 9A of PCT application US98/10571. The product described therein contains a heptamer of Arg residues which is linked to 6-mercaptopurine by an N-acetyl-Cys-Ala-Ala linker, where the Ala residues are included as an additional spacer to render the disulfide more accessible to thiols and reducing agents for cleavage within a cell. The linker in this example also illustrates the use of amide bonds, which can be cleaved enzymatically within a cell.

Figure 5B:
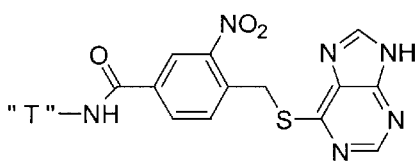

In another approach, the conjugate includes a photocleavable linker that is cleaved upon exposure to electromagnetic radiation. Application of this methodology is provided for a related system in FIG. 5B of PCT application US00/23440 (Publication No. WO 01/13957) which shows a conjugate (II) containing a transport polymer T which is linked to 6-mercaptopurine via a meta-nitrobenzoate linking moiety. Polymer T is linked to the nitrobenzoate moiety by an amide linkage to the benzoate carbonyl group, and the cytotoxic agent is bound via its 6-mercapto group to the p-methylene group. The compound can be formed by reacting 6-mercaptopurine with p-bromomethyl-m-nitrobenzoic acid in the presence of $NaOCH_3$/methanol with heating, followed by coupling of the benzoate carboxylic acid to a transport polymer, such as the amino group of a γ-aminobutyric acid linker attached to the polymer (see also, e.g., Example 9B of PCT application US98/10571). Photo-illumination of the conjugate causes release of the 6-mercaptopurine by virtue of the nitro group that is ortho to the mercaptomethyl moiety. This approach finds utility in phototherapy methods as are known in the art, particularly for localizing drug activation to a selected area of the body.

In one group of preferred embodiments, the cleavable linker contains first and second cleavable groups that can cooperate to cleave the oligomer from the biologically active agent, as illustrated by the following approaches. That is, the cleavable linker contains a first cleavable group that is distal to the agent, and a second cleavable group that is proximal to the agent, such that cleavage of the first cleavable group yields a linker-agent conjugate containing a nucleophilic moiety capable of reacting intramolecularly to cleave the second cleavable group, thereby releasing the agent from the linker and oligomer.

Figure 5C:
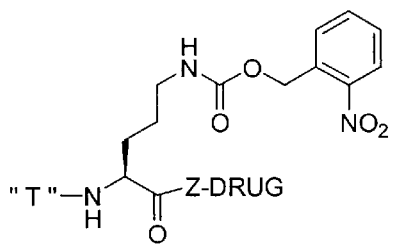

Reference is again made to co-owned and copending PCT application US00/23440 (Publication No. WO 01/13957), in which FIG. 5C shows a conjugate (III) containing a transport polymer T linked to the anticancer agent, 5-fluorouracil (5FU). In that figure, the linkage is provided by a modified lysyl residue. The transport polymer is linked to the α-amino group, and the 5-fluorouracil is linked via the α-carbonyl. The lysyl ε-amino group has been modified to a carbamate ester of o-hydroxymethyl nitrobenzene, which comprises a first, photolabile cleavable group in the conjugate. Photo-illumination severs the nitrobenzene moiety from the conjugate, leaving a carbamate that also rapidly decomposes to give the free α-amino group, an effective nucleophile. Intramolecular reaction of the α-amino group with the amide linkage to the 5-fluorouracil group leads to cyclization with release of the 5-fluorouracil group.

Still other linkers useful in the present invention are provided in PCT application US00/23440 (Publication No. WO 01/13957). In particular, FIG. 5D of US00/23440 illustrates a conjugate (IV) containing a delivery-enhancing transporter T linked to 2'-oxygen of the anticancer agent, paclitaxel. The linkage is provided by a linking moiety that includes (i) a nitrogen atom attached to the delivery-enhancing transporter, (ii) a phosphate monoester located para to the nitrogen atom, and (iii) a carboxymethyl group meta to the nitrogen atom, which is joined to the 2'-oxygen of paclitaxel by a carboxylate ester linkage. Enzymatic cleavage of the phosphate group from the conjugate affords a free phenol hydroxyl group. This nucleophilic group then reacts intramolecularly with the carboxylate ester to release free paclitaxel, fully capable of binding to its biological target. Example 9C of PCT application US98/10571 describes a synthetic protocol for preparing this type of conjugate.

Figure 5D:
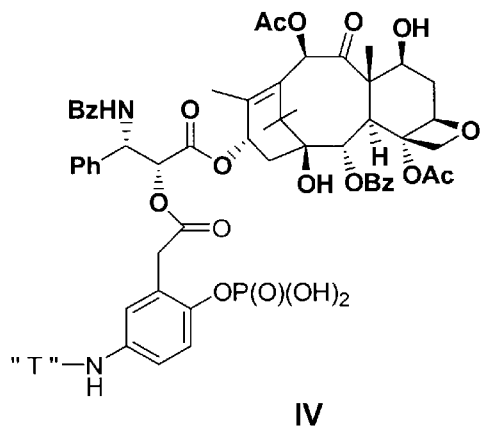
Figure 5E:
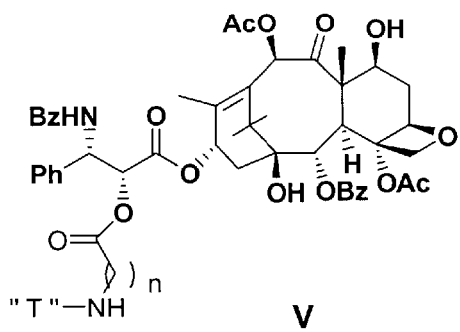

Still other suitable linkers are illustrated in FIG. 5E of PCT application US00/23440 (Publication No. WO 01/13957). In the approach provided therein, a delivery-enhancing transporter is linked to a biologically active agent, e.g., paclitaxel, by an aminoalkyl carboxylic acid. Preferably, the linker amino group is linked to the linker carboxyl carbon by from 3 to 5 chain atoms (n=3 to 5), preferably either 3 or 4 chain atoms, which are preferably provided as methylene carbons. As seen in FIG. 5E, the linker amino group is joined to the delivery-enhancing transporter by an amide linkage, and is joined to the paclitaxel moiety by an ester linkage. Enzymatic cleavage of the amide linkage releases the delivery-enhancing transporter and produces a free nucleophilic amino group. The free amino group can then react intramolecularly with the ester group to release the linker from the paclitaxel.

In another approach, the conjugate includes a linker that is labile at one pH but is stable at another pH. For example, FIG. 6 of PCT application US00/23440 (Publication No. WO 01/13957) illustrates a method of synthesizing a conjugate with a linker that is cleaved at physiological pH but is stable at acidic pH. Preferably, the linker is cleaved in water at a pH of from about 6.6 to about 7.6. Preferably the linker is stable in water at a pH from about 4.5 to about 6.5.

Uses of Delivery-Enhancing Transporters

The delivery-enhancing transporters find use in therapeutic, prophylactic and diagnostic applications. The delivery-enhancing transporters can carry a diagnostic or biologically active reagent into and across one or more layers of skin or other epithelial tissue (e.g., gastrointestinal, lung, ocular and the like), or across endothelial tissues such as the blood brain barrier. This property makes the reagents useful for treating conditions by delivering agents that must penetrate across one or more tissue layers in order to exert their biological effect.

Moreover, the transporters of the present invention can also be used alone, or in combination with another therapeutic or other compound, as a furin inhibitor. For example, in addition to various poly-arginine transporters, the synthetic transporters described herein, including peptoid and those transporters comprising non-naturally occurring amino acids can be used to inhibit furins. See, e.g., Cameron et al., *J. Biol. Chem.* 275(47): Furins are proteases that convert a variety of pro-proteins to their active components. Inhibition of furins is useful, for instance, for treating infections by viruses that rely on furin activity for virulence or replication. See, e.g., Molloy, et al., *T. Cell Biol.* 9:28–35 (1999).

Similarly, the transporters of the invention are useful inhibitors of capthesin C. For example, certain poly arginine compounds are inhibitors of capthesin C. See, e.g., Horn, et al., *Eur. J. Biochem.* 267(11):3330–3336 (2000). Similarly, the transporters of the invention, including those comprising synthetic amino acids, are useful to inhibit capthesin C.

In one aspect of the invention, a furin inhibition assay can be used to screen for additional transporters. For example, candidate transporter compounds can be tested for their ability to compete with poly arginine for their ability to bind furins or capthesin C using standard competition assays. Alternatively, candidate transporters can be screened for their ability to inhibit furin protease activity as discussed in Cameron et al., supra. and Horn et al., supra. Particularly active candidates can then be further tested for their ability to act as transporters into and/or across tissues such as the epithelium.

Compositions and methods of the present invention have particular utility in the area of human and veterinary therapeutics. Generally, administered dosages will be effective to deliver picomolar to micromolar concentrations of the therapeutic composition to the effector site. Appropriate dosages and concentrations will depend on factors such as the therapeutic composition or drug, the site of intended delivery, and the route of administration, all of which can be derived empirically according to methods well known in the art. Further guidance can be obtained from studies using experimental animal models for evaluating dosage, as are known in the art.

Administration of the compounds of the invention with a suitable pharmaceutical excipient as necessary can be carried out via any of the accepted modes of administration. Thus, administration can be, for example, intravenous, topical, subcutaneous, transcutaneous, intramuscular, oral, intra-joint, parenteral, peritoneal, intranasal, or by inhalation. Suitable sites of administration thus include, but are not limited to, skin, bronchial, gastrointestinal, anal, vaginal, eye, and ear. The formulations may take the form of solid, semi-solid, lyophilized powder, or liquid dosage forms, such as, for example, tablets, pills, capsules, powders, solutions, suspensions, emulsions, suppositories, retention enemas, creams, ointments, lotions, aerosols, eye drops, or the like, preferably in unit dosage forms suitable for simple administration of precise dosages.

The compositions typically include a conventional pharmaceutical carrier or excipient and may additionally include other medicinal agents, carriers, adjuvants, and the like. Preferably, the composition will be about 5% to 75% by weight of a compound or compounds of the invention, with the remainder consisting of suitable pharmaceutical excipients. Appropriate excipients can be tailored to the particular composition and route of administration by methods well known in the art, e.g., *REMINGTON'S PHARMACEUTICAL SCIENCES,* 18TH ED., Mack Publishing Co., Easton, Pa. (1990).

For oral administration, such excipients include pharmaceutical grades of mannitol, lactose, starch, magnesium stearate, sodium saccharine, talcum, cellulose, glucose, gelatin, sucrose, magnesium carbonate, and the like. The composition may take the form of a solution, suspension, tablet, pill, capsule, powder, sustained-release formulation, and the like.

In some embodiments, the pharmaceutical compositions take the form of a pill, tablet or capsule, and thus, the composition can contain, along with the biologically active conjugate, any of the following: a diluent such as lactose, sucrose, dicalcium phosphate, and the like; a disintegrant such as starch or derivatives thereof; a lubricant such as magnesium stearate and the like; and a binder such a starch, gum acacia, polyvinylpyrrolidone, gelatin, cellulose and derivatives thereof.

The active compounds of the formulas may be formulated into a suppository comprising, for example, about 0.5% to about 50% of a compound of the invention, disposed in a polyethylene glycol (PEG) carrier (e.g., PEG 1000 [96%] and PEG 4000 [4%]).

Liquid compositions can be prepared by dissolving or dispersing compound (about 0.5% to about 20%), and optional pharmaceutical adjuvants in a carrier, such as, for example, aqueous saline (e.g., 0.9% w/v sodium chloride), aqueous dextrose, glycerol, ethanol and the like, to form a solution or suspension, e.g., for intravenous administration. The active compounds may also be formulated into a retention enema.

If desired, the composition to be administered may also contain minor amounts of non-toxic auxiliary substances such as wetting or emulsifying agents, pH buffering agents, such as, for example, sodium acetate, sorbitan monolaurate, or triethanolamine oleate.

For topical administration, the composition is administered in any suitable format, such as a lotion or a transdermal patch. For delivery by inhalation, the composition can be delivered as a dry powder (e.g., Inhale Therapeutics) or in liquid form via a nebulizer.

Methods for preparing such dosage forms are known or will be apparent to those skilled in the art; for example, see *Remington's Pharmaceutical Sciences,* supra., and similar publications. The composition to be administered will, in any event, contain a quantity of the pro-drug and/or active compound(s) in a pharmaceutically effective amount for relief of the condition being treated when administered in accordance with the teachings of this invention.

Generally, the compounds of the invention are administered in a therapeutically effective amount, i.e., a dosage sufficient to effect treatment, which will vary depending on the individual and condition being treated. Typically, a therapeutically effective daily dose is from 0.1 to 100 mg/kg of body weight per day of drug. Most conditions respond to administration of a total dosage of between about 1 and about 30 mg/kg of body weight per day, or between about 70 mg and 2100 mg per day for a 70 kg person.

Stability of the conjugate can be further controlled by the composition and stereochemistry of the backbone and sidechains of the delivery-enhancing transporters. For polypeptide delivery-enhancing transporters, D-isomers are generally resistant to endogenous proteases, and therefore have longer half-lives in serum and within cells. D-polypeptide polymers are therefore appropriate when longer duration of action is desired. L-polypeptide polymers have shorter half-lives due to their susceptibility to proteases, and are therefore chosen to impart shorter acting effects. This allows side-effects to be averted more readily by withdrawing therapy as soon as side-effects are observed. Polypeptides comprising mixtures of D and L-residues have intermediate stabilities. Homo-D-polymers are generally preferred.

A. Application to Skin

The delivery-enhancing transporters of the invention make possible the delivery of biologically active and diagnostic agents across the skin. Surprisingly, the transporters can deliver an agent across the stratum corneum, which previously had been a nearly impenetrable barrier to drug delivery. The stratum corneum, the outermost layer of the skin, is composed of several layers of dead, keratin-filled skin cells that are tightly bound together by a "glue" composed of cholesterol and fatty acids. Once the agents are delivered through the stratum corneum by the transporters of the invention, the agents can enter the viable epidermis, which is composed of the stratum granulosum, stratum lucidum and stratum germinativum which, along with the stratum corneum, make up the epidermis. Delivery in some embodiments of the invention is through the epidermis and into the dermis, including one or both of the papillary dermis and the reticular dermis.

This ability to obtain penetration of one or more layers of the skin can greatly enhance the efficacy of compounds such as antibacterials, antifungals, antivirals, antiproliferatives, immunosuppressives, vitamins, analgesics, hormones, and the like. Numerous such compounds are known to those of skill in the art (see, e.g., Hardman and Limbird, *Goodman & Gilman's The Pharmacological Basis of Therapeutics*, McGraw-Hill, New York, 1996).

In some embodiments, the agent is delivered into a blood vessel that is present in the epithelial tissue, thus providing a means for delivery of the agent systemically. Delivery can be either intrafollicular or interfollicular, or both. Pretreatment of the skin is not required for delivery of the conjugates.

In other embodiments, the delivery-enhancing transporters are useful for delivering cosmetics and agents that can treat skin conditions. Target cells in the skin that are of interest include, for example, fibroblasts, epithelial cells and immune cells. For example, the transporters provide the ability to deliver compounds such as antiinflammatory agents to immune cells found in the dermis.

Glucocorticoids (adrenocorticoid steroids) are among the compounds for which delivery across skin can be enhanced by the delivery-enhancing transporters of the invention. Conjugated glucocorticoids of the invention are useful for treating inflammatory skin diseases, for example. Exemplary glucocorticoids include, e.g., hydrocortisone, prenisone (deltasone) and predrisonlone (hydeltasol). Examples of particular conditions include eczema (including atopic dermatitis, contact dermatitis, allergic dermatitis), bullous disease, collagen vascular diseases, sarcoidosis, Sweet's disease, pyoderma gangrenosum, Type I reactive leprosy, capillary hemangiomas, lichen planus, exfoliative dermatitis, erythema nodosum, hormonal abnormalities (including acne and hirsutism), as well as toxic epidermal necrolysis, erythema multiforme, cutaneous T-cell lymphoma, discoid lupus erythematosus, and the like.

Retinoids are another example of a biologically active agent for which one can use the delivery-enhancing transporters of the invention to enhance delivery into and across one or more layers of the skin or other epithelial or endothelial tissue. Retinoids that are presently in use include, for example retinol, tretinoin, isotretinoin, etretinate, acitretin, and arotinoid. Conditions that are treatable using retinoids conjugated to the delivery-enhancing transporters of the invention include, but are not limited to, acne, keratinization disorders, skin cancer, precancerous conditions, psoriasis, cutaneous aging, discoid lupus erythematosus, scleromyxedema, verrucous epidermal nevus, subcorneal pustular dermatosis, Reiter's syndrome, warts, lichen planus, acanthosis nigricans, sarcoidosis, Grover's disease, porokeratosis, and the like.

Cytotoxic and immunosuppressive drugs constitute an additional class of drugs for which the delivery-enhancing transporters of the invention are useful. These agents are commonly used to treat hyperproliferative diseases such as psoriasis, as well as for immune diseases such as bullous dermatoses and leukocytoclastic vasculitis. Examples of such compounds that one can conjugate to the delivery-enhancing transporters of the invention include, but are not limited to, antimetabolites and alkylating agents. Useful biological agents include, e.g., methotrexate, azathioprine, fluorouracil, hydroxyurea, 6-thioquanine, mycophenolate, chlorambucil, vinicristine, vinblasrine, dactinomycin, cyclophosphamide, mechioroethamine hydrochloride, carmustine, taxol, tacrolimus, vinbiastine, dapsone and sulfasalazine. Immunosuppressive drugs such as cyclosporin and Ascomycins, such as FK506 (tacrolimus) and rapamycin (e.g., U.S. Pat. No. 5,912,253) and analogs of such compounds are of particular interest (e.g., Mollinson et al., *Current Pharm. Design* 4(5):367–380 (1998); U.S. Pat. Nos. 5,612,350; 5,599,927; 5,604,294; 5,990,131; 5,561,140; 5,859,031; 5,925,649; 5,994,299; 6,004,973 and 5,508,397). Cyclosporins include cyclosporin A, B, C, D, G and M. See, e.g., U.S. Pat. Nos. 6,007,840; and 6,004,973. For example, such compounds are useful in treating psoriasis, eczema (including atopic dermatitis, contact dermatitis, allergic dermatitis) and alopecia areata.

The delivery-enhancing transporters can be conjugated to agents that are useful for treating conditions such as lupus erythematosus (both discoid and systemic), cutaneous dermatomyositis, porphyria cutanea tarda and polymorphous light eruption. Agents useful for treating such conditions include, for example, quinine, chloroquine, hydroxychloroquine, and quinacrine.

The delivery-enhancing transporters of the invention are also useful for transdermal delivery of antiinfective agents. For example, antibacterial, antifungal and antiviral agents can be conjugated to the delivery-enhancing transporters. Antibacterial agents are useful for treating conditions such as acne, cutaneous infections, and the like. Antifungal agents can be used to treat tinea corporis, tinea pedis, onychomycosis, candidiasis, tinea versicolor, and the like. Because of the delivery-enhancing properties of the conjugates, these conjugates are useful for treating both localized and widespread infections. Antifungal agents are also useful for treating onychomycosis. Examples of antifungal agents include, but are not limited to, azole antifungals such as itraconazole, myconazole and fluconazole. Examples of antiviral agents include, but are not limited to, acyclovir, famciclovir, and valacyclovir. Such agents are useful for treating viral diseases, e.g., herpes.

Another example of a biologically active agent for which enhancement of delivery by conjugation to the delivery-enhancing transporters of the invention is desirable are the antihistamines. These agents are useful for treating conditions such as pruritus due to urticaria, atopic dermatitis, contact dermatitis, psoriasis, and many others. Examples of such reagents include, for example, terfenadine, astemizole, lorotadine, cetirizine, acrivastine, temelastine, cimetidine, ranitidine, famotidine, nizatidine, and the like. Tricyclic antidepressants can also be delivered using the delivery-enhancing transporters of the invention.

Topical antipsoriasis drugs are also of interest. Agents such as corticosteroids, calcipotriene, and anthralin can be conjugated to the delivery-enhancing transporters of the invention and applied to skin.

The delivery-enhancing transporters of the invention are also useful for enhancing delivery of photochemotherapeutic agents into and across one or more layers of skin and other epithelial tissues. Such compounds include, for example, the psoralens, and the like. Sunscreen components are also of interest; these include p-aminobenzoic acid esters, cinnamates and salicylates, as well as benzophenones, anthranilates, and avobenzone.

Pain relief agents and local anesthetics constitute another class of compounds for which conjugation to the delivery-enhancing transporters of the invention can enhance treatment. Lidocaine, bupibacaine, novocaine, procaine, tetracaine, benzocaine, cocaine, and the opiates, are among the compounds that one can conjugate to the delivery-enhancing transporters of the invention. Application of pain relief agents to the joints or skin near the at the joints, e.g., in patients suffering from rhematoid arthritis, is also contemplated.

Other biological agents of interest include, for example, minoxidil, keratolytic agents, destructive agents such as podophyllin, hydroquinone, capsaicin, masoprocol, colchicine, and gold.

Treatment of inflammed joints such as occurs in rhematoid arthritis can also be treated with compounds useful for such treatments conjugated to the transporters of the invention.

B. Gastrointestinal Administration

The delivery-enhancing transporters of the invention are also useful for delivery of conjugated drugs by gastrointestinal administration. Gastrointestinal administration can be used for both systemically active drugs, and for drugs that act in the gastrointestinal epithelium.

Among the gastrointestinal conditions that are treatable using appropriate reagents conjugated to the delivery-enhancing transporters are inflammatory bowel disease such as Crohn's disease (e.g., cyclosporin and ascomycins such as FK506; aminosalicylates, e.g., aspirin-like drugs, which include sulfasalazine and mesalamine; corticosteroids, e.g., prednisone and methylprednisolone; immune modifiers, e.g., azathioprine, 6MP, methotrexate; and antibiotics, e.g., metronidazole, ampicillin, ciprofloxacin, and others). Other treatable gastrointestinal conditions include ulcerative colitis, gastrointestinal ulcers, peptic ulcer disease, imbalance of salt and water absorption (can lead to constipation, diarrhea, or malnutrition), abnormal proliferative diseases, and the like. Ulcer treatments include, for example, drugs that reduce gastric acid secretion, such as $H_2$ histamine inhibitors (e.g., cymetidine and ranitidine) and inhibitors of the proton-potassium ATPase (e.g., lansoprazle and omeprazle), and antibiotics directed at *Helicobacter pylori*.

Compounds useful for the treatment of constipation can also be used in conjunction with the transporters of the invention. Useful compounds for treating constipation include, e.g., surfactant laxatives such as docusate sodium, poloxamer 188, dehydrochloric acid and ricinoleic acid. Exemplary stimulant laxatives include, e.g., phenolphthalein, bisacodyl and anthraquinone laxatives such as danthron.

Antibiotics are among the biologically active agents that are useful when conjugated to the delivery-enhancing transporters of the invention, particularly those that act on invasive bacteria, such as Shigella, Salmonella, and Yersinia. Such compounds include, for example, norfloxacin, ciprofloxacin, trimethoprim, sulfamethyloxazole, and the like.

Anti-neoplastic agents, for example, for the treatment of colon cancer, can also be conjugated to the delivery-enhancing transporters of the invention and administered by the gastrointestinal route. These include, for example, cisplatin, methotrexate, taxol, fluorouracil, mercaptopurine, donorubicin, bleomycin, streptozocin, mitomycin and the like.

For gastrointestinal and colonic delivery of orally administered transporters or active compounds, it can be beneficial to coat or encapsulate the compounds so that the compounds are not released until they are delivered to the gastrointestinal (GI) tract or colon. Methods and composition useful for delivery to the GI tract or colon are described in, e.g., U.S. Pat. Nos. 6,183,466 and 6,120,803.

C. Respiratory Tract Administration

The delivery-enhancing transporters of the invention can also used to enhance administration of drugs through the respiratory tract. The respiratory tract, which includes the nasal mucosa, hypopharynx, and large and small airway structures, provides a large mucosal surface for drug absorption. The enhanced penetration of the conjugated agents into and across one or more layers of the epithelial tissue that is provided by the delivery-enhancing transporters of the invention results in amplification of the advantages that respiratory tract delivery has over other delivery methods. For example, lower doses of an agent are often needed to obtain a desired effect, a local therapeutic effect can occur more rapidly, and systemic therapeutic blood levels of the agent are obtained quickly. Rapid onset of pharmacological activity can result from respiratory tract administration. Moreover, respiratory tract administration generally has relatively few side effects.

The transporters of the invention can be used to deliver biological agents that are useful for treatment of pulmonary conditions. Examples of conditions treatable by nasal administration include, for example, asthma. These compounds include antiinflammatory agents, such as corticosteroids, cromolyn, and nedocromil, bronchodialators such as β2-selective adronergic drugs and theophylline, and immunosuppressive drugs (e.g., cyclosporin and FK506).

Other conditions include, for example, allergic rhinitis (which can be treated with glucocorticoids), and chronic obstructive pulmonary disease (emphysema). Other drugs that act on the pulmonary tissues and can be delivered using the transporters of the invention include beta-agonists, mast cell stabilizers, antibiotics, antifungal and antiviral agents, surfactants, vasoactive drugs, sedatives and hormones.

Respiratory tract administration is useful not only for treatment of pulmonary conditions, but also for delivery of drugs to distant target organs via the circulatory system. A wide variety of such drugs and diagnostic agents can be administered through the respiratory tract after conjugation to the delivery-enhancing transporters of the invention.

D. Delivery of Agents across the Blood Brain Barrier

The delivery-enhancing transporters are also useful for delivering biologically active and diagnostic agents across the blood brain barrier. The agents are useful for treating ischemia (e.g., using an anti-apoptotic drug), as well as for delivering neurotransmitters and other agents for treating various conditions such as schizophrenia, Parkinson's disease, pain (e.g., morphine, the opiates). The 5-hydroxytryptamine receptor antagonist is useful for treating conditions such as migraine headaches and anxiety.

E. Diagnostic Imaging and Contrast Agents

The delivery-enhancing transporters of the invention are also useful for delivery of diagnostic imaging and contrast agents into and across one or more layers of an epithelial and/or endothelial tissue. Examples of diagnostic agents include substances that are labeled with radioactivity, such as $^{99}$mTc glucoheptonate, or substances used in magnetic resonance imaging (MRI) procedures such as gadolinium doped chelation agents (e.g. Gd-DTPA). Other examples of diagnostic agents include marker genes that encode proteins that are readily detectable when expressed in a cell (including, but not limited to, (β-galactosidase, green fluorescent protein, luciferase, and the like. A wide variety of labels may be employed, such as radionuclides, fluors, enzymes, enzyme substrates, enzyme cofactors, enzyme inhibitors, ligands (particularly haptens), etc.

F. Ocular Administration

The delivery-enhancing transporters of the invention can also used to enhance administration of drugs through the tissues of the eye and other related tissues such as the eye lid. The ocular tissues include the cornea, iris, lens, vitreus, vitreus humor, the optic nerve and the eyelid.

Examples of conditions treatable with the compositions of the invention include the following. Conjunctivitis, sometimes called pink eye, is an inflammation of the blood vessels in the conjunctiva, the membrane that covers the sclera and inside of the eyelids. Conjunctivitis may be caused by bacteria or viruses.

Antibacterial and antiviral compounds usful for treating bacterial or viral infections of the eye are well known. See, e.g., Hardman and Limbird, supra. Exemplary compounds include chloramphenicol, Ciproflaxacin, polymyxin B and tetracycline. Exemplary antiviral compounds include idoxuridine, acyclovir and ganciclovir.

Styes are noncontagious, bacterial infections of one of the sebaceous glands of the eyelid. A stye looks like a small, red bump either on the eyelid or on the edge of the eyelid.

Dry eye, or "Sjögren's syndrome," is an immune system disorder characterized by inflammation and dryness of the mouth, eyes, and other mucous membranes, damages the lacrimal glands, and this damage affects tear production. Dry eye can be treated with immunosuppressive compounds such as cyclosporin as well as with ascomycins or steroids.

Glaucoma is a condition in which the normal fluid pressure inside the eyes (intraocular pressure, or IOP) slowly rises as a result of the fluid aqueous humor, which normally flows in and out of the eye, not being able to drain properly. Instead, the fluid collects and causes pressure damage to the optic nerve and loss of vision. Useful compounds to treat glaucoma, blindness, and other eye disorders include, e.g., timolol, levobunolol and phenylepherine. Growth factors such as nerve growth factor (NGF) (see, e.g., Bennett, et al. *Mol Ther* 1(6):501–5 (2000)) are also useful for treating glaucoma and other ocular disorders.

Therapeutic compounds for treatment of ocular diseases, such as those discussed above, are well known to those of skill in the art. Typically, administration of the composition of the invention to the ocular tissues is in the form of an eye drop. Alternatively, for example, the compositions can be injected into the eye or applied as an ointment.

Eye drops including the compounds of the invention can also include an isotonic agent added to sterilized purified water, and if required, a preservative, a buffering agent, a stabilizer, a viscous vehicle and the like are added to the solution and dissolved therein. After dissolution, the pH is adjusted with a pH controller to be within a range suitable for use as an ophthalmic medicine, preferably within the range of 4.5 to 8.

Sodium chloride, glycerin, mannitol or the like may be used as the isotonic agent; p-hydroxybenzoic acid ester, benzalkonium chloride or the like as the preservative; sodium hydrogenphosphate, sodium dihydrogenphosphate, boric acid or the like as the buffering agent; sodium edetate or the like as the stabilizer; polyvinyl alcohol, polyvinyl pyrrolidone, polyacrylic acid or the like as the viscous vehicle; and sodium hydroxide, hydrochloric acid or the like as the pH controller Biologically Active and Diagnostic Molecules Useful with the Delivery-Enhancing Transporters The delivery-enhancing transporters can be conjugated to a wide variety of biologically active agents and molecules that have diagnostic use.

A. Small Organic Molecules

Small organic molecule therapeutic agents can be advantageously attached to linear polymeric compositions as described herein, to facilitate or enhance transport across one or more layers of an epithelial or endothelial tissue. For example, delivery of highly charged agents, such as levodopa (L-3,4-dihydroxy-phenylalanine; L-DOPA) may benefit by linkage to delivery-enhancing transporters as described herein. Peptoid and peptidomimetic agents are also contemplated (e.g., Langston (1997) DDT2:255; Giannis et al. (1997) *Advances Drug Res.* 29:1). Also, the invention is advantageous for delivering small organic molecules that have poor solubilities in aqueous liquids, such as serum and aqueous saline. Thus, compounds whose therapeutic efficacies are limited by their low solubilities can be administered in greater dosages according to the present invention, and can be more efficacious on a molar basis in conjugate form, relative to the non-conjugate form, due to higher uptake levels by cells.

Since a significant portion of the topological surface of a small molecule is often involved, and therefore required, for biological activity, the small molecule portion of the conjugate in particular cases may need to be severed from the attached delivery-enhancing transporter and linker moiety (if any) for the small molecule agent to exert biological activity after crossing the target epithelial tissue. For such situations, the conjugate preferably includes a cleavable linker for releasing free drug after passing through an epithelial tissue.

FIG. 5D and FIG. 5E are illustrative of another aspect of the invention, comprising taxane- and taxoid anticancer conjugates which have enhanced trans-epithelial tissue transport rates relative to corresponding non-conjugated forms. The conjugates are particularly useful for inhibiting growth of cancer cells. Taxanes and taxoids are believed to manifest their anticancer effects by promoting polymerization of microtubules (and inhibiting depolymerization) to an extent that is deleterious to cell function, inhibiting cell replication and ultimately leading to cell death.

Figure 5F:
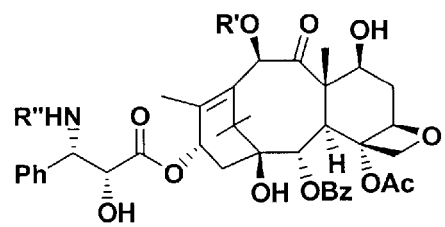
Figure 5G:
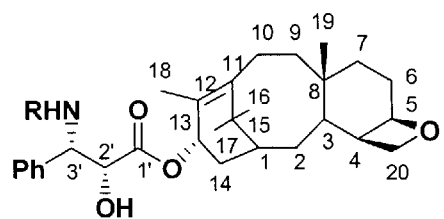
Figure 5H:
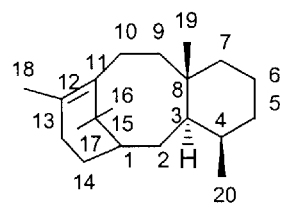

The term "taxane" refers to paclitaxel (FIG. 5F, R'=acetyl, R"=benzyl) also known under the trademark "TAXOL") and naturally occurring, synthetic, or bioengineered analogs having a backbone core that contains the A, B, C and D rings of paclitaxel, as illustrated in FIG. 5G. FIG. 5F also indicates the structure of "TAXOTERE™" (R'=H, R"=BOC), which is a somewhat more soluble synthetic analog of paclitaxel sold by Rhone-Poulenc. "Taxoid" refers to naturally occurring, synthetic or bioengineered analogs of paclitaxel that contain the basic A, B and C rings of paclitaxel, as shown in FIG. 5H. Substantial synthetic and biological information is available on syntheses and activities of a variety of taxane and taxoid compounds, as reviewed in Suffness (1995) *Taxol: Science and Applications*, CRC Press, New York, N.Y., pp. 237–239, particularly in Chapters 12 to 14, as well as in the subsequent paclitaxel literature. Furthermore, a host of cell lines are available for predicting anticancer activities of these compounds against certain cancer types, as described, for example, in Suffness at Chapters 8 and 13.

The delivery-enhancing transporter is conjugated to the taxane or taxoid moiety via any suitable site of attachment in the taxane or taxoid. Conveniently, the transport polymer is linked via a C2'-oxygen atom, C7-oxygen atom, using linking strategies as above. Conjugation of a transport polymer via a C7-oxygen leads to taxane conjugates that have anticancer and antitumor activity despite conjugation at that position. Accordingly, the linker can be cleavable or non-cleavable. Conjugation via the C2'-oxygen significantly reduces anticancer activity, so that a cleavable linker is preferred for conjugation to this site. Other sites of attachment can also be used, such as C10.

It will be appreciated that the taxane and taxoid conjugates of the invention have improved water solubility relative to taxol ($\approx$0.25 $\mu$g/mL) and taxotere (6–7 $\mu$g/mL). Therefore, large amounts of solubilizing agents such as "CREMOPHOR EL" (polyoxyethylated castor oil), polysorbate 80 (polyoxyethylene sorbitan monooleate, also known as "TWEEN 80"), and ethanol are not required, so that side-effects typically associated with these solubilizing agents, such as anaphylaxis, dyspnea, hypotension, and flushing, can be reduced.

B. Metals

Metals can be transported into and across one or more layers of epithelial and endothelial tissues using chelating agents such as texaphyrin or diethylene triamine pentacetic acid (DTPA), conjugated to a delivery-enhancing transporter of the invention, as illustrated by Example. These conjugates are useful for delivering metal ions for imaging or therapy. Exemplary metal ions include Eu, Lu, Pr, Gd, Tc99m, Ga67, In111, Y90, Cu67, and Co57. Preliminary membrane-transport studies with conjugate candidates can be performed using cell-based assays such as described in the Example section below. For example, using europium ions, cellular uptake can be monitored by time-resolved fluorescence measurements. For metal ions that are cytotoxic, uptake can be monitored by cytotoxicity.

C. Macromolecules

The enhanced transport methods of the invention are particularly suited for enhancing transport into and across one or more layers of an epithelial or endothelial tissue for a number of macromolecules, including, but not limited to proteins, nucleic acids, polysaccharides, and analogs thereof. Exemplary nucleic acids include oligonucleotides and polynucleotides formed of DNA and RNA, and analogs thereof, which have selected sequences designed for hybridization to complementary targets (e.g., antisense sequences for single- or double-stranded targets), or for expressing nucleic acid transcripts or proteins encoded by the sequences. Analogs include charged and preferably uncharged backbone analogs, such as phosphonates (preferably methyl phosphonates), phosphoramidates (N3' or N5'), thiophosphates, uncharged morpholino-based polymers, and protein nucleic acids (PNAs). Such molecules can be used in a variety of therapeutic regimens, including enzyme replacement therapy, gene therapy, and anti-sense therapy, for example.

By way of example, protein nucleic acids (PNA) are analogs of DNA in which the backbone is structurally homomorphous with a deoxyribose backbone. The backbone consists of N-(2-aminoethyl)glycine units to which the nucleobases are attached. PNAs containing all four natural nucleobases hybridize to complementary oligonucleotides obeying Watson-Crick base-pairing rules, and is a true DNA mimic in terms of base pair recognition (Egholm et al. (1993) *Nature* 365:566–568. The backbone of a PNA is formed by peptide bonds rather than phosphate esters, making it well-suited for anti-sense applications. Since the backbone is uncharged, PNA/DNA or PNA/RNA duplexes that form exhibit greater than normal thermal stability. PNAs have the additional advantage that they are not recognized by nucleases or proteases. In addition, PNAs can be synthesized on an automated peptides synthesizer using standard t-Boc chemistry. The PNA is then readily linked to a transport polymer of the invention.

Figure 7:
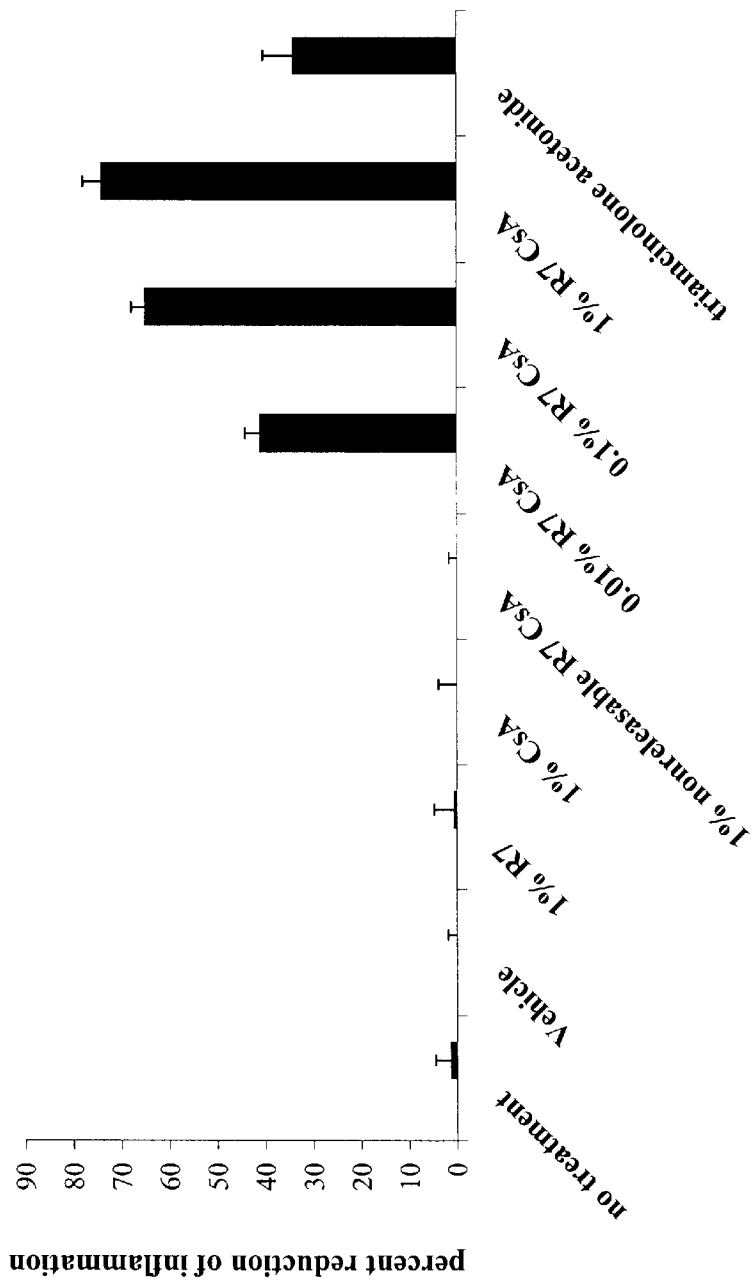
FIG. 7 displays inhibition of inflammation in murine contact dermatitis by releasable R7 CsA. Balb/c (6–7 weeks) mice were painted on the abdomen with 100 μl of 0.7% DNFB in acetone olive oil (95:5). Three days later both ears of the animals were restimulated with 0.5% DNFB in acetone. Mice were treated one, five, and twenty hours after restimulation with either vehicle alone, 1% R7 peptide alone, 1% CsA, 1% nonreleasable R7 CsA, 0.01%/0.1%/1.0% releasable R7 CsA, and the fluorinated steroid positive control 0.1% triamcinolone acetonide. Ear inflammation was measured 24 hours after restimulation using a spring loaded caliper. The percent reduction of inflammation was calculated using the following formula (t–n)/(u–n), where t=thickness of the treated ear, n=the thickness of a normal untreated ear, and u=thickness of an inflamed ear without any treatment. N=20 animals in each group.

Examples of anti-sense oligonucleotides whose transport into and across epithelial and endothelial tissues can be enhanced using the methods of the invention are described, for example, in U.S. Pat. No. 5,594,122. Such oligonucleotides are targeted to treat human immunodeficiency virus (HIV). Conjugation of a transport polymer to an anti-sense oligonucleotide can be effected, for example, by forming an amide linkage between the peptide and the 5'-terminus of the oligonucleotide through a succinate linker, according to well-established methods. The use of PNA conjugates is further illustrated in Example 11 of PCT Application PCT/US98/10571. FIG. 7 of that application shows results obtained with a conjugate of the invention containing a PNA sequence for inhibiting secretion of gamma-interferon ($\gamma$-IFN) by T cells, as detailed in Example 11. As can be seen, the anti-sense PNA conjugate was effective to block $\gamma$-IFN secretion when the conjugate was present at levels above about 10 $\mu$M. In contrast, no inhibition was seen with the sense-PNA conjugate or the non-conjugated antisense PNA alone.

Another class of macromolecules that can be transported across one or more layers of an epithelial or endothelial tissue is exemplified by proteins, and in particular, enzymes. Therapeutic proteins include, but are not limited to replacement enzymes. Therapeutic enzymes include, but are not limited to, alglucerase, for use in treating lysozomal glucocerebrosidase deficiency (Gaucher's disease), alpha-L-iduronidase, for use in treating mucopolysaccharidosis I, alpha-N-acetylglucosamidase, for use in treating sanfilippo B syndrome, lipase, for use in treating pancreatic insufficiency, adenosine deaminase, for use in treating severe combined immunodeficiency syndrome, and triose phosphate isomerase, for use in treating neuromuscular dysfunction associated with triose phosphate isomerase deficiency.

In addition, and according to an important aspect of the invention, protein antigens may be delivered to the cytosolic compartment of antigen-presenting cells (APCs), where they are degraded into peptides. The peptides are then transported into the endoplasmic reticulum, where they associate with nascent HLA class I molecules and are displayed on the cell surface. Such "activated" APCs can serve as inducers of class I restricted antigen-specific cytotoxic T-lymphocytes (CTLs), which then proceed to recognize and destroy cells displaying the particular antigen. APCs that are able to carry out this process include, but are not limited to, certain macrophages, B cells and dendritic cells. In one embodiment, the protein antigen is a tumor antigen for eliciting or promoting an immune response against tumor cells. The transport of isolated or soluble proteins into the cytosol of APC with subsequent activation of CTL is exceptional, since, with few exceptions, injection of isolated or soluble proteins does not result either in activation of APC or induction of CTLs. Thus, antigens that are conjugated to the transport enhancing compositions of the present invention may serve to stimulate a cellular immune response in vitro or in vivo.

In another embodiment, the invention is useful for delivering immunospecific antibodies or antibody fragments to the cytosol to interfere with deleterious biological processes such as microbial infection. Recent experiments have shown that intracellular antibodies can be effective antiviral agents in plant and mammalian cells (e.g., Tavladoraki et al. (1993) *Nature* 366:469; and Shaheen et al. (1996) *J. Virol.* 70:3392. These methods have typically used single-chain variable region fragments (scFv), in which the antibody heavy and light chains are synthesized as a single polypeptide. The variable heavy and light chains are usually separated by a flexible linker peptide (e.g., of 15 amino acids) to yield a 28 kDa molecule that retains the high affinity ligand binding site. The principal obstacle to wide application of this technology has been efficiency of uptake into infected cells. But by attaching transport polymers to scFv fragments, the degree of cellular uptake can be increased, allowing the immunospecific fragments to bind and disable important microbial components, such as HIV Rev, HIV reverse transcriptase, and integrase proteins.

D. Peptides

Peptides to be delivered by the enhanced transport methods described herein include, but should not be limited to, effector polypeptides, receptor fragments, and the like. Examples include peptides having phosphorylation sites used by proteins mediating intra-cellular signals. Examples of such proteins include, but are not limited to, protein kinase C, RAF-1, p21Ras, NF-κB, C-JUN, and cytoplasmic tails of membrane receptors such as IL-4 receptor, CD28, CTLA-4, V7, and MHC Class I and Class II antigens.

When the delivery-enhancing transporter is also a peptide, synthesis can be achieved either using an automated peptide synthesizer or by recombinant methods in which a polynucleotide encoding a fusion peptide is produced, as mentioned above.

EXAMPLES

The following examples are offered to illustrate, but not to limit the present invention.

Example 1

Penetration of Biotinylated Polymers of D-Arginine into the Skin of Nude Mice

This Example demonstrates that poly-arginine heptamers can deliver conjugated biotin into and across layers of the skin, both follicularly and interfollicularly, and into the dermis.

Methods

Biotinylated peptides were synthesized using solid phase techniques and commercially available Fmoc amino acids, resins, and reagents (PE Biosystems, Foster City Calif., and Bachem Torrence, Calif.) on a Applied Biosystems 433 peptide synthesizer. Fastmoc cycles were used with O-(7-azabenzotriazol-1-yl)-1,1,3,3-tetramethyluronium hexfluorophosphate (HATU) substituted for HBTU/HOBt as the coupling reagent. Prior to the addition of biotin to the amino terminus of the peptide, amino caproic acid (aca) was conjugated and acted as a spacer. The peptides were cleaved from the resin using 96% trifluoroacetic acid, 2% triisopropyl silane, and 2% phenol for between 1 and 12 hours. The longer reaction times were necessary to completely remove the Pbf protecting groups from the polymers of arginine. The peptides subsequently were filtered from the resin, precipitated using diethyl ether, purified using HPLC reverse phase columns (Alltech Altima, Chicago, Ill.) and characterized using either electrospray or matrix assisted laser desorption mass spectrometry (Perceptive Biosystems, Boston, Mass.).

Varying concentrations (1 mM-10 µM) of a heptamer of D-arginine with biotin covalently attached to the amino terminus using an amino caproic acid spacer (bio r7), dissolved in phosphate buffered saline (PBS), were applied to the back of anesthetized nude mice. Samples (100 µl) were applied as a liquid without excipient, prevented from dispersing by a Vaseline™ barrier, and allowed to penetrate for fifteen minutes. At the end of this period the animal was sacrificed, the relevant sections of skin were excised, embedded in mounting medium (OCT), and frozen. Frozen sections (5 microns) were cut using a cryostat, collected on slides, and stained with fluorescently labeled streptavidin (Vector Laboratories, Burlingame, Calif.). The slides were fixed in acetone at 4° C. for ten minutes, air dried, soaked in PBS for five minutes, blocked with normal goat serum for five minutes, and washed with PBS for five minutes. The section was stained by incubation with fluorescently labeled streptavidin at 30 µg/ml for thirty minutes, washed with PBS, counterstained with propidium iodide (1 µg/ml) for two minutes, and the section was mounted with Vectashield™ mounting media. Slides were analyzed by fluorescent microscopy. Parallel studies were done using streptavidin-horse radish peroxidase rather than fluorescein-streptavidin. The biotinylated peptide was visualized by treatment of the sections with the horseradish peroxidase substrate diaminobenzadine, and visualization with light microscopy.

Results

Biotinylated arginine heptamer crossed into and across the epidermis and into the dermis. The cytosol and nuclei of all cells in the field were fluorescent, indicating penetration into virtually every cell of the nude mouse skin in the section. The staining pattern was consistent with unanticipated transport that was both follicular and interfollicular. In addition, positive cells were apparent in papillary and reticular dermis. In contrast, no staining was apparent in mice treated with biotin alone, or phosphate buffered saline alone.

Example 2

Penetration of Biotinylated Polymers of D-Arginine into the Skin of Normal Balb/C Mice Varying concentrations (1 mM-100 µM) of a heptamer of D-arginine with biotin covalently attached to the amino terminus using an amino caproic acid spacer (bio r7), dissolved in PBS, were applied to a skin of the groin of an anesthetized Balb/C mice. Sample (100 µl) was applied as a liquid within excipient and prevented from dispersing by a Vaseline™ barrier and allowed to penetrate for thirty minutes. At the end of this period animal was sacrificed, the relevant section of skin was excised, embedded in mounting medium (OCT) and frozen. Frozen sections were cut using a cryostat, collected on slides, and stained with fluorescently labeled streptavidin (Vector Laboratories, Burlingame, Calif.) as described in Example 1. Slides were analyzed by fluorescent microscopy.

Results

As with the skin from nude mice, biotinylated arginine heptamer crossed into and across the epidermis and into the dermis. The cytosol and nuclei of all cells in the field were fluorescent, indicating penetration into virtually every cell of the nude mouse skin in the section. The staining pattern was consistent with unanticipated transport that was both follicular and interfollicular. In addition, positive cells were apparent in papillary and reticular dermis. In contrast, no staining was apparent in mice treated with biotin alone, or phosphate buffered saline alone.

Example 3

Penetration of Biotinylated Polymers of D-Arginine into Normal Human Skin Grafted onto Nude Mice Varying concentrations (1 mM-100 µM) of a heptamer of D-arginine with biotin covalently attached to the amino terminus using an amino caproic acid spacer (bio r7), dissolved in PBS, were applied to human foreskin grafts on the back of SCID mice (see, e.g., Deng et al. (1997) Nature Biotechnol. 15: 1388–1391; Khavari et al. (1997) Adv. Clin. Res. 15:27–35; Choate and Khavari (1997) Human Gene Therapy 8:895–901). Samples (100 µl) were applied as a liquid within excipient and prevented from dispersing by a Vaseline™ barrier and allowed to penetrate for fifteen minutes. At the end of this period animal was sacrificed, the relevant section of skin was excised, embedded in mounting medium (OCT) and frozen. Frozen sections were cut using a cryostat, collected on slides, and stained with fluorescently labeled streptavidin (Vector Laboratories, Burlingame, Calif.) as described in Example 1. Slides were analyzed by fluorescent microscopy.

Results

As with the skin from nude and normal mice, biotinylated arginine heptamer crossed into and across the epidermis and into the dermis of the human skin. The cytosol and nuclei of all cells in the field were fluorescent, indicating penetration into and through the epidermis and dermis. Intense staining was seen at both 20× and 40× magnification. The staining pattern was consistent with unanticipated transport that was both follicular and interfollicular. In addition, positive cells were apparent in papillary and reticular dermis. In contrast, no staining was apparent in mice treated with biotin alone, or phosphate buffered saline alone, and very little staining was observed with the biotinylated arginine pentamer conjugate, either at low or high magnification.

Example 4

Increased Penetration of Biotinylated Polymers of D-Arginine into Skin of Nude Mouse Using Plastic Wrap or a Lotion Excipient Varying concentrations (1 mM-100 µM) of a heptamer of D-arginine with biotin covalently attached to the amino terminus using an amino caproic acid spacer (bio r7), dissolved in PBS, and mixed with an equal volume of Lubridern™. The lotion mixture was then applied to the back of nude mice and allowed to penetrate for thirty, sixty, and 120 minutes. Alternatively, sample (100 µl) was applied as a liquid without excipient and prevented from evaporating by wrapping plastic wrap over the sample sealed with Vaseline™. The samples were allowed to penetrate for thirty, sixty, and 120 minutes. At the end of this period animal was sacrificed, the relevant section of skin was excised, embedded in mounting medium (OCT) and frozen. Frozen sections were cut using a cryostat, collected on slides, and stained with fluorescently labeled streptavidin (Vector Laboratories, Burlingame, Calif.) as described in Example 1. Slides were analyzed by fluorescent microscopy.

Results

Both lotion and plastic wrap resulted in increased uptake compared with staining without excipient. Lotion was more effective than plastic wrap in enhancing uptake of the conjugate. Biotinylated arginine pentamers crossed into and across several skin layers, reaching both the cytosol and nuclei of epidermal cell layers, both follicular and interfollicular. In addition, positive cells were apparent in papillary and reticular dermis.

Example 5

Penetration of Cyclosporin Conjugated to a Biotinylated Pentamer, Heptamer, and Nonamer of D-Arginine into the Skin of Nude Mice Methods A. Linking Cyclosporin to Delivery-Enhancing Transporters 1. Preparation of the α-Chloroacetyl Cyclosporin A Derivative.

The α-chloroacetyl cyclosporin A derivative was prepared as shown in FIG. 1. Cyclosporin A (152.7 mg, 127 µmol) and chloroacetic acid anhydride (221.7 mg; 1300 µmol) were placed into a dry flask under $N_2$-atmosphere. Pyridine (1.0 mL) was added and the solution was heated to 50° C. (oil bath). After 16 hours the reaction was cooled to room temperature and quenched with water (4.0 mL). The resulting suspension was extracted with diethylether (Σ 15 mL). The combined organic layers were dried over $MgSO_4$. Filtration and evaporation of solvents in vacuo delivered a yellow oil, which was purified by flash chromatography on silica gel (eluent: EtOAc/hexanes: 40%–80%) yielding 136 mg (106.4 µmol, 83%) of the desired product.

2. Coupling to Transporter Molecules

Figure 2:
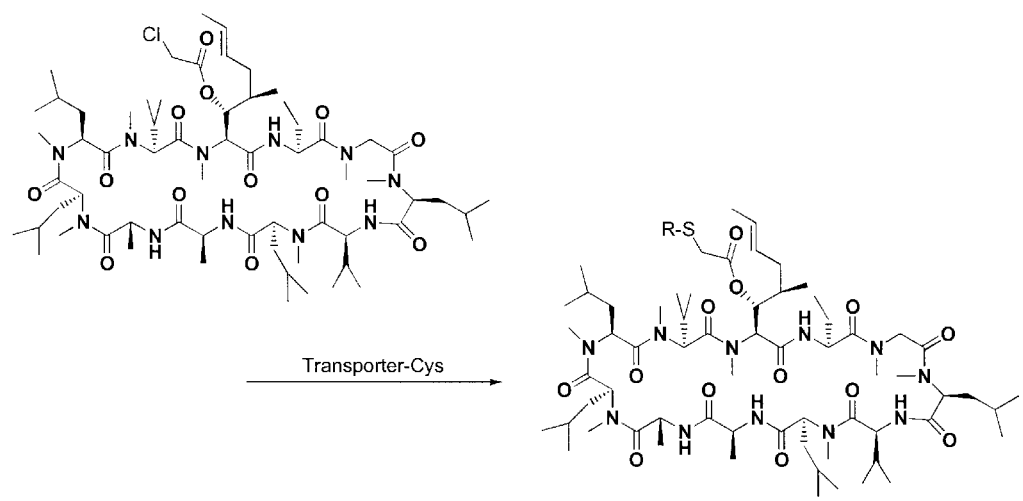
FIG. 2 shows a general procedure for the coupling of cysteine-containing peptides to the α-chloro acetyl cyclosporin A derivative.

A general procedure for the coupling of cysteine containing peptides to the α-chloro acetyl Cyclosporin A derivative is shown in FIG. 2.

a. Labeled Peptides

Figure 3:
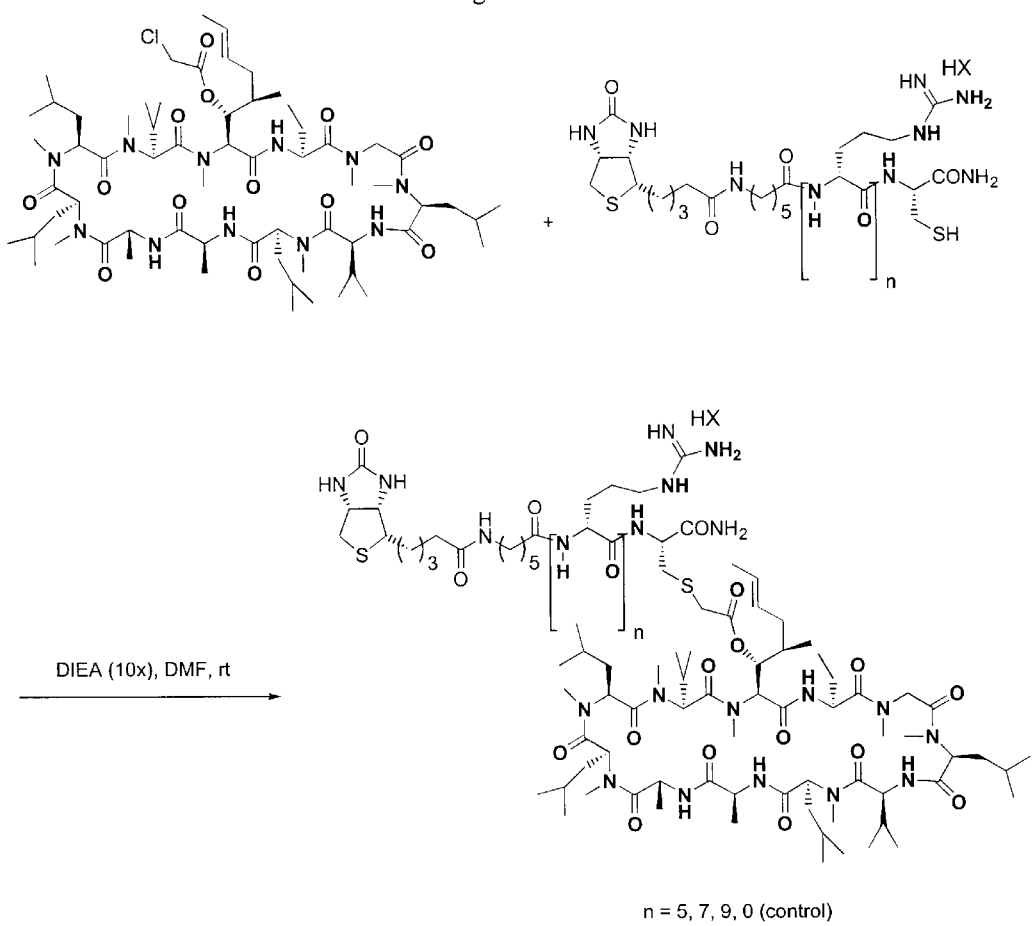
FIG. 3 shows a reaction scheme for the coupling of the cyclosporin A derivative to a biotin-labeled peptide.

The cyclosporin A derivative and the labeled peptide (1 equivalent) were dissolved in DMF (10 mmol of Cyclosporin A derivative/mL DMF) under an $N_2$-atmosphere. Diisopropylethylamine (10 equivalents) was added and stirring at room temperature was continued until all starting material was consumed (usually after 16 hours) (FIG. 3). The solvents were removed in vacuo and the crude reaction product was dissolved in water and purified by reversed phase high pressure liquid chromatography (RP-HPLC) (eluent:water/MeCN*TFA). The products were obtained in the following yields:

B-aca-r5-Ala-Ala-Cys-O-acyl-Cyclosporin A: 47%

B-aca-r7-Cys-O-acyl-Cyclosporin A: 43%

B-aca-r9-Cys-O-acyl-Cyclosporin A: 34%

B-aca-Cys-O-acyl-Cyclosporin A: 55% b. Unlabeled Peptides

Figure 4:
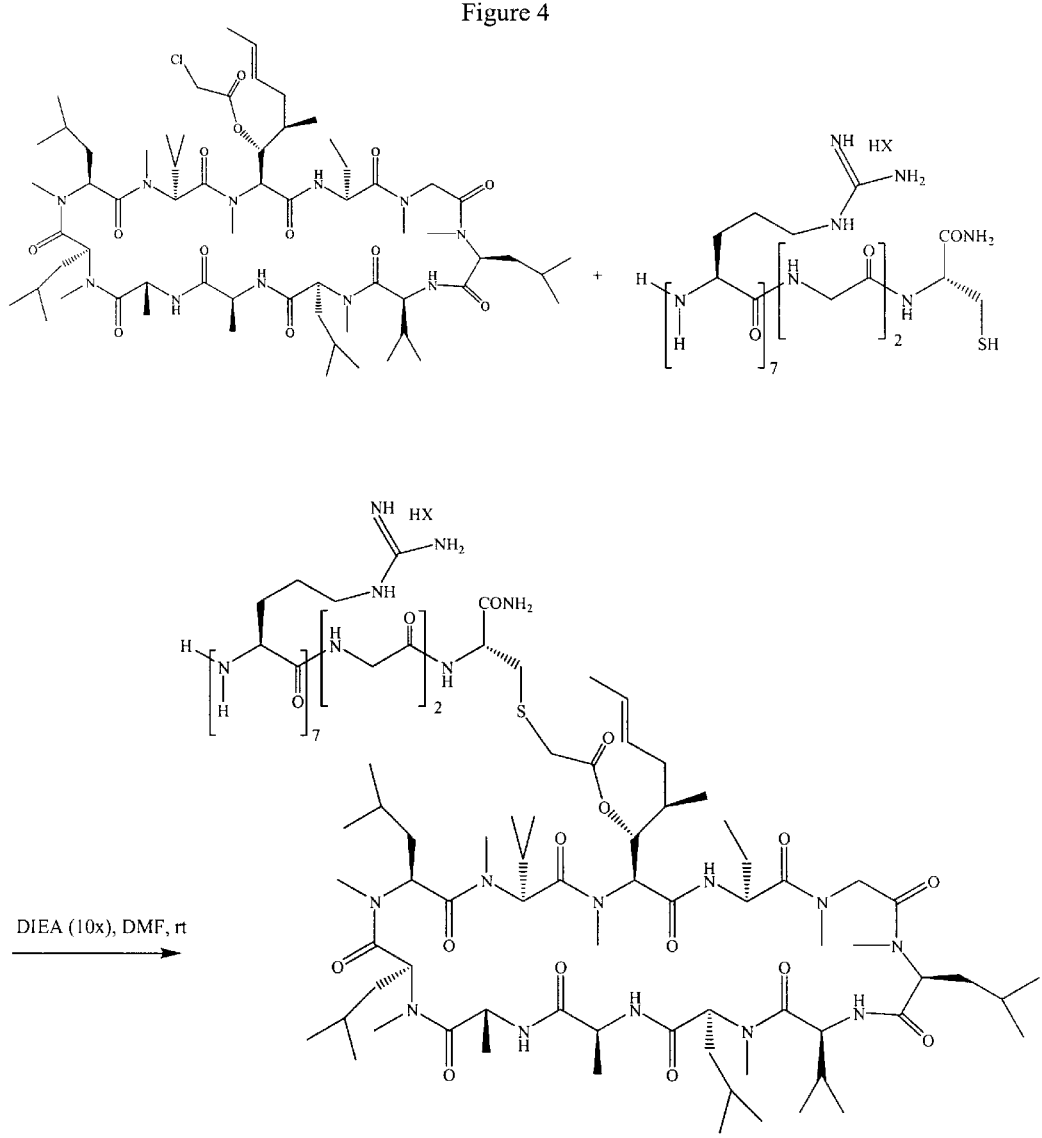
FIG. 4 shows a reaction scheme for coupling of a cyclosporin A derivative to an unlabeled peptide (SEQ ID NO:7).

The peptide (34.7 mg, 15.3 µmol) and the Cyclosporin A derivative (19.6 mg, 15.3 µmol) were dissolved in DMF (1.0 mL) under an N$_2$-atmosphere (FIG. 4). Diisopropylethylamine (19.7 mg, 153 μmol) was added and stirring at room temperature was continued. After 12 hours the solvent was removed in vacuo. The crude material was dissolved in water and purified by RP-HPLC (eluent:water/MeCN*TFA) yielding the pure product (24.1 mg, 6.8 mmol, 44%).

B. Analysis of Transport Across Skin

Varying concentrations (1 mM-100 μM) of cyclosporin conjugated to either biotinylated pentamer, heptamer, or nonamers of D-arginine (bio r5, r7, or r9), dissolved in PBS, were applied to the back of nude mice. Samples (100 μl) were applied as a liquid within excipient and prevented from dispersing by a Vaseline™ barrier and allowed to penetrate for thirty, sixty, and 120 minutes. At the end of this period animal was sacrificed, the relevant section of skin was excised, embedded in mounting medium (OCT) and frozen. Frozen sections were cut using a cryostat, collected on slides, and stained with fluorescently labeled streptavidin (Vector Laboratories, Burlingame, Calif.) as described in Example 1. Slides were analyzed by fluorescent microscopy Results The conjugates of cyclosporin with biotinylated heptamers and nonamers of D-arginine effectively entered into and across the epidermis and into the dermis of the skin of nude mice. In contrast, very little uptake was seen using a conjugate between a pentamer of arginine and cyclosporin, and no staining was seen with a PBS control. The cytosol and nuclei of all cells in the field were fluorescent, indicating penetration into and through the epidermis and dermis. The staining pattern was consistent with unanticipated transport that was both follicular and interfollicular. In addition, positive cells were apparent in papillary and reticular dermis. These results demonstrate remarkable uptake only when sufficient guanidinyl groups are included in the delivery-enhancing transporter.

Example 6

Demonstration that a D-Arginine Heptamer Can Penetrate Human Skin

Human and murine skin differ significantly in a number of ways, with human epidermis being considerably thicker. To determine if the D-arginine heptamers/cyclosporin A (r7 CsA) conjugate could also penetrate human skin, biotin r7 CsA was applied to full thickness human skin grafted onto the back of a SCID mouse. As in murine skin, conjugated cyclosporin A penetrated human epidermis and dermis. Fluorescence was observed in both the cytosol and the nuclei of cells in tissue exposed to biotinylated peptides alone, but in sections stained with biotin r7 CsA the majority of fluorescence was cytosolic, consistent with r7 CsA binding to cyclosporin A's known cytoplasmic targets.

Example 7

Demonstration that Cyclosporin A-Transporter Conjugates Enter T Cells in the Dermis Methods Inhibition of IL-2 Secretion by Releasable R7-CsA Conjugate.

Jurkat cells (5×10$^4$) were incubated with varying concentrations of a nonreleasable or releasable R7-CsA conjugate or CsA overnight at 37° C. to allow for the release of the active form of CsA prior to stimulation with PMA and ionomycin. T cells subsequently were stimulated to produce IL-2 by addition of 10 ng/ml PMA (Sigma, St. Louis, Mo.) and 1 μM ionomycin (CalBiochem, San Diego, Calif.). Cultures were incubated overnight at 37° C. and supernatants were collected and IL-2 was measured using a fluorescent ELISA. Briefly, plates were coated with 4 μg/ml anti-human IL-2 antibody (BD Pharmingen, San Diego, Calif.), blocked with PBS containing 10% FBS for 1 hour at room temperature, washed, and supernatants added and incubated for 1 hour. Media was removed and biotinylated anti-human IL-2 (1.6 μg/ml), was added for one hour. The plates were washed, and then europium labeled streptavidin (0.04 ng/ml) was added for one hour. After another wash, enhancement solution was added and the resulting fluorescence was measured using a Wallac plate reader (Wallac, Turku, Finland).

Results

To determine whether biotinylated D-arginine heptamer-cyclosporin (r7 CsA) conjugate would reach infiltrating T cells within inflamed skin in vivo, biotin r7 CsA was applied to the site of inflammation on the back of a mouse with experimentally induced contact dermatitis. Inflamed skin was stained with rhodamine labeled goat anti-mouse CD3 to localize T-cells and with fluorescein labeled streptavidin to localize the biotin r7 CsA. Biotin r7 CsA was found in all CD3[+] T cells in the tissue in addition to a variety of other cells that probably represent other inflammatory cells as well as resident fibroblasts. These data indicate that biotin r7 CsA penetrates inflamed skin to reach key target T lymphocytes.

Example 8

Synthesis, in vitro and in vivo Activity of a Releasable Conjugate of a Short Oligomer of Arginine and CsA Modification of the 20 alcohol of Cyclosporin A results in significant loss of its biological activity. See, e.g., R. E. Handschumacher, et al, *Science* 226, 544–7 (1984). Consequently, to ensure release of free Cyclosporin A from its conjugate after transport into cells, Cyclosporin A was conjugated to an oligo-arginine transporter through a pH sensitive linker as shown in FIG. 10. The resultant conjugate is stable at acidic pH but at pH>7 it undergoes an intramolecular cyclization involving addition of the free amine to the carbonyl adjacent to Cyclosporin A (FIG. 6), which results in the release of unmodified Cyclosporin A.

Another modification in the design of the releasable conjugate was the use of L-arginine (R), and not D-arginine (r) in the transporter. While the oligo-D-arginine transporters were used for the histological experiments to ensure maximal stability of the conjugate and therefore accuracy in determining its location through fluorescence, oligomers of L-arginine were incorporated into the design of the releasable conjugate to minimize its biological half-life. Consistent with its design, the resultant releasable conjugate was shown to be stable at acidic pH, but labile at physiological pH in the absence of serum. This releasable Cyclosporin A conjugate's half-life in pH 7.4 PBS was 90 minutes.

Results

The releasable guanidino-heptamer conjugate of Cyclosporin A was shown to be biologically active by inhibiting IL-2 secretion by the human T cell line, Jurkat, stimulated with PMA and ionomycin in vitro. See R. Wiskocil, et al., *J Immunol* 134, 1599–603 (1985). The conjugate was added 12 hours prior to the addition of PMA/ionomycin and dose dependent inhibition was observed by the releasable R7 CsA conjugate. This inhibition was not observed with a nonreleasable analog (FIG. 6) that differed from the releasable conjugate by retention of the t-Boc protecting group, which prevented cyclization and resultant release of the active drug. The $EC_{50}$ of the releasable R7 cyclosporin conjugate was approximately two fold higher than CsA dissolved in alcohol and added at the same time as the releasable conjugate.

The releasable R7 CsA conjugate was assayed in vivo for functional activity using a murine model of contact dermatitis. Treatment with the 1% releasable R7 CSA conjugate resulted in 73.9%±4.0 reduction in ear inflammation (FIG. 7). No reduction in inflammation was seen in the untreated ear, indicating that the effect seen in the treated ear was local and not systemic. Less inhibition was observed in the ears of mice treated with 0.1 and 0.01% R7-CsA (64.8%±4.0 and 40.9%±3.3 respectively), demonstrating that the effect was titratable. Treatment with the fluorinated corticosteroid positive control resulted in reduction in ear swelling (34.1%±6.3), but significantly less than that observed for 0.1% releasable R7 CsA (FIG. 7). No reduction of inflammation was observed in any of the mice treated with unmodified Cyclosporin A, vehicle alone, R7 (SEQ ID NO:3), or nonreleasable R7 CsA.

Example 9

The Penetration of Copper and Gadolinium-DTPA-r7 Complexes into the Skin of Nude Mice Methods 1. Preparation of Metal Complexes Step 1—Preparation of Copper-diethylenetriaminepentaacetic Acid Complex (Cu-DTPA)

Figure 8:
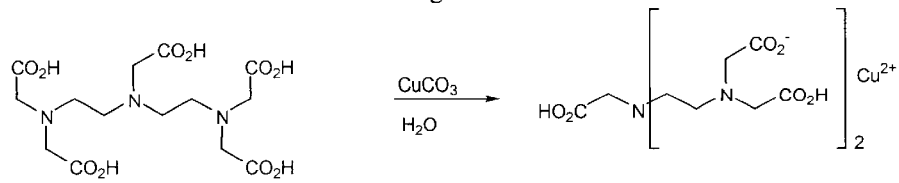
FIG. 8 shows a procedure for the preparation of a copper-diethylene-triaminepentaacetic acid complex (Cu-DTPA).

Copper carbonate (10 mmol) and diethylenetriaminpentacetic acid (10 mmol) were dissolved in water (150 mL) (FIG. 8). After 18 h, the solution was centrifuged to removed any solids. The blue solution was decanted and lyophilized to provide a blue powder (yields >90%).

Step 2—Preparation of DTPA Transporter

Figure 9:
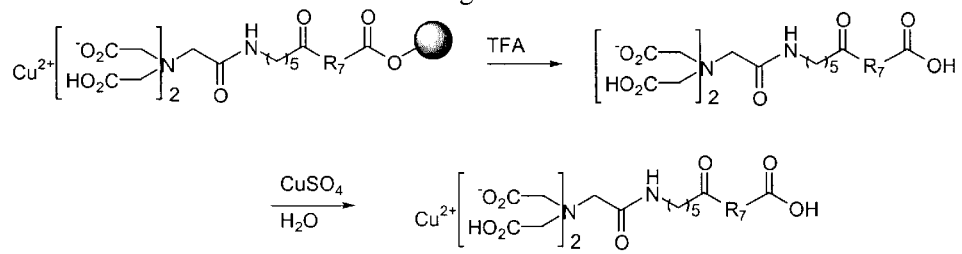
FIG. 9 shows a procedure for linking the Cu-DTPA to a transporter through an aminocaproic acid.

The Cu-DTPA was linked to a transporter through an aminocaproic acid spacer using a PE Applied Biosystems Peptide Synthesizer (ABI 433A) (FIG. 9). The material was cleaved from the resin by treatment with trifluoroacetic acid (TFA) (40 mL), triisopropyl silane (100 μL) and phenol (100 μL) for 18 h. The resin was filtered off and the peptide was precipitated by addition of diethyl ether (80 mL). The solution was centrifuged and the solvent decanted off. The crude solid was purified by reverse-phase HPLC using a water/acetonitrile gradient. Treatment with TFA resulted in loss of $Cu^{2+}$ ion which needed to be reinserted.

DTPA-aca-R7-CO2H (SEQ ID NO:31) (10 mg, 0.0063 mmol) and copper sulfate (1.6 mg, 0.0063 mmol) were dissolved in water (1 mL). Let gently stir for 18 h and lyophilized to provide product as a white powder (10 mg).

2. Analysis of Transport Across Skin

Metal diethylenetriaminepentaacetic acid (DTPA) complexes were formed by mixing equimolar amounts of metal salts with DTPA in water for 18 hours. At the end of this time, the solutions were centrifuged, frozen and lyophilized. The dried powder was characterized by mass spectrometry and used in solid phase peptide synthesis. The metal-DTPA complexes were attached to polymers of D- or L-arginine that were still attached to solid-phase resin used in peptide synthesis. The metal-DTPA complexes were attached using an aminocaproic acid spacer. The solid phase peptide synthesis techniques were described in Example 1, with the exception that cleavage of the peptide-DTPA-metal complex in trifluoroacetic acid released the metal. The metal is replaced after HPLC purification and lyophilization of the peptide-DTPA complex. Replacement of the metal involved incubation of equimolar amounts of the metal salt with the peptide-aminocaproic acid-DTPA complex and subsequent lyophilization.

Varying concentrations (1 μM to 1 mM) of the Cu-DTPA-aca-r7 complex were applied to the abdominal region of nude mice for 15, 30 and 45 minutes. As controls, an equimolar amount of the Cu-DTPA complex was spotted onto the abdominal region. At the end of the incubation period, the samples were simply wiped off and intense blue color was apparent on the skin where the Cu-DTPA-aca-r7 complex was spotted and not where the Cu-DTPA alone was spotted. In the case of the application of 1 mM, visible blue dye was seen for three days, decreasing with time, but being apparent for the full period.

Varying concentrations (1 μM to 1 mM) of the Gd-DTPA-aca-r7 complex are injected into the tail vein of BALB/c mice in 100 μl. Distribution of the Gd is observed in real time using magnetic resonance imaging. Distribution of the dye is apparent throughout the bloodstream, entering liver, spleen, kidney, and heart. When injected into the carotid artery of rabbits, the dye is seen to cross the blood brain barrier.

Example 10

Penetration of Hydrocortisone Conjugated to a Biotinylated Pentamer, Heptamer, and Nonamer of D-Arginine into the Skin of Nude Mice Methods A. Linking of Hydrocortisone to Delivery-Enhancing Transporters Step 1—Acylation of Hydrocortisone with Chloroacetic Anhydride.

Figure 10:
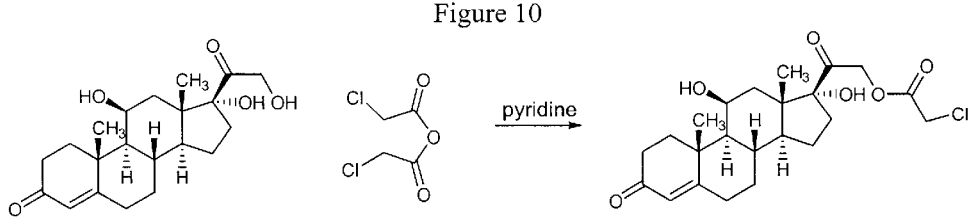
FIG. 10 shows a reaction for the acylation of hydrocortisone with chloroacetic anhydride.

A solution of hydrocortisone (200 mg, 0.55 mmol) and chloroacetic anhydride (113 mg, 0.66 mmol) in pyridine (5 mL) was stirred at room temperature for 2 h (FIG. 10). The solvent was evaporated off and the crude product was chromatographed on silica using 50% hexanes/ethyl acetate as the eluent. Product isolated a whites solid (139 mg, 58%).

Step 2—Linking to Transporter.

Figure 11:
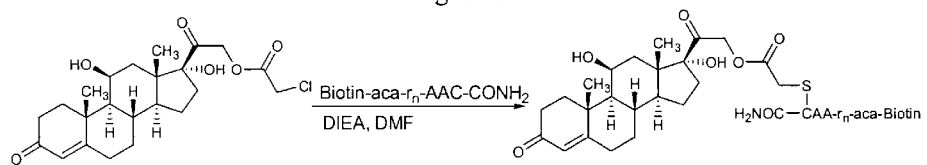
FIG. 11 shows a reaction for linking the acylated hydrocortisone to a transporter.

A solution of the chloroacetic ester of hydrocortisone (0.0137 mmol), a transporter containing a cysteine residue (0.0137) and diisopropylethylamine (DIEA) (0.0274 mmol) in dimethylformamide (DMF) (1 mL) was stirred at room temperature for 18 h (FIG. 11). The material was purified via reverse-phase HPLC using a water/acetonitrile gradient and lyophilized to provide a white powder.

r5 conjugate—12 mg obtained (29% isolated yield)

r7 conjugate—22 mg obtained (55% isolated yield)

R7 conjugate—13 mg obtained (33% isolated yield)

B. Analysis of Transport Across Skin

Varying concentrations (1 mM-100 μM) of hydrocortisone conjugated to either biotinylated pentamer, heptamer, or nonamers of D-arginine (bio r5, r7, or r9), dissolved in PBS, were applied to the back of nude mice. Samples (100 μl) were applied as a liquid within excipient and prevented from dispersing by a Vaseline™ barrier and allowed to penetrate for thirty, sixty, and 120 minutes. At the end of this period animal was sacrificed, the relevant section of skin was excised, embedded in mounting medium (OCT) and frozen. Frozen sections were cut using a cryostat, collected on slides, and stained with fluorescently labeled streptavidin (Vector Laboratories, Burlingame, Calif.) as described in Example 1. Slides were analyzed by fluorescent microscopy.

Results

The conjugates of hydrocortisone with biotinylated heptamers of D-arginine effectively entered into and across the epidermis and into the dermis of the skin of nude mice. In contrast, very little uptake was seen using a conjugate between a pentamer of arginine and hydrocortisone, and no staining was seen with a PBS control. The cytosol and nuclei of all cells in the field were fluorescent, indicating penetration into and through the epidermis and dermis. The staining pattern was consistent with unanticipated transport that was both follicular and interfollicular. In addition, positive cells were apparent in papillary and reticular dermis. These results demonstrate remarkable uptake only when sufficient guanidinyl groups are included in the delivery-enhancing transporter.

Example 11

Figure 12:
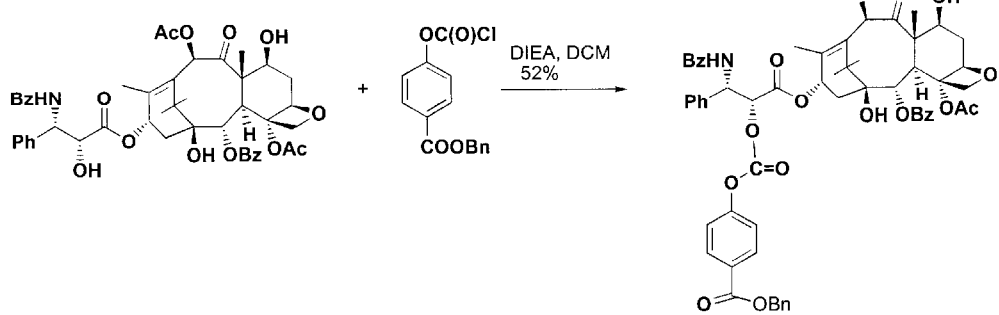
FIG. 12 shows a reaction for preparation of C-2' derivatives of taxol.

Penetration of Taxol Conjugated to a Biotinylated Pentamer, Heptamer, and Nonamer of D-Arginine into the Skin of Nude Mice Methods 1. Conjugation of C-2' Activated Taxol Derivatives to Biotin-Labeled Peptides Synthesis of C-2' Derivatives Taxol (48.7 mg, 57.1 µmol) was dissolved in $CH_2Cl_2$ (3.0 mL) under an $N_2$-atmosphere. The solution was cooled to 0° C. A stock solution of the chloroformate of benzyl-(p-hydroxy benzoate) (200 mmol, in 2.0 mL $CH_2Cl_2$-freshly prepared from benzyl-(p-hydroxy benzoate) and diphosgene) was added at 0° C. and stirring at that temperature was continued for 5 hours, after which the solution was warmed to room temperature (FIG. 12). Stirring was continued for additional 10 hours. The solvents were removed in vacuo and the crude material was purified by flash chromatography on silica gel (eluent: EtOAc/hexanes 30%–70%) yielding the desired taxol C-2' carbonate (36.3 mg, 32.8 µmol, 57.4%).

Coupling to Biotin-Labeled Peptides.

Figure 13:
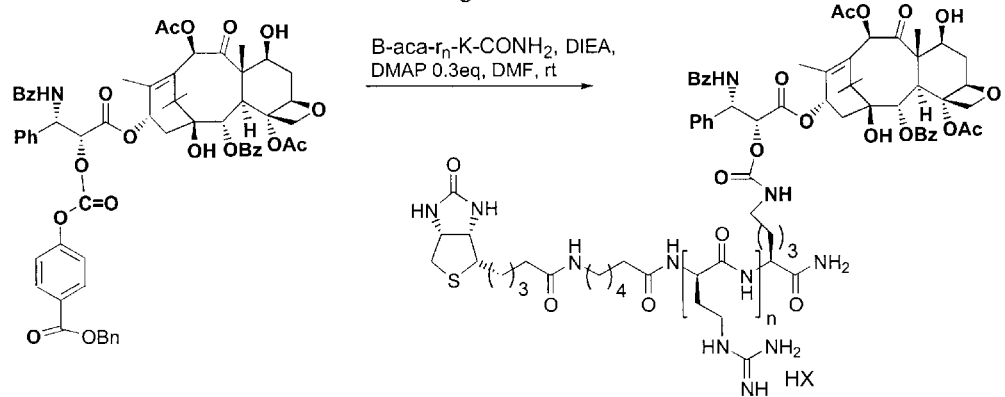
FIG. 13 shows a schematic of a reaction for coupling of a taxol derivative to a biotin-labeled peptide.

A procedure for coupling to biotin-labeled peptides is shown in FIG. 13. The taxol derivative and the biotin labeled peptide (1.2 equivalents) were dissolved in DMF (~10 µmol/mL DMF) under an $N_2$-atmosphere. Stock solutions of diisopropylethylamine (1.2 equivalents in DMF) and DMAP (0.3 equivalents in DMF) were added and stirring at room temperature was continued until all starting material was consumed. After 16 hours the solvent was removed in vacuo. The crude reaction mixture was dissolved in water and purified by RP-HPLC (eluent:water/MeCN*TFA) yielding the conjugates in the indicated yields:

B-aca-r5-K-taxol: 3.6 mg, 1.32 mmol, 20%.
B-aca-r7-K-taxol: 9.8 mg, 3.01 mmol, 44%.
B-aca-r9-K-taxol: 19.4 mg, 5.1 mmol, 67%.

Unlabeled C-2' Carbamates:

The taxol derivative (12.4 mg, 11.2 µmol) and the unlabeled peptide (27.1 mg, 13.4 µmol) were dissolved in DMF (1.5 mL) under an $N_2$-atmosphere (FIG. 14). Diisopropylethylamine (1.7 mg, 13.4 µmol) was added as a stock solution in DMF, followed by DMAP (0.68 mg, 5.6 µmol) as a stock solution in DMF. Stirring at room temperature was continued until all starting material was consumed. After 16 hours the solvent was removed in vacuo. The crude material was dissolved in water and purified by RP-HPLC (eluent:water/MeCN*TFA) yielding the desired product (16.5 mg, 5.9 µmol, 53%).

Other C-2' Conjugates

Figure 15A:
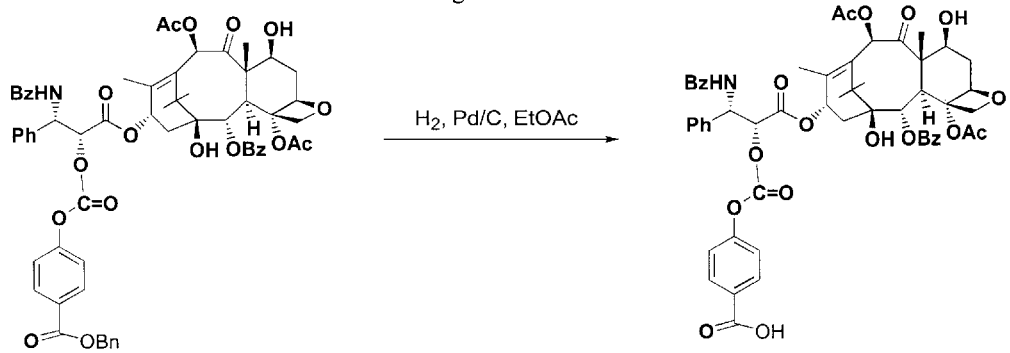
FIGS. 15A–C shows a reaction scheme for the formation of other C-2' taxol-peptide conjugates.

The taxol derivative (8.7 mg, 7.85 µmol) was dissolved in EtOAc (2.0 mL). Pd/C (10%, 4.0 mg) was added and the reaction flask was purged with $H_2$ five times (FIG. 15A). Stirring under an atmosphere of hydrogen was continued for 7 hours. The Pd/C was filtered and the solvent was removed in vacuo. The crude material (6.7 mg, 6.58 µmol, 84%) obtained in this way was pure and was used in the next step without further purification.

Figure 15B:
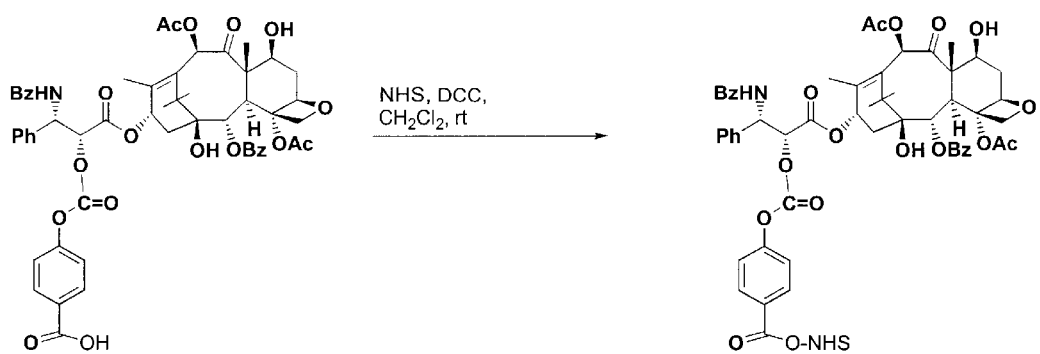

The free acid taxol derivative (18.0 mg, 17.7 µmol) was dissolved in $CH_2Cl_2$ (2.0 mL). Dicyclohexylcarbodiimide (4.3 mg, 21.3 µmol) was added as a stock solution in $CH_2Cl_2$ (0.1 mL). N-Hydroxysuccinimide (2.0 mg, 17.7 µmol) was added as a stock solution in DMF (0.1 mL) (FIG. 15B). Stirring at room temperature was continued for 14 hours. The solvent was removed in vacuo and the resultant crude material was purified by flash chromatography on silica gel (eluent: EtOAc/hexanes 40%–80%) yielding the desired product (13.6 mg, 12.2 µmol, 69%).

Figure 15C:
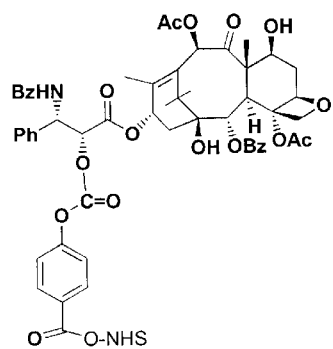
Figure 15C:
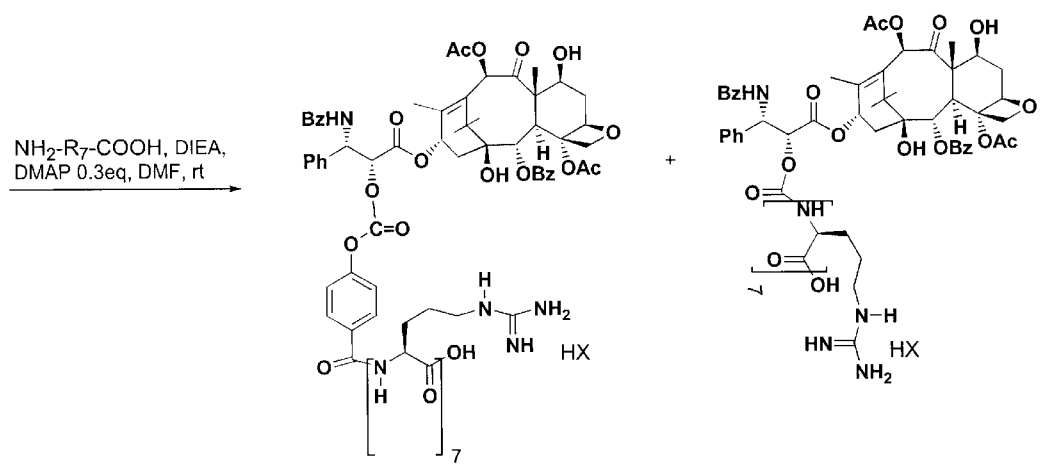

The activated taxol derivative (14.0 mg, 12.6 µmol) and the peptide (30.6 mg, 15.1 µmol) were dissolved in DMF (3.0 mL) under an $N_2$-atmosphere (FIG. 15C). Diisopropylethylamine (1.94 mg, 15.1 µmol) was added as a stock solution in DMF (0.1 mL), followed by DMAP (0.76 mg, 6.3 µmol) as a stock solution in DMF 0.1 mL). Stirring at room temperature was continued until all the starting material was consumed. After 20 hours the solvent was removed in vacuo. The crude material was dissolved in water and purified by RP-HPLC (eluent:water/MeCN*TFA) yielding the two depicted taxol conjugates in a ration of 1:6 (carbonate vs carbamate, respectively).

2. Analysis of Transport Across Skin

Varying concentrations (1 mM-100 µM) of taxol conjugated to either biotinylated pentamer, heptamer, or nonamers of D-arginine (bio r5, r7, or r9), dissolved in PBS, were applied to the back of nude mice. Samples (100 µl) were applied as a liquid within excipient and prevented from dispersing by a Vaseline™ barrier and allowed to penetrate for thirty, sixty, and 120 minutes. At the end of this period animal was sacrificed, the relevant section of skin was excised, embedded in mounting medium (OCT) and frozen. Frozen sections were cut using a cryostat, collected on slides, and stained with fluorescently labeled streptavidin (Vector Laboratories, Burlingame, Calif.) as described in Example 1. Slides were analyzed by fluorescent microscopy.

Results

The conjugates of taxol with biotinylated heptamers and nonamers of D-arginine effectively entered into and across the epidermis and into the dermis of the skin of nude mice. In contrast, very little uptake was seen using a conjugate between a pentamer of arginine and taxol, and no staining was seen with a PBS control. The cytosol and nuclei of all cells in the field were fluorescent, indicating penetration into and through the epidermis and dermis. The staining pattern was consistent with unanticipated transport that was both follicular and interfollicular. In addition, positive cells were apparent in papillary and reticular dermis. These results demonstrate remarkable uptake only when sufficient guanidinyl groups are included in the delivery-enhancing transporter.

Example 12

Conjugate of Taxol and Delivery-Enhancing Transporter with pH-Releasable Linker

Figure 16:
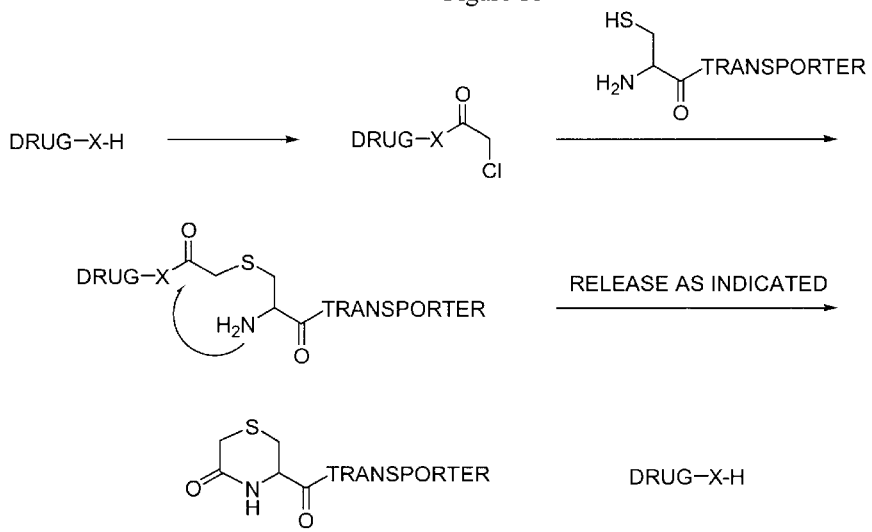
FIG. 16 shows a general strategy for synthesis of a conjugate in which a drug or other biological agent is linked to a delivery-enhancing transporter by a pH-releasable linker.
Figure 17:
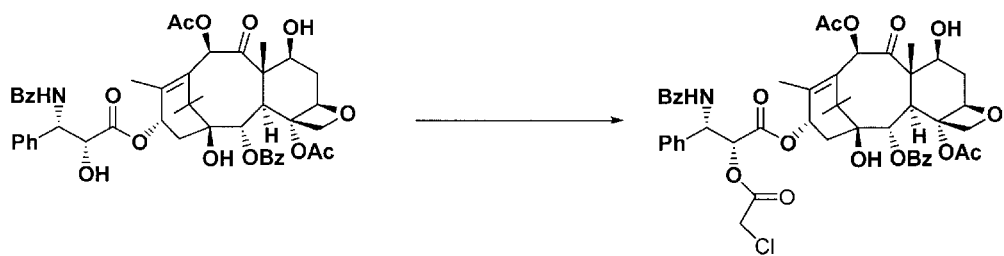
FIG. 17 shows a schematic diagram of a protocol for synthesizing a taxol 2'-chloroacetyl derivative.

This Example demonstrates the use of a general strategy for synthesizing prodrugs that have a delivery-enhancing transporter linked to a drug by a linker that releases the drug from the delivery-enhancing transporter upon exposure to physiological pH. In general, a suitable site on the drug is derivatized to carry an α-chloroacetyl residue. Next, the chlorine is displaced with the thiol of a cysteine residue that carries an unprotected amine. This scheme is shown in FIG. 16.

Methods

Synthesis of Taxol-2'-chloroacetyl

Figure 18:
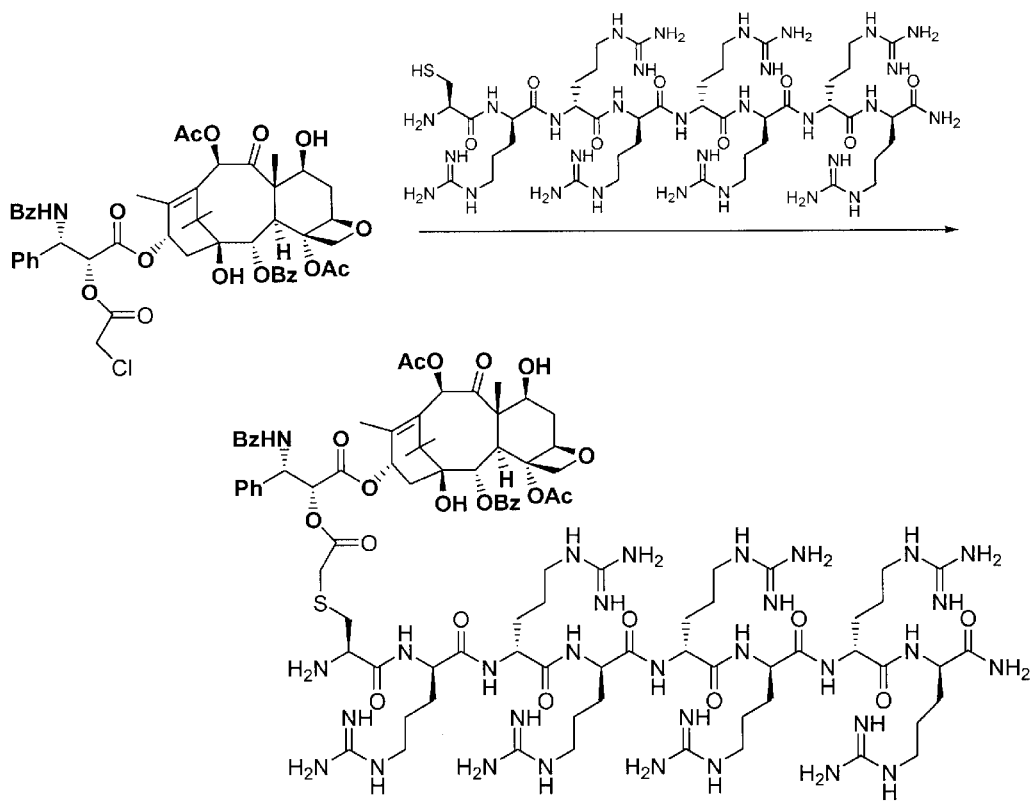
FIG. 18 shows a strategy by which a taxol 2'-chloroacetyl derivative is linked to an arginine heptamer delivery-enhancing transporter.

Taxol (89.5 mg, 104.9 µmol) was dissolved in $CH_2Cl_2$ (3.5 mL). The solution was cooled to 0° C. under an $N_2$-atmosphere. α-Chloroacetic anhydride (19.7 mg, 115.4 µmol) was added, followed by DIEA (14.8 mg, 115.4 µmol). The solution was allowed to warm to room temperature. After thin layer chromatography (tlc) analysis indicated complete consumption of starting material, the solvent was removed in vacuo and the crude material was purified by flash chromatography on silica gel (eluent: EtOAC/Hex 20%–50%) yielding the desired material (99.8 mg, quantitative) (FIG. 18).

$^1$H-NMR ($CDCl_3$): δ=8.13 (d, J=7.57 Hz, 2H), 7.72 (d, J=7.57 Hz, 2H), 7.62–7.40 (m, 11H), 6.93 (d, J=9.14 Hz, 1H), 6.29-6.23 (m, 2H), 6.01 (d, J=7.14 Hz, 1H), 5.66 (d, J=6.80 Hz, 1H), 5.55 (d, J=2.24 Hz, 1H), 4.96 (d, J=8.79 Hz, 1H), 4.43 (m, 1H), 4.30 (d, J=8.29 Hz, 1H), 4.20-4.15 (m, 2H), 3.81 (d, J=6.71 Hz, 1H), 2.56-2.34 (m, 3H), 2.45 (s, 3H), 2.21 (s, 3H), 2.19 (m, 1H), 1.95-1.82 (m, 3H), 1.92 s, (3H), 1.67 (s, 3H), 1.22 (s, 3H), 1.13 (s, 3H) ppm.

$^{13}$C-NMR ($CDCl_3$): δ=203.6, 171.1, 169.7, 167.3, 167.0, 166.9, 166.3, 142.3, 136.4, 133.6, 133.5, 132.9, 132.0, 130.1, 129.2, 121.1, 128.7, 128.6, 127.0, 126.5, 84.3, 81.0, 79.0, 76.3, 75.4, 75.2, 75.0, 72.2, 72.0, 58.4, 52.7, 45.5, 43.1, 40.1, 35.5, 26.7, 22.6, 22.0, 20.7, 14.7, 9.5 ppm.

Linkage of Taxol to Delivery-Enhancing Transporter

The peptide (47.6 mg, 22.4 µmol) was dissolved in DMF (1.0 mL) under an $N_2$-atmosphere. DIEA (2.8 mg, 22.4 µmol) was added. A solution of taxol-2'-chloroacetate (20.8 mg, 22.4 µmol) in DMF (1.0 mL) was added. Stirring at room temperature was continued for 6 hours. Water containing 0.1% TFA (1.0 mL) was added, the sample was frozen and the solvents were lyophilized. The crude material was purified by RP-HPLC (eluent:water/MeCN*0.1%TFA: 85%-15%). A schematic of this reaction is shown in FIG. 18.

Synthesis of Related Conjugates

Using the conjugation conditions outlined above, the three additional conjugates shown in were synthesized.

Cytotoxicity Assay

Figure 19:
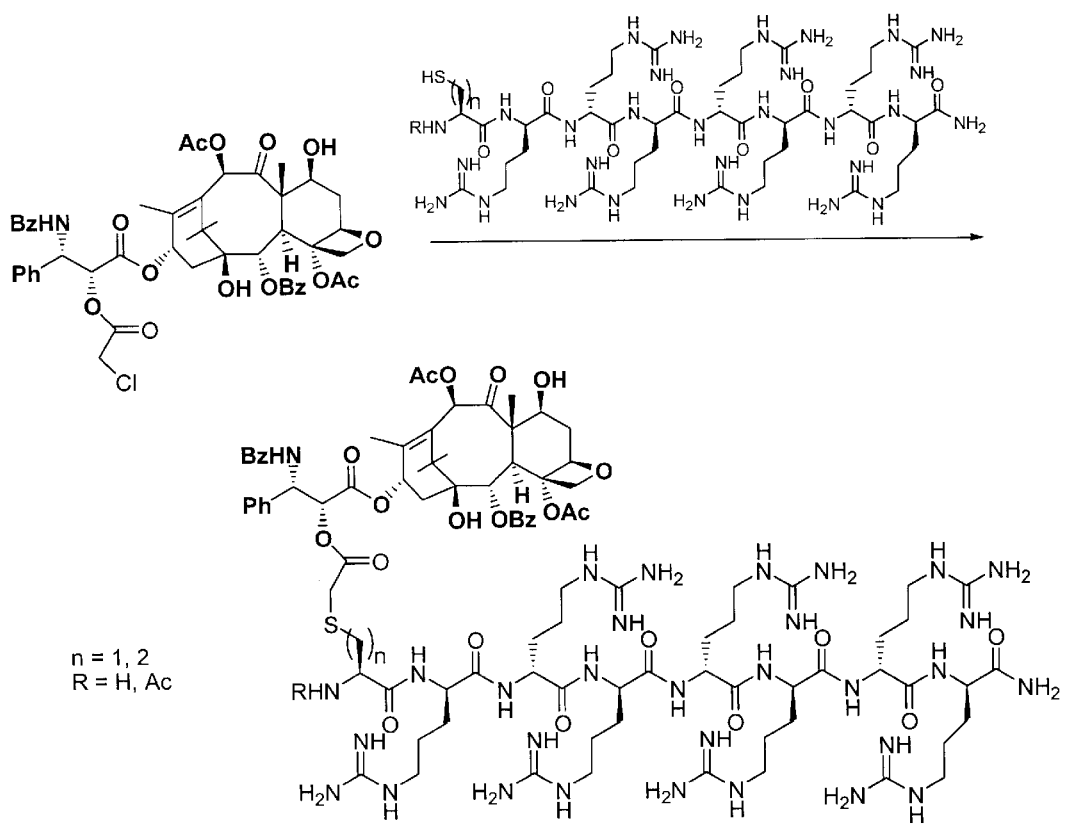
FIG. 19 shows three additional taxol-r7 conjugates that can be made using the reaction conditions illustrated in FIG. 18.
Figure 20:
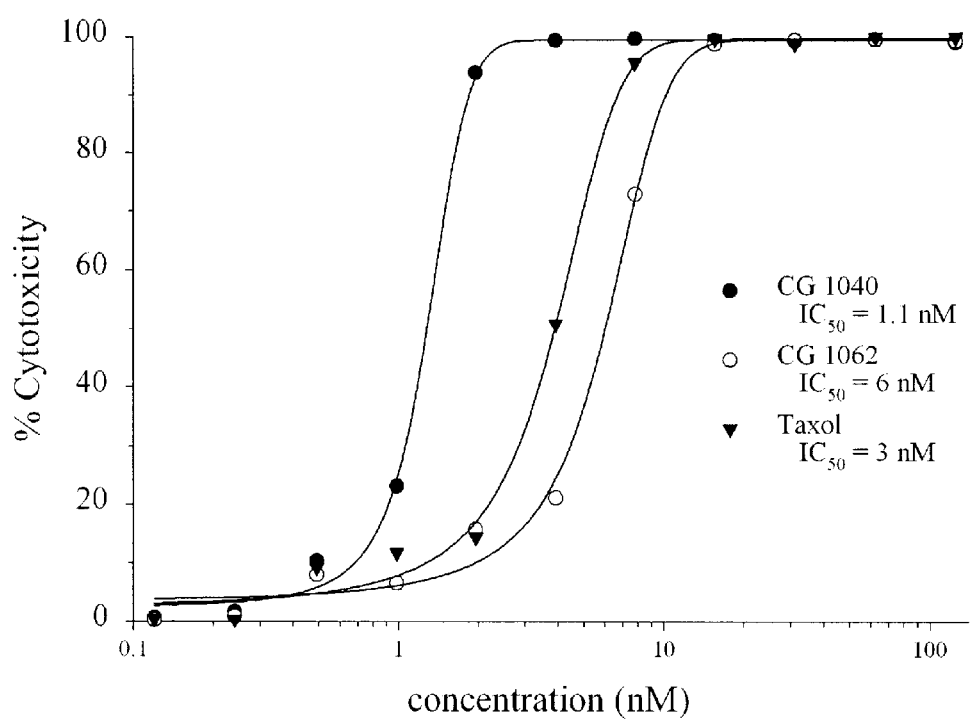
FIG. 20 shows the results of a 3 day MTT cytotoxicity assay using taxol and two different linkers.
Figure 21:
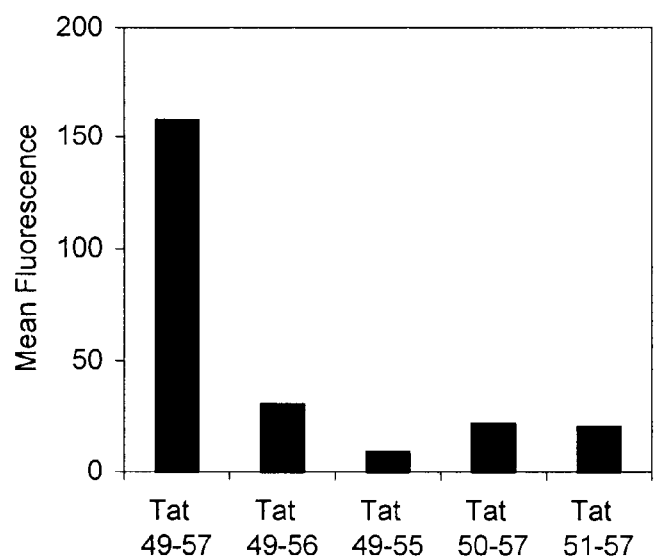
FIG. 21: FACS cellular uptake assay of truncated analogs of $Tat_{49-57}$ (F1-ahx-RKKRRQRRR; SEQ ID NO:8): $Tat_{49-56}$ (F1-ahx-RKKRRQRR; SEQ ID NO:9), $Tat_{49-55}$ (F1-ahx-RKKRRQR; SEQ ID NO:10), $Tat_{50-57}$ (F1-ahx-KKRRQRRR; SEQ ID NO:11), and $Tat_{51-57}$ (F1-ahx-KRRQRRR; SEQ ID NO:12). Jurkat cells were incubated with varying concentrations (12.5 μM shown) of peptides for 15 mm at 23° C.

The taxol conjugates were tested for cytotoxicity in a 3-(4,5-dimethylthiazol-2-yl)-2,5-diphenyl-tetrazolium-bromide (MTT) dye reduction. Results, which are shown in FIG. 20, demonstrate that the taxol conjugated to r7 with a readily pH-releasable linker (CG 1062; R=Ac in the structure shown in FIG. 19) is significantly more cytotoxic than either taxol alone or taxol conjugated to r7 with a less-readily pH-releasable linker (CG 1040; R=H in the structure shown in FIG. 19).

Example 13

Structure-Function Relationships of Fluorescently-Labeled Peptides Derived from $Tat_{49-57}$ Methods General.

Rink amide resin and $Boc_2O$ were purchased from Novabiochem. Diisopropylcarbodiimide, bromoacetic acid, fluorescein isothiocyanate (FITC-NCS), ethylenediamine, 1,3-diaminopropane, 1,4-diaminobutane, 1,6-diaminohexane, trans-1,6-diaminocyclohexane, and pyrazole-1-carboxamidine were all purchased from Aldrich®. All solvents and other reagents were purchased from commercial sources and used without further purification. The mono-Boc amines were synthesized from the commercially available diamines using a literature procedure (10 equiv. of diamine and 1 equiv. of $Boc_2O$ in chloroform followed by an aqueous work up to remove unreacted diamine) (34).

N-tert-butoxycarbonyl-1,6-trans-diaminocyclohexane.

Mp 159–161° C.; $^1$H NMR ($CDCl_3$) δ 4.35 (br s, 1H), 3.37 (br s, 1H), 2.61 (br s, 1H), 1.92–2.02 (m, 2H), 1.81–1.89 (m, 2H), 1.43 (s, 9H), 1.07–1.24 (m, 4H) ppm; $^{13}$C NMR ($D_6$-DMSO) δ 154.9, 77.3, 49.7, 48.9, 35.1, 31.4, 28.3 ppm; ES-MS (M+1) calcd 215.17, found 215.22.

General Procedure for Peptide Synthesis. $Tat_{49-57}$ (RKKRRQRRR; SEQ ID NO:28), truncated and alanine-substituted peptides derived from $Tat_{49-57}$, Antennapedia$_{43-58}$ (RQIKIWFQNRRMKWKKK SEQ ID NO:29), and homopolymers of arginine (R5–R9; SEQ ID NOS:1–5) and d-arginine (r5–r9) were prepared with an automated peptide synthesizer (ABI433) using standard solid-phase Fmoc chemistry (35) with HATU as the peptide coupling reagent. The fluorescein moiety was attached via a aminohexanoic acid spacer by treating a resin-bound peptide (1.0 mmol) with fluorescein isothiocyanate (1.0 mmol) and DIBA (5 mmol) in DMF (10 mL) for 12 h. Cleavage from the resin was achieved using 95:5 TFA/triisopropylsilane. Removal of the solvent in vacuo gave a crude oil which was triturated with cold ether. The crude mixture thus obtained was centrifuged, the ether was removed by decantation, and the resulting orange solid was purified by reverse-phase HPLC ($H_2O/CH_3CN$ in 0.1% TFA). The products were isolated by lyophilization and characterized by electrospray mass spectrometry. Purity of the peptides was >95% as determined by analytical reverse-phase HPLC ($H_2O/CH_3CN$ in 0.1% TFA).

All peptides and peptoids synthesized contain an aminohexanoic (ahx) acid moiety attached to the N-terminal amino group with a fluorescein moiety (Fl) covalently linked to the amino group of the aminohexanoic acid spacer. The carboxyl terminus of every peptide and peptoid is a carboxamide.

Cellular Uptake Assay.

The arginine homopolymers and guanidine-substituted peptoids were each dissolved in PBS buffer (pH 7.2) and their concentration was determined by absorption of fluorescein at 490 nm (ε=67,000). The accuracy of this method for determining concentration was established by weighing selected samples and dissolving them in a known amount of PBS buffer. The concentrations determined by UV spectroscopy correlated with the amounts weighed out manually. Jurkat cells (human T cell line), murine B cells (CH27), or human PBL cells were grown in 10% fetal calf serum and DMEM and each of these were used for cellular uptake experiments. Varying amounts of arginine and oligomers of guanidine-substituted peptoids were added to approximately $3 \times 10^6$ cells in 2% FCS/PBS (combined total of 200 µL) and placed into microtiter plates (96 well) and incubated for varying amounts of time at 23° C. or 4° C. The microtiter plates were centrifuged and the cells were isolated, washed with cold PBS (3×250 µL), incubated with 0.05% trypsin/0.53 mM EDTA at 37° C. for 5 min, washed with cold PBS, and resuspended in PBS containing 0.1% propidium iodide. The cells were analyzed using fluorescent flow cytometry (FACScan, Becton Dickinson) and cells staining with propidium iodide were excluded from the analysis. The data presented is the mean fluorescent signal for the 5000 cells collected.

Inhibition of Cellular Uptake with Sodium Azide. The assays were performed as previously described with the exception that the cells used were preincubated for 30 min with 0.5% sodium azide in 2% FCS/PBS buffer prior to the addition of fluorescent peptides and the cells were washed with 0.5% sodium azide in PBS buffer. All of the cellular uptake assays were run in parallel in the presence and absence of sodium azide.

Cellular Uptake Kinetics Assay. The assays were performed as previously described except the cells were incubated for 0.5, 1, 2, and 4 min at 4° C. in triplicate in 2% FCS/PBS (50 μl) in microtiter plates (96 well). The reactions were quenched by diluting the samples into 2% FCS/PBS (5 mL). The assays were then worked up and analyzed by fluorescent flow cytometry as previously described.

Results

To determine the structural requirements for the cellular uptake of short arginine-rich peptides, a series of fluorescently-labeled truncated analogues of $Tat_{49-57}$ were synthesized using standard solid-phase chemistry. See, e.g., Atherton, E. et al. SOLID-PHASE PEPTIDE SYNTHESIS (IRL: Oxford, Engl. 1989). A fluorescein moiety was attached via an aminohexanoic acid spacer on the amino termini. The ability of these fluorescently labeled peptides to enter Jurkat cells was then analyzed using fluorescent activated cell sorting (FACS). The peptide constructs tested were $Tat_{49-57}$ (Fl-ahx-RKKRRQRRR; SEQ ID NO:8): $Tat_{49-56}$ (Fl-ahx-RKKRRQRR; SEQ ID NO:9), $Tat_{49-55}$ (Fl-ahx-RKKRRQR; SEQ ID NO: 10), $Tat_{50-57}$ (Fl-ahx-KKRRQRRR; SEQ ID NO: 11), and $Tat_{51-57}$ (Fl-ahx-KRRQRRR; SEQ ID NO: 12). Differentiation between cell surface binding and internalization was accomplished throughout by running a parallel set of assays in the presence and absence of sodium azide. Because sodium azide inhibits energy-dependent cellular uptake but not cell surface binding, the difference in fluorescence between the two assays provided the amount of fluorescence resulting from internalization.

Deletion of one arginine residue from either the amine terminus ($Tat_{50-57}$) or the carboxyl terminus ($Tat_{49-56}$) resulted in an 80% loss of intracellular fluorescence compared to the parent sequence ($Tat_{49-57}$). From the one amino acid truncated analogs, further deletion of R-56 from the carboxyl terminus ($Tat_{49-55}$) resulted in an additional 60% loss of intracellular fluorescence, while deletion of K-50 from the amine terminus ($Tat_{51-57}$) did not further diminish the amount of internalization. These results indicate that truncated analogs of $Tat_{49-57}$ are significantly less effective at the transcellular delivery of fluorescein into Jurkat cells, and that the arginine residues appear to contribute more to cellular uptake than the lysine residues.

Figure 22:
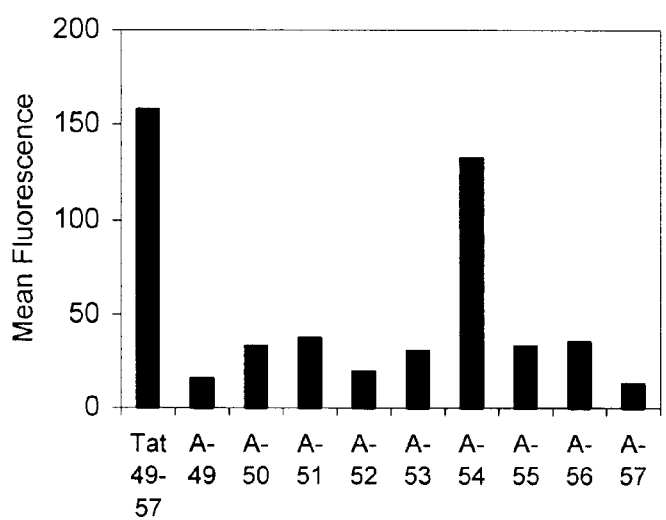
FIG. 22 shows FAGS cellular uptake assay of alanine-substituted analogs of $Tat_{49-57}$: A-49 (F1-ahx-AKKRRQRRR; SEQ ID NO:13), A-50 (F1-ahx-RAKRRQRRR; SEQ ID NO:14), A-51 (F1-ahx-RKARRQRRR; SEQ ID NO:15), A-52 (F1-ahx-RKKARQRRR; SEQ ID NO:16), A-53 (F1-ahx-RKKRAQRRR; SEQ ID NO:17), A-54 (F1-ahx-RKKRRARRR; SEQ ID NO:18), A-55 (F1-ahx-RKKRRQARR; SEQ ID NO:19), A-56 (F1-ahx-RKKRRQRAR; SEQ ID NO:20), and A-57 (F1-ahx-RKKRRQRRA; SEQ ID NO:21). Jurkat cells were incubated with varying concentrations (12.5 μM shown) of peptides for 12 mm at 23° C.

To determine the contribution of individual amino acid residues to cellular uptake, analogs containing alanine substitutions at each site of $Tat_{49-57}$ were synthesized and assayed by FACS analysis (FIG. 22). The following constructs were tested: A-49 (Fl-ahx-AKKRRQRRR; SEQ ID NO:13), A-50 (Fl-ahx-RAKRRQRRR; SEQ ID NO:14), A-51 (Fl-ahx-RKARRQRRR; SEQ ID NO:15), A-52 (Fl-ahx-RKKARQRRR; SEQ ID NO:16), A-53 (Fl-ahx-RKKRAQRRR; SEQ ID NO:17), A-54 (Fl-ahx-RKKRRARRR; SEQ ID NO:18), A-55 (Fl-ahx-RKKKRRQARR; SEQ ID NO:19), A-56 (Fl-ahx-RKKRRQRAR; SEQ ID NO:20), and A-57 (Fl-ahx-RKKRRQRRA; SEQ ID NO:21). Substitution of the non-charged glutamine residue of $Tat_{49-57}$ with alanine (A-54) resulted in a modest decrease in cellular internalization. On the other hand, alanine substitution of each of the cationic residues individually produced a 70–90% loss of cellular uptake. In these cases, the replacement of lysine (A-50, A-51) or arginine (A-49, A-52, A-55, A-56, A-57) with alanine had similar effects in reducing uptake.

Figure 23:
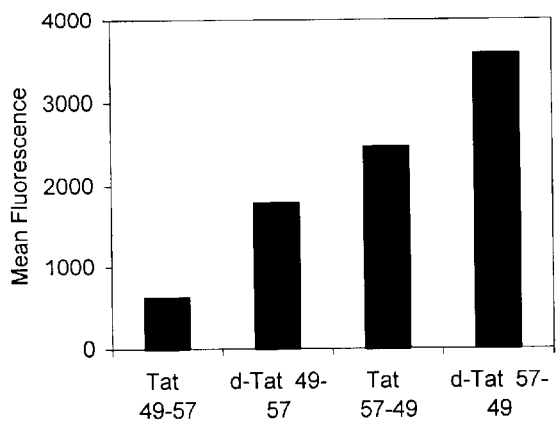
FIG. 23: FAGS cellular uptake assay of d- and retro-isomers of $Tat_{49-57}$: d-$Tat_{49-57}$ (F1-ahx-rkkrrqrrr), $Tat_{57-49}$ (F1-ahx-RRRQRRKKR; SEQ ID NO:22), and d-$Tat_{57-49}$ (F1-ahx-rrrqrrkkr). Jurkat cells were incubated with varying concentrations (12.5 μM shown) of peptides for 15 min at 23° C.

To determine whether the chirality of the transporter peptide was important, the corresponding d-(d-$Tat_{49-57}$), retro-l-($Tat_{57-49}$), and retro-inverso isomers (d-$Tat_{57-49}$) were synthesized and assayed by FACS analysis (FIG. 23).

Importantly, all three analogs were more effective at entering Jurkat cells then $Tat_{49-57}$. These results indicated that the chirality of the peptide backbone is not crucial for cellular uptake. Interestingly, the retro-l isomer ($Tat_{57-49}$) which has three arginine residues located at the amine terminus instead of one arginine and two lysines found in $Tat_{49-57}$ demonstrated enhanced cellular uptake. Thus, residues at the amine terminus appear to be important and that arginines are more effective than lysines for internalization. The improved cellular uptake of the unnatural d-peptides is most likely due to their increased stability to proteolysis in 2% FCS (fetal calf serum) used in the assays. When serum was excluded, the d- and l-peptides were equivalent as expected.

Figure 24:
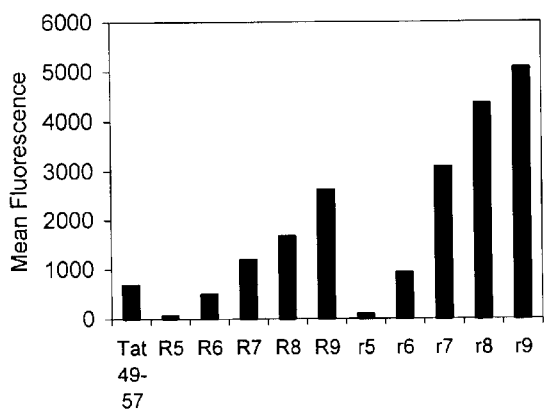
FIG. 24: FAGS cellular uptake of a series of arginine oligomers and $Tat_{49-57}$: R5 (F1-ahx-RRRRR; SEQ ID NO:23), R6 (F1-ahx-RRRRRR; SEQ ID NO:24), R7 (F1-ahx-RRRRRRR; SEQ ID NO:25), R8 (F1-ahx-RRRRRRRR; SEQ ID NO:26), R9 (F1-ahx-RRRRRRRRR; SEQ ID NO:27), r5 (F1-ahx-rrrrr), r6 (F1-ahx-rrrrrr), r7 (F1-ahx-rrrrrrr), r8 (F1-ahx-rrrrrrrr), r9 (F1-ahx-rrrrrrrrr). Jurkat cells were incubated with varying concentrations (12.5 μM shown) of peptides for 4 mm at 23° C.

These initial results indicated that arginine content is primarily responsible for the cellular uptake of $Tat_{49-57}$. Furthermore, these results were consistent with our previous results where we demonstrated that short oligomers of arginine were more effective at entering cells then the corresponding short oligomers of lysine, ornithine, and histidine. What had not been established was whether arginine homo-oligomers are more effective than $Tat_{49-57}$. To address this point, $Tat_{49-57}$ was compared to the l-arginine (R5–R9) and d-arginine (r5–r9) oligomers. Although $Tat_{49-57}$ contains eight cationic residues, its cellular internalization was between that of R6 and R7 (FIG. 24) demonstrating that the presence of six arginine residues is the most important factor for cellular uptake. Significantly, conjugates containing 7–9 arginine residues exhibited better uptake than $Tat_{49-57}$.

To quantitatively compare the ability of these arginine oligomers and $Tat_{49-57}$ to enter cells, Michaelis-Menton kinetic analyses were performed. The rates of cellular uptake were determined after incubation (3° C.) of the peptides in Jurkat cells for 30, 60, 120, and 240 seconds (Table 1). The resultant $K_m$ values revealed that r9 and R9 entered cells at rates approximately 100-fold and 20-fold faster than $Tat_{47-59}$ respectively. For comparison, $Antennapedia_{43-58}$ was also analyzed and was shown to enter cells approximately 2-fold faster than $Tat_{47-59}$, but significantly slower than r9 or R9.

TABLE 1

Michaelis-Menton kinetics: $Antennapedia_{43-58}$ (Fl-ahx-RQIKIWFQNRRMKWKK; SEQ ID NO:30).

| peptide | $K_m$ (μM) | $V_{max}$ |
|---|---|---|
| $Tat_{49-57}$ | 770 | 0.38 |
| $Antennapedia_{43-58}$ | 427 | 0.41 |
| R9 | 44 | 0.37 |
| r9 | 7.6 | 0.38 |

Example 14

Design and Synthesis of Peptidomimetic Analogs of $Tat_{49-57}$

Methods

General Procedure for Peptoid Polyamine Synthesis. Peptoids were synthesized manually using a fritted glass apparatus and positive nitrogen pressure for mixing the resin following the literature procedure developed by Zuckermann. See, e.g., Murphy, J. E. et al., Proc. Natl. Acad. Sci. USA 95, 1517–1522 (1998); Simon, R. J. et al., Proc. Natl. Acad. Sci. USA 89, 9367–9371 (1992); Zuckermann, R. N. et al., J. Am. Chem. Soc. 114, 10646–10647 (1992). Treatment of Fmoc-substituted Rink amide resin (0.2 mmol) with 20% piperidine/DMF (5 mL) for 30 min (2×) gave the free resin-bound amine which was washed with DMF (3×5 mL). The resin was treated with a solution of bromoacetic acid (2.0 mmol) in DMF (5 mL) for 30 min. This procedure was repeated. The resin was then washed (3×5 mL DMF) and treated with a solution of mono-Boc diamine (8.0 mmol) in DMF (5 mL) for 12 hrs. These two steps were repeated until an oligomer of the required length was obtained (Note: the solution of mono-Boc diamine in DMF could be recycled without appreciable loss of yield). The resin was then treated with N-Fmoc-aminohexanoic acid (2.0 mmol) and DIC (2.0 mmol) in DMF for 1 h and this was repeated. The Fmoc was then removed by treatment with 20% piperidine/DMF (5 mL) for 30 min. This step was repeated and the resin was washed with DMF (3×5 mL). The free amine resin was then treated with fluorescein isothiocyanate (0.2 mmol) and DIEA (2.0 mmol) in DMF (5 mL) for 12 hrs. The resin was then washed with DMF (3×5 mL) and dichloromethane (5×5 mL). Cleavage from the resin was achieved using 95:5 TFA/triisopropylsilane (8 mL). Removal of the solvent in vacuo gave a crude oil which was triturated with cold ether (20 mL). The crude mixture thus obtained was centrifuged, the ether was removed by decantation, and the resulting orange solid was purified by reverse-phase HPLC ($H_2O$/$CH_3CN$ in 0.1% TFA). The products were isolated by lyophilization and characterized by electrospray mass spectrometry and in selected cases by $^1H$ NMR spectroscopy.

General Procedure for Perguanidinylation of Peptoid Polyamines. A solution of peptoid amine (0.1 mmol) dissolved in deionized water (5 mL) was treated with sodium carbonate (5 equivalents per amine residue) and pyrazole-1-carboxamidine (5 equivalents per amine residue) and heated to 50° C. for 24–48 hr. The crude mixture was then acidified with TFA (0.5 mL) and directly purified by reverse-phase HPLC ($H_2O$/$CH_3CN$ in 0.1% TFA). The products were characterized by electrospray mass spectrometry and isolated by lyophilization and further purified by reverse-phase HPLC. The purity of the guanidine-substituted peptoids was >95% as determined by analytical reverse-phase HPLC ($H_2O$/$CH_3CN$ in 0.1% TFA).

Results

Utilizing the structure-function relationships that had been determined for the cellular uptake of $Tat_{47-59}$, we designed a set of polyguanidine peptoid derivatives that preserve the 1,4 backbone spacing of side chains of arginine oligomers, but have an oligo-glycine backbone devoid of stereogenic centers. These peptoids incorporating arginine-like side chains on the amide nitrogen were selected because of their expected resistance to proteolysis, and potential ease and significantly lower cost of synthesis (Simon et al., *Proc. Natl. Acad. Sci. USA* 89:9367–9371 (1992); Zuckermann, et al., *J. Am. Chem. Soc.* 114:10646–10647 (1992). Furthermore, racemization, frequently encountered in peptide synthesis, is not a problem in peptoid synthesis; and the "sub-monomer" peptoid approach allows for facile modification of side-chain spacers. Although the preparation of an oligurea and peptoid-peptide hybrid (Hamy, et al, *Proc. Natl. Acad. Sci. USA* 94:3548–3553 (1997)) derivatives of $Tat_{49-57}$ have been previously reported, their cellular uptake was not explicitly studied.

Figure 25:
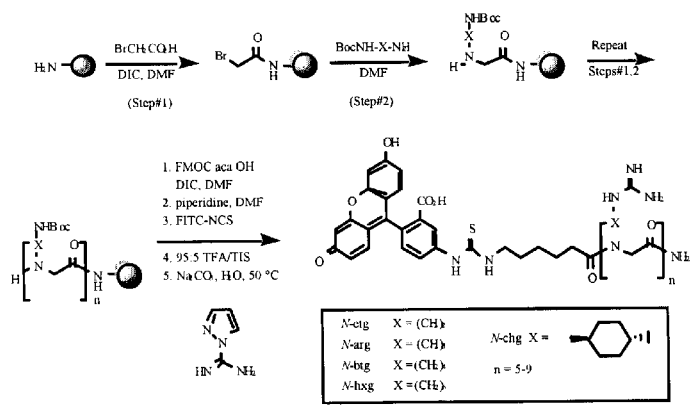
FIG. 25 displayes the preparation of guanidine-substituted peptoids.

The desired peptoids were prepared using the "sub-monomer" approach (Simon et al.; Zuckermann et al.) to peptoids followed by attachment of a fluorescein moiety via an aminohexanoic acid spacer onto the amine termini. After cleavage from the solid-phase resin, the fluorescently labeled polyamine peptoids thus obtained were converted in good yields (60–70%) into polyguanidine peptoids by treatment with excess pyrazole-1-carboxamidine (Bernatowicz, et al., *J. Org. Chem.* 57:2497–2502 (1992) and sodium carbonate (as shown in FIG. 25). Previously reported syntheses of peptoids containing isolated N-Arg units have relied on the synthesis of N-Arg monomers (5–7 steps) prior to peptoid synthesis and the use of specialized and expensive guanidine protecting groups (Pmc, Pbf) (Kruijtzer, et al., *Chem. Eur. J.* 4:1570–1580 (1998); Heizmann, et al. *Peptide Res.* 7:328–332 (1994). The compounds reported here represent the first examples of polyguanidinylated peptoids prepared using a perguanidinylation step. This method provides easy access to polyguanidinylated compounds from the corresponding polyamines and is especially useful for the synthesis of perguanidinylated homooligomers. Furthermore, it eliminates the use of expensive protecting groups (Pbf, Pmc). An additional example of a perguanidinylation of a peptide substrate using a novel triflyl-substituted guanylating agent has recently been reported (Feichtinger, et al., *J. Org. Chem.* 63:8432–8439 (1998)).

Figure 26:
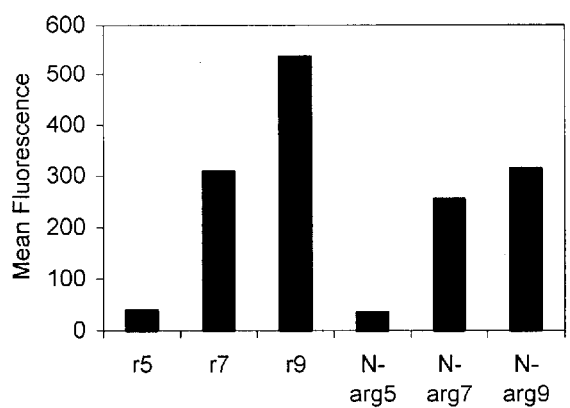
FIG. 26 displays the FACS cellular uptake of polyguanidine peptoids and d-arginine oligomers. Jurkat cells were incubated with varying concentrations (12.5 μM shown) of peptoids and peptides for 4 min at 23° C.

The cellular uptake of fluorescently labeled polyguanidine N-arg5,7,9 peptoids was compared to the corresponding d-arginine peptides r5,7,9 (similar proteolytic properties) using Jurkat cells and FACS analysis. The amount of fluorescence measured inside the cells with N-arg5,7,9 was proportional to the number of guanidine residues: N-arg9 >N-arg7 >N-arg5 (FIG. 26), analogous to that found for r5,7,9. Furthermore, the N-arg5,7,9 peptoids showed only a slightly lower amount of cellular entry compared to the corresponding peptides, r5,7,9. The results demonstrate that the hydrogen bonding along the peptide backbone of $Tat_{49-57}$ or arginine oligomers is not a required structural element for cellular uptake and oligomeric guanidine-substituted peptoids can be utilized in place of arginine-rich peptides as molecular transporters. The addition of sodium azide inhibited internalization demonstrating that the cellular uptake of peptoids was also energy dependent.

Example 15

The effect of Side Chain Length on Cellular Uptake

Figure 27:
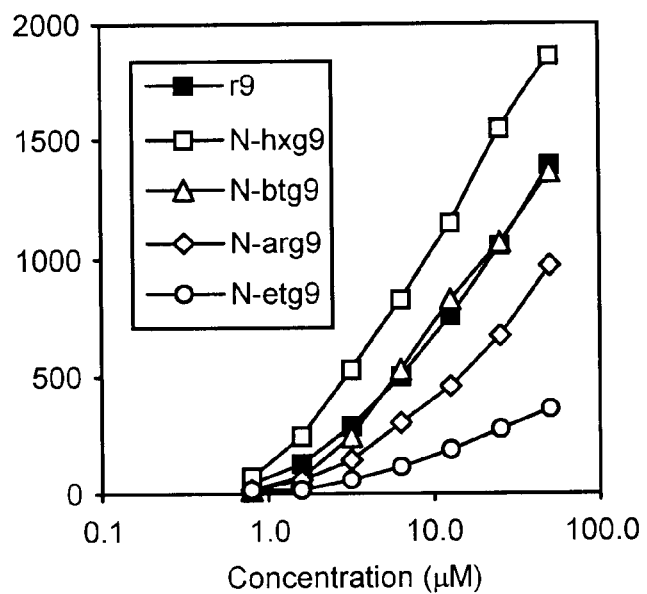
FIG. 27 displays the FACS cellular uptake of d-arginine oligomers and polyguanidine peptoids. Jurkat cells were incubated with varying concentrations (12.5 μM shown) of fluorescently labeled peptoids and peptides for 4 min at 23° C.
Figure 28:
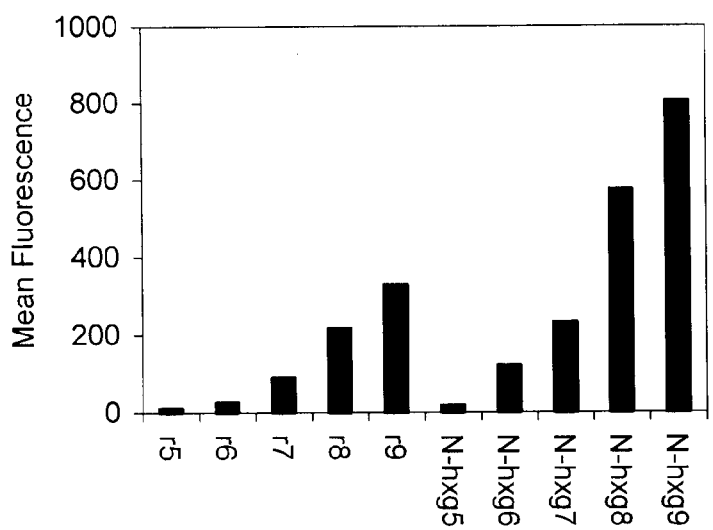
FIG. 28 displays the FACS cellular uptake of and d-arginine oligomers and N-hxg peptoids. Jurkat cells were incubated with varying concentrations (6.3 μM shown) of fluorescently labeled peptoids and peptides for 4 min at 23° C.

After establishing that the N-arg peptoids efficiently crossed cellular membranes, the effect of side chain length (number of methylenes) on cellular uptake was investigated. For a given number of guanidine residues (5, 7, 9), cellular uptake was proportional to side chain length. Peptoids with longer side chains exhibited more efficient cellular uptake. A nine-mer peptoid analog with a six-methylene spacer between the guanidine head groups and the backbone (N-hxg9) exhibited remarkably higher cellular uptake than the corresponding d-arginine oligomer (r9). The relative order of uptake was N-hxg9 (6 methylene)>N-btg9 (4 methylene)>r9 (3 methylene)>N-arg9 (3 methylene)>N-etg9 (2 methylene) (FIG. 27). Of note, the N-hxg peptoids showed remarkably high cellular uptake, even greater than the corresponding d-arginine oligomers. The cellular uptake of the corresponding heptamers and pentamers also showed the same relative trend. The longer side chains embodied in the N-hxg peptoids improved the cellular uptake to such an extent that the amount of internalization was comparable to the corresponding d-arginine oligomer containing one more guanidine residue (FIG. 28). For example, the N-hxg7 peptoid showed comparable cellular uptake to r8.

Figure 29:
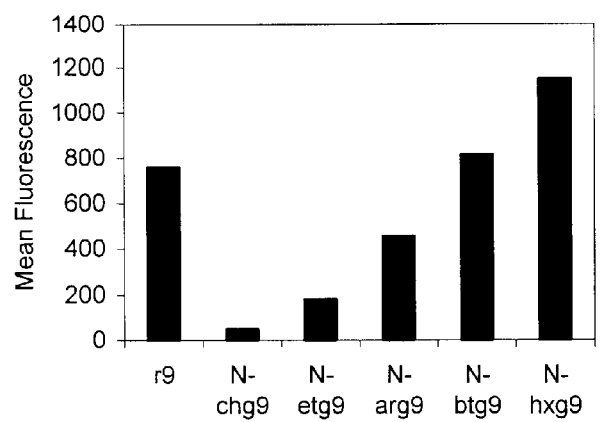
FIG. 29 shows the FACS cellular uptake of d-arginine oligomers and N-chg peptoids. Jurkat cells were incubated with varying concentrations (12.5 μM shown) of fluorescently labeled peptoids and peptides for 4 min at 23° C.

To address whether the increase in cellular uptake was due to the increased length of the side chains or due to their hydrophobic nature, a set of peptoids was synthesized containing cyclohexyl side chains. These are referred to as the N-chg5,7,9 peptoids. These contain the same number of side chain carbons as the N-hxg peptoids but possess different degrees of freedom. Interestingly, the N-chg peptoid showed much lower cellular uptake activity than all of the previously assayed peptoids, including the N-etg peptoids (FIG. 29). Therefore, the conformational flexibility and sterically unencumbered nature of the straight chain alkyl spacing groups is important for efficient cellular uptake.

Discussion

The nona-peptide, $Tat_{49-57}$, has been previously shown to efficiently translocate through plasma membranes. The goal of this research was to determine the structural basis for this effect and use this information to develop simpler and more effective molecular transporters. Toward this end, truncated and alanine substituted derivatives of $Tat_{49-57}$ conjugated to a fluoroscein label was prepared. These derivatives exhibited greatly diminished cellular uptake compared to $Tat_{49-57}$, indicating that all of the cationic residues of $Tat_{49-57}$ are required for efficient cellular uptake. When compared with our previous studies on short oligomers of cationic oligomers, these findings suggested that an oligomer of arginine might be superior to $Tat_{49-57}$ and certainly more easily and cost effectively prepared. Comparison of short arginine oligomers with $Tat_{49-57}$ showed that members of the former were indeed more efficiently taken into cells. This was further quantified for the first time bt Michaelis-Menton kinetics analysis which showed that the R9 (SEQ ID NO:5) and r9 oligomers had Km values 30-fold and 100-fold greater than that found for $Tat_{49-57}$.

Given the importance of the guanidino head group and the apparent insensitivity of the oligomer chirality revealed in our peptide studies, we designed and synthesized a novel series of polyguanidine peptoids. The peptoids N-arg5,7,9, incorporating the arginine side chain, exhibited comparable cellular uptake to the corresponding d-arginine peptides r5,7,9, indicating that the hydrogen bonding along the peptide backbone and backbone chirality are not essential for cellular uptake. This observation is consistent with molecular models of these peptoids, arginine oligomers, and $Tat_{49-57}$, all of which have a deeply embedded backbone and a guanidinium dominated surface. Molecular models further reveal that these structural characteristics are retained in varying degree in oligomers with different alkyl spacers between the peptoid backbone and guanidino head groups. Accordingly, a series of peptoids incorporating 2-(N-etg), 4-(N-btg), and 6-atom (N-hxg) spacers between the backbone and side chain were prepared and compared for cellular uptake with the N-arg peptoids (3-atom spacers) and d-arginine oligomers. The length of the side chains had a dramatic affect on cellular entry. The amount of cellular uptake was proportional to the length of the side chain with N-hxg>N-btg>N-arg>N-etg. Cellular uptake was improved when the number of alkyl spacer units between the guanidine head group and the backbone was increased. Significantly, N-hxg9 was superior to r9, the latter being 100-fold better than $Tat_{49-57}$. This result led us to prepare peptoid derivatives containing longer octyl spacers (N-ocg) between the guanidino groups and the backbone. Issues related to solubility prevented us from testing these compounds.

Because both perguanidinylated peptides and perguanidinylated peptoids efficiently enter cells, the guanidine head group (independent of backbone) is apparently the critical structural determinant of cellular uptake. However, the presence of several (over six) guanidine moieties on a molecular scaffold is not sufficient for active transport into cells as the N-chg peptoids did not efficiently translocate into cells.

Thus, in addition to the importance of the guanidine head group, there are structure/conformational requirements that are significant for cellular uptake.

In summary, this investigation identified a series of structural characteristics including sequence length, amino acid composition, and chirality that influence the ability of $Tat_{49-57}$ to enter cells. These characteristics provided the blueprint for the design of a series of novel peptoids, of which 17 members were synthesized and assayed for cellular uptake. Significantly, the N-hxg9 transporter was found to be superior in cell uptake to r9 which was comparable to N-btg9. Hence, these peptoid transporters proved to be substantially better than $Tat_{49-57}$. This research established that the peptide backbone and hydrogen bonding along that backbone are not required for cellular uptake, that the guanidino head group is superior to other cationic subunits, and most significantly, that an extension of the alkyl chain between the backbone and the head group provides superior transporters. In addition to better uptake performance, these novel peptoids offer several advantages over $Tat_{49-57}$ including cost-effectiveness, ease of synthesis of analogs, and protease stability. These features along with their significant water solubility (>100 mg/mL) indicate that these novel peptoids could serve as effective transporters for the molecular delivery of drugs, drug candidates, and other agents into cells.

Example 16

Synthesis of Itraconazole-Transporter Conjugate

Figure 30:
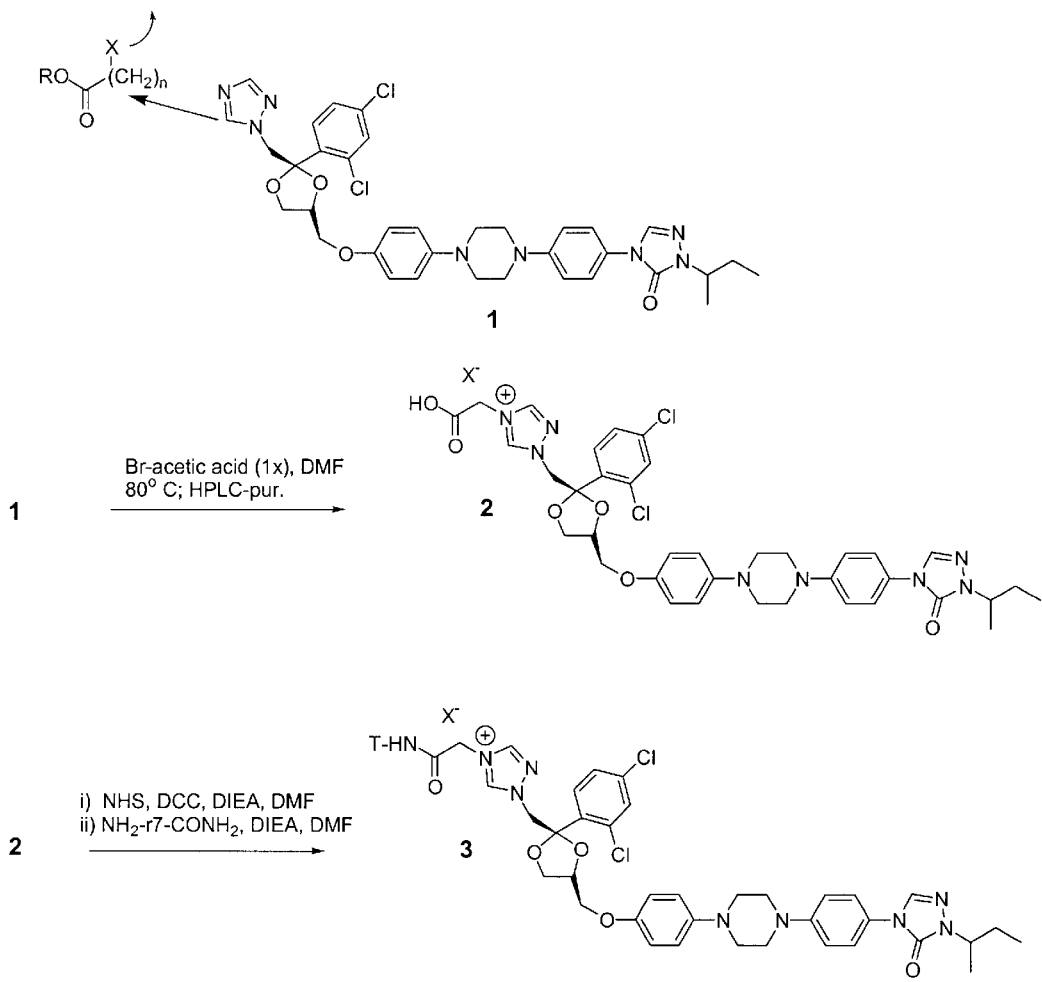
FIG. 30 shows a general strategy for attaching a delivery-enhancing transporter to a drug that includes a triazole ring structure.

This Example provides one application of a general strategy for attaching a delivery-enhancing transporter to a compound that includes a triazole structure. The scheme, using attachment of itraconazole to an arginine (r7) delivery-enhancing transporter as an example, is shown in FIG. 30. In the scheme, R is H or alkyl, n is 1 or 2, and X is a halogen.

The reaction involves making use of quaternization of a nitrogen in the triazole ring to attach an acyl group that has a halogen (e.g., Br, Fl, I) or a methyl ester. Compound 3 was isolated by HPLC. Proton NMR in $D_2O$ revealed itraconazole and transporter peaks.

The methyl ester provided yields of 70% and greater, while yields obtained using the Br-propionic acid/ester pair were 40–50%. The acyl derivative is then reacted with the amine of the delivery-enhancing transporter to form the conjugate. Alternatively, the halogenated acyl group can first be attached to the transporter molecule through an amide linkage, after which the reaction with the drug compound is conducted.

Example 17

Preparation of FK506 Conjugates

Figure 31A:
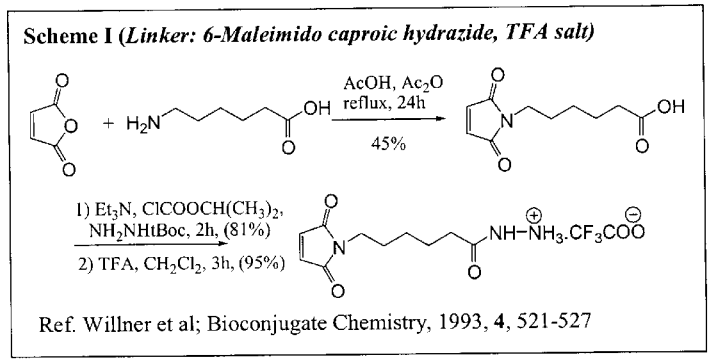
FIG. 31A and FIG. 31B show synthetic schemes for making conjugates in which FK506 is attached to a delivery-enhancing transporter.
Figure 31A:
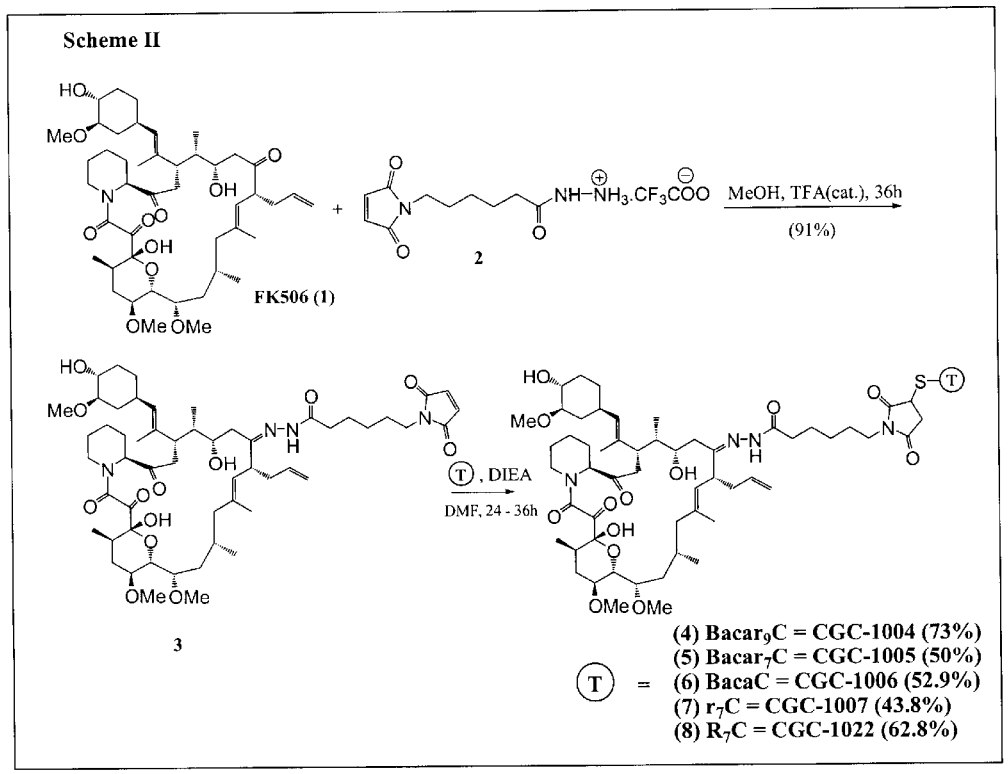
Figure 31B:
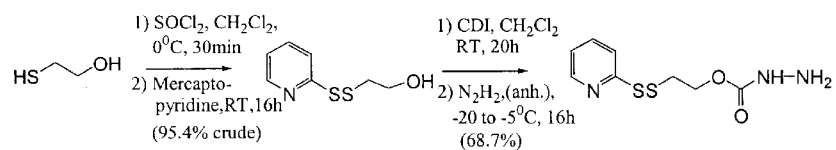
Figure 31B:
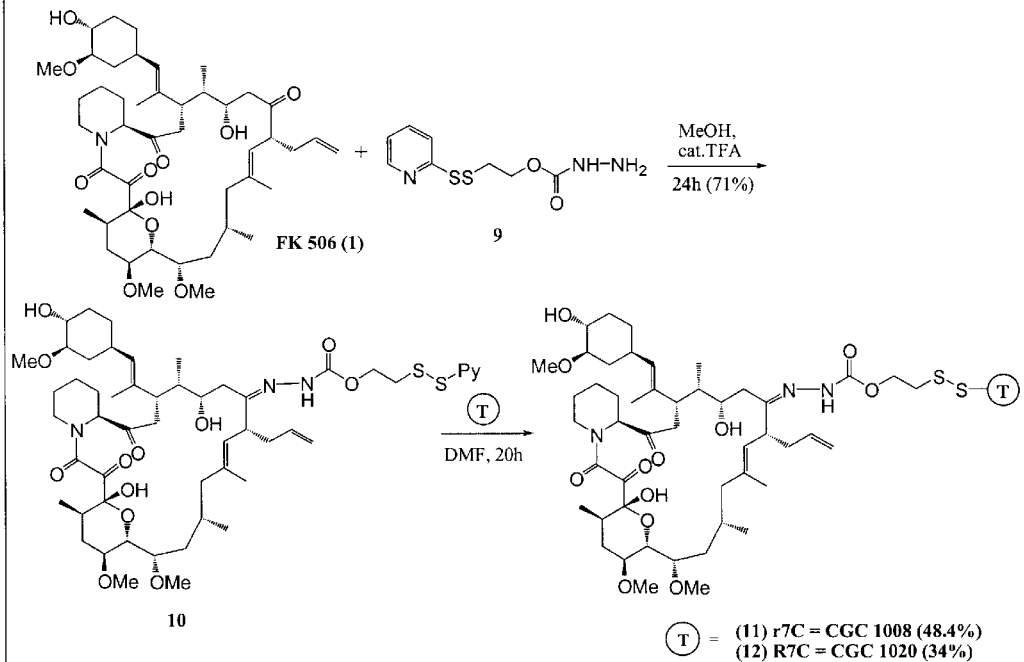

This Example describes the preparation of conjugates in which FK506 is attached to a delivery-enhancing transporter. Two different linkers were used, each of which released FK506 at physiological pH (pH 5.5 to 7.5), but had longer half-lives at more acidic pH. These schemes are diagrammed in FIGS. 31A and B.

Linker 1: 6-maleimidocaproic Hydrazide Trifluroacetate (Scheme I and II)

A solution of FK506 (1) (0.1 g, 124.4 μmol), 6-maleiimidocaproic hydrazide trifluoroacetate (2) (0.126 g, 373.2 μmol) and trifluoroacetic acid (catalytic, 1 μL) in anhydrous methanol (5 mL) was stirred at room temperature for 36 h. The reaction was monitored by thin layer chromatography that showed almost complete disappearance of the starting material. [TLC solvent system—dichloromethane (95): methanol (5), $R_f$=0.3]. The reaction mixture was concentrated to dryness and dissolved in ethyl acetate (20 mL). The organic layer was washed with water and 10% sodium bicarbonate solution and then dried over sodium sulfate, filtered and concentrated. The residue was purified by column chromatography using dichloromethane (96): methanol (4) as eluent to give the hydrazone 3 (0.116 g, 92%).

A solution of the above hydrazone (3) (0.025 g. 24.7 μmol), transporter (1×, $Bacar_9CCONH_2$.9TFA, $Bacar_7CCONH_2$.7TFA, $BacaCCONH_2$, $NH_2r_7CCONH_2$.8TFA, $NH_2R_7CCONH_2$.8TFA (SEQ ID NO:32)) and diisopropylethylamine (1×) in anhydrous dimethylformamide (1 mL) were stirred under nitrogen at room temperature for 36 h when TLC indicated the complete disappearance of the starting hydrazone. Solvent was evaporated from the reaction mixture and the residue purified by reverse phase HPLC using trifluoroacetic acid buffered water and acetonitrile.

Yields of conjugates with various transporters:

Conjugate with $Bacar_9CCONH_2$.9TFA (4)—73%

$Bacar_7CCONH_2$.7TFA (5)—50%

$BacaCCONH_2$ (6)—52.9%

$NH_2r_7CCONH_2$.8TFA (7)—43.8%

$NH_2R_7CCONH_2$.8TFA (SEQ ID NO:32) (8)—62.8%

Structures of all the products were confirmed by 1H-NMR spectra and TOF MS analysis.

Linker 2: 2-(2-pyridinyldithio)ethyl Hydrazine Carboxylate (Scheme III and IV)

A solution of FK506 (1) (0.1 g, 124.4 μmol), 2-(2-pyridinyldithio) ethyl hydrazine carboxylate (9) (0.091 g, 373.2 μmol) and trifluoroacetic acid (catalytic, 1 μL) in anhydrous methanol (5 mL) was stirred at room temperature for 16 h. The reaction was monitored by thin layer chromatography that showed almost complete disappearance of the starting material. [TLC solvent system—ethyl acetate $R_f$=0.5]. The reaction mixture was concentrated to dryness and dissolved in ethyl acetate (20 mL). The organic layer was washed with water and 10% sodium bicarbonate solution and then dried over sodium sulfate, filtered and concentrated. The residue was purified by column chromatography using dichloromethane (97): methanol (3) as eluent to give the hydrazone 10 (0.091 g, 71%)

Example 18

Differential Uptake of Transporters in the Gastrointestinal Tract

Methods

Gastrointestinal Absorption Protocol

Experiments were performed on 8- to 10-week-old female Swiss Webster mice purchased from Taconic (Germantown, N.Y.). Mice were anesthetized with Nembutal and a midline incision was made along the abdomen. Intestines were measured, tied off at both ends of the desired section with sutures, and biotinylated peptides were injected into the lumen (approximately 100λ/inch). After a fifteen minute incubation, the tissue was removed and the lumen was gently washed with PBS.

To determine whether CellGate transporters could enter the squamous epithelia of the oral cavity, mice were anesthetized with Nembutal, their heads tipped to one side and solutions of the biotinylated peptides were placed in their mouths. After fifteen minutes the liquid was removed by pipette.

Preparation of Histological Sections of Regions of the Gastrointestinal Tract

Immediately following incubation with biotinylated peptides, the anesthetized rodents were sacrificed by cervical dislocation and the tied off sections of the GI tract were removed. The lumens of the various sections were filled with OCT using a plastic tipped syringe, immersed in OCT filled boats, and snap frozen in a 2-methyl-butane/dry ice solution. Frozen sections were allowed to warm slightly and 2 mm thick sagital cuts were made using a steel razor blade. The cuts were placed into OCT molds and snap frozen in a 2-methyl-butane/dry ice solution. Sections (5 μm) were cut on the cryostat, fixed in acetone at 4° C. for 10 minute, and allowed to air dry. After rehydration in PBS for 5 minutes, sections were blocked with normal horse serum, washed, incubated with streptavidin-FITC (20 μg/ml) for 30 minutes, washed, and mounted with mounting medium containing propidium iodide (PI).

Tissue Culture

Caco-2 cells were acquired from ATCC, thawed, and grown in DMEM containing penicillin, streptomycin, glutamine, and 10% fetal bovine serum for 3–5 days to confluency (>250,000 cells/cm$^2$) and then passaged at 60,000 cells/cm$^2$ for several passage cycles. Passage numbers 25–29 were plated on Snapwell 12 mm diameter 0.4-micron pore size polycarbonate membranes (Corning Costar, Corning, N.Y.) at 60,000 cells per membrane and allowed to grow for at least 21 days, with media changed every other day.

Cellular Uptake in Caco-2 Cells

To analyze the penetration of fluorescent oligomers of D-arginine into the cells when in suspension, the monolayers were treated with trypsin (4.5 ml of a 0.05% solution Gibco, Grand Rapids, Mich.) and the individual cell suspension was spun down. Cells were resuspended, counted and treated with varying concentrations of Fl aca r5, Fl aca r7, Fl aca r9 and Fl aca k9 (from 50-0.8 μM) for five minutes, washed, resuspended in 400λ PBS, 2%FBS, 40ngPI/ml and analyzed by flow cytometry.

To analyze the ability of the fluorescent peptides to enter Caco-2 cells when part of a monolayer, the cells were seeded in lab-tek flaskette microscope slides (Nalge Nunc Int., Naperville, Ill.) in 4 ml at a density of 60,000 cells/ml and grown for 21 days with the media being changed every other day. Once the monolayer was established, it was incubated with 100 μM Fl aca r9 CONH2 for a five minutes. The monolayer was subsequently washed with PBS/2% FBS twice to remove labeled peptide and analyzed using fluorescent microscopy.

Transport Across Monolayers of Caco-2 Cells

The experiments analyzing whether short oligomers of D-arginine could cross monolayers of Caco-2 cells were performed using a voltage clamp amplifier and Easymount side-by-side horizontal diffusion chamber (Physiologic Instruments, San Diego, Calif.) with a 95% oxygen 5% carbon dioxide gas lift system connected to a recirculating water bath.

Current measurements ($I_2$-$I_1$) were taken at five minute intervals, including 10 minutes prior to the addition of the test compounds to insure monolayers were intact. At zero time test compounds were added at the proper concentrations and measurements recorded. Measurements were taken for 60 minutes at 5 minute intervals; transepithelia electrical resistance (TEER) and short circuit current (Isc) were subsequently calculated from these values.

Synthetic Chemistry
Cyclosporin A

The details of the CsA conjugate used in this study have been described previously (Rothbard et al. *Nature Medicine* 6, 1253 2000). See also, FIG. 6. Briefly, CsA was conjugated to a heptamer of D-arginine through a pH sensitive linker as shown in FIG. 6A. The resultant conjugate is stable at acidic pH but at pH>7 it undergoes an intramolecular cyclization involving addition of the free amine to the carbonyl adjacent to CsA (FIG. 6B), which results in the release of unmodified CsA.

Taxol

Taxol was treated with α-chloro acetic anhydride delivering the C-2' chloro acetyl derivative 12 in essentially quantitative yield.

carbonyl. The protonation state of this nitrogen is crucial for this mechanism, since only the free amine will be capable of this release. Additionally, both conjugates share a common α-hetero atom substituted acetate moiety making them susceptible to simple ester hydrolysis. This offers an additional release pathway.

Intracolonic Injections

Wistar rats, females of approximately 200–300 g (Simonsen, Gilroy, Calif.), were anesthetized, their abdomens were shaved, midline incisions were made, and a one-half inch section of the ascending colon in each animal was tied off with sutures. Taxol and cyclosporin (5 mg/kg) were injected as solutions in a 1:1 v/v Cremophor EL:ethanol mixture, whereas equivalent molar amounts of the r7 conjugates were injected in PBS. In all cases, the volume

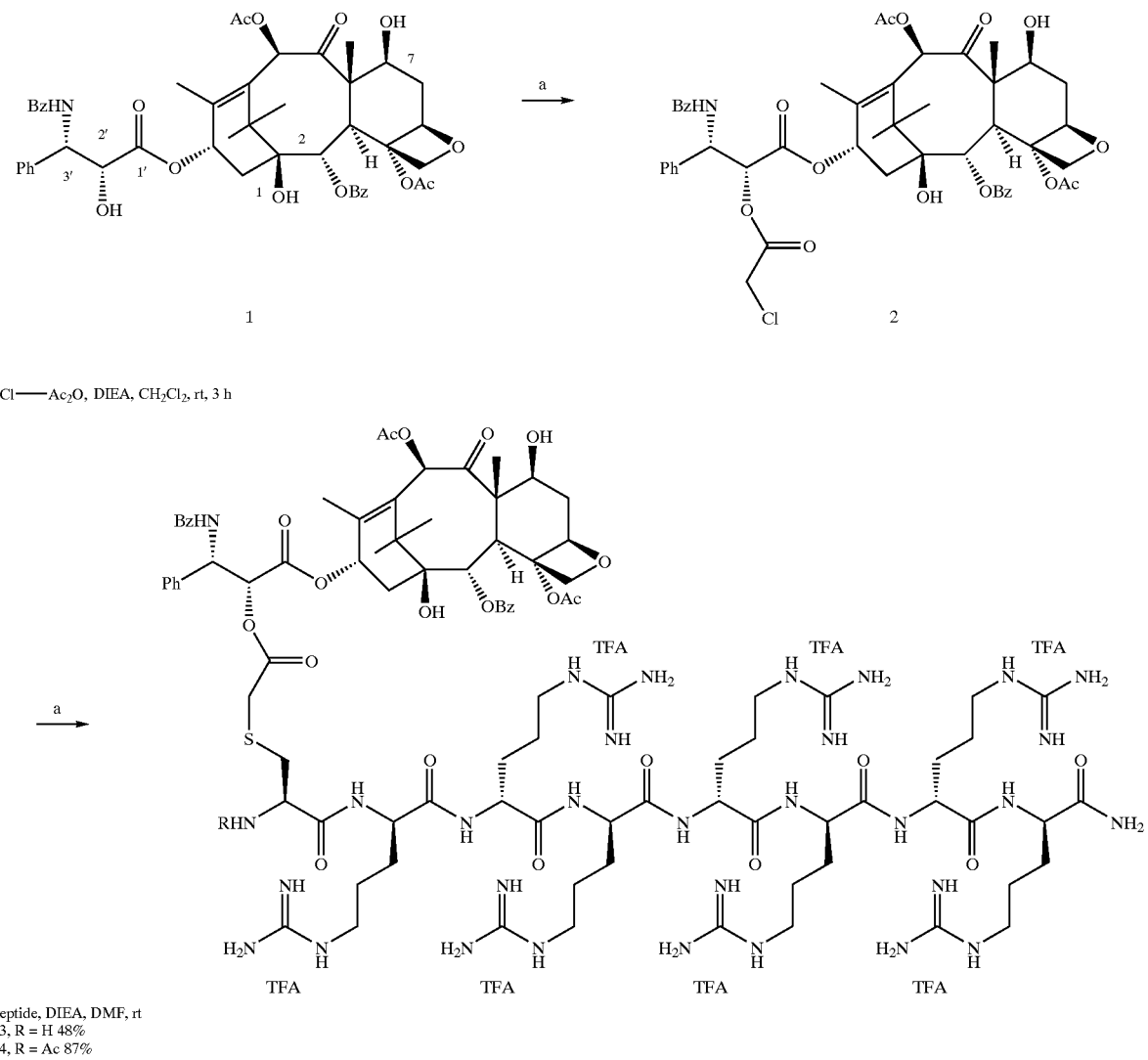

a) Cl—Ac$_2$O, DIEA, CH$_2$Cl$_2$, rt, 3 h a) peptide, DIEA, DMF, rt
13, R = H 48%
14, R = Ac 87%

The halogen was displaced by the thiol of the N-terminal (L) cysteine containing heptamer of D-arginine. Conjugations were performed at room temperature in DMF in the presence of DIEA. The final products were isolated by RP-HPLC and lyophilized to yield TFA salts, which were very hygroscopic and readily dissolve in water.

Compound 13 was designed to release taxol via a nucleophilic attack of the N-terminal nitrogen onto the C2' ester injected was approximately 500λ. The colon was placed back into the cavity, and the incision was closed using sutures.

Blood samples were taken from the tail vein at time zero (prior to drug injection), and every thirty minutes for the duration of the experiment, which was empirically determined, with the exception of one animal that expired after ninety minutes. Clotting was inhibited by transferring the blood to glass tubes containing 100λ of 0.5% EDTA, and the blood was frozen.

Drug Extraction from Whole Blood and HPLC MS MS Analysis

Either taxol or cyclosporin was extracted from the whole blood using a modification of literature procedures. Briefly, whole blood (100λ) was transferred to a screw capped glass tube containing five mls of diethyl ether. The sample was vortexed vigorously for two minutes, centrifuged, and frozen in dry ice/methanol. The ethereal layer was transferred to another glass tube and the ether was evaporated. In the case of cyclosporin, the residue was resuspended in 1.5 mls of methanol, water, acetonitrile (3:2:1), while for taxol the residue was resuspended in 1.5 mls methanol:acetonitrile (1:1). Samples were placed into a Perkin-Elmer series 200 autosampler and sequencially injected onto a $C_{18}$ reverse column at 70° C. connected to a Shimadzu HPLC system, eluted with 70% methanol, 30% aqueous ammonium formate buffer, and the effluent was analyzed on a PE Sciex API 3000 tandem mass spectrometer. Known amounts of either cyclosporin A (10–1000 ng/ml) or taxol (1–1000 ng/ml) were added to whole blood and extracted as previously described to generate standard curves. Cyclosporin A was monitored by the two transitions from both 1220 to 1203 daltons and 1220 to 100 daltons. The 1220 species corresponds to the cyclosporin A+ammonia, the 1203 is protonated cyclosporin, while 100 is a known fragment. Taxol was monitored by the two transitions from both 872 to 855 daltons and 872 to 110 daltons. The 872 species corresponds to the ammonium adduct of taxol, the 855 is the protonated parent compound, whereas 110 is the predominant fragment seen in the second quadrupole.

The total amount of cyclosporin A and taxol in the samples was determined by comparing the integrated area of the appropriate peak with values established by the standard curves.

Results

Differential Uptake of Transporters in the Gastrointestinal Tract

Short oligomers of D-arginine have been shown to cross rapidly and efficiently the plasma membrane of a large variety of cell lines grown in suspension. In addition, they have been shown to penetrate multiple layers of the skin when applied topically, multiple layers of endothelial and smooth muscle cells of veins and arteries when injected intravenously, and multiple cell layers of lung tissue when inhaled. To determine whether these compounds could enter the nonkeratinized epithelia of the gastrointestinal tract, sections of the small and large intestines of fasted mice were tied off and solutions of biotinylated nonamers of D-arginine, bio aca r9 $CONH_2$, (100 μM) were injected. After fifteen minutes of exposure, the relevant section of tissue was dissected, frozen, sectioned, and stained with Streptavidin fluorescein to define the location of the biotinylated peptide, and propidium iodide to counterstain all the nuclei in the section.

When injected into the lumen of murine duodenum no detectable staining over background was observed. Poor staining also was seen when the biotinylated peptide was injected into the jejunum. If multiple sections were scanned detectable staining was seen on the tips of some villi. The first sign of uniform staining was observed when sections of the ileum were analyzed. The staining was localized to the tips of the microvilli and did not extend into the crypt cells. Although seen throughout all sections of the ileum, the observed fluorescence did not approach the level of intensity previously observed in the skin, lungs, or the endothelial cells of arteries or veins.

The relatively poor staining of the small intestine markedly differed from that seen when regions of the colon were examined. In both the ascending and transverse sections of the large intestine, biotinylated nonamers of arginine stained all surface areas of the villi, and penetrated several cell layers, reminiscent of the intense staining of the epidermis and dermis when applied topically. In addition, the crypt cells were heavily stained in the colonic sections and evidence for penetration of the full thickness of the section was observed in several areas.

The histological analysis demonstrated that the uptake of bio r9 into the nonkeratinized epithelia layers of the GI tract varied significantly, with uptake increasing with distance from the gastric pylorus. The staining observed in the ileum was greater than that seen in the jejunum, which was greater than the duodenum. The greatest staining was seen in the ascending and transverse regions of the colon. Without intending to limit the invention to a particular theory or mechanism, one theory is that the composition and amount of mucus lining the epithelia might be an important factor in the differential staining.

Cellular Uptake into Caco-2 Cells

Figure 32:
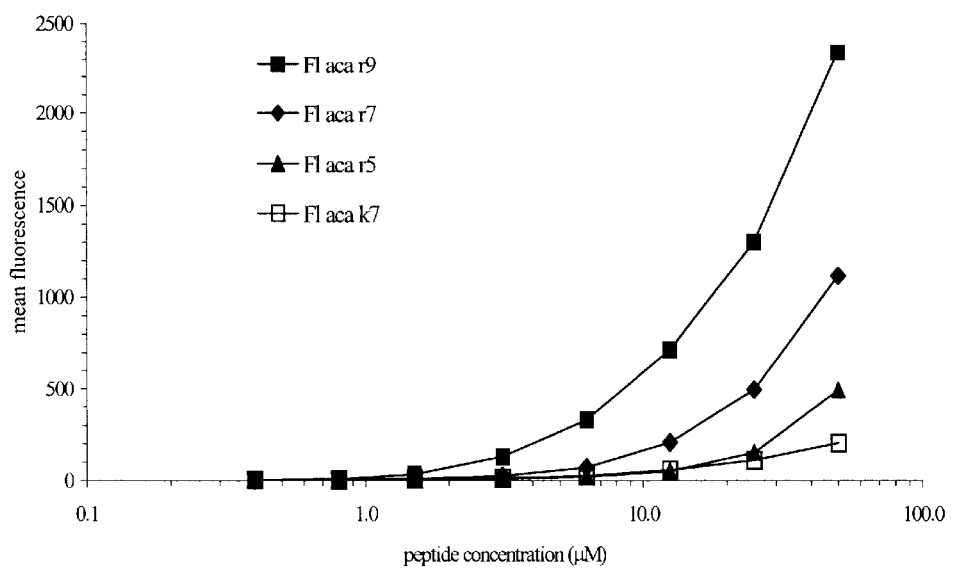
FIG. 32 show that short oligomers of arginine, but not lysine, effectively enter Caco-2 cells. Caco-2 cells were incubated with varying concentrations with each of the peptides shown, washed, and analyzed by flow cytometry. Uptake could be inhibited with preincubation with sodium azide, demonstrating that it was energy dependent.

When Caco-2 cells, commercially-available human colon cells, were incubated in suspension with varying amounts of fluorescently labeled pentamers, heptamers, and nonamers of D-arginine (Fl aca r5, Fl aca r7, Fl aca r9) or nonamers of lysine (Fl aca k7), and analyzed by flow cytometry, a pattern similar to that previously seen in a variety of other suspension cells (Mitchell et al. *Peptide Research* 56, 318 (2000)) was observed (FIG. 32). Uptake of the fluorescent peptides increased with arginine content with r9 being more effective than r7, which was more effective than r5. All the polymers of arginine entered cells more effectively than the nonamers of lysine. Both the rate, the relative amount of fluorescence, and the lack of apparent efflux of the internalized fluorescent peptides over an extended period of time (several hours) were reminiscent of earlier experiments with lymphocytes.

To confirm that the rapid penetration of the short oligomers of arginine into Caco-2 cells was not an artifact seen only when the cells were in suspension, Fl aca r9 $CONH_2$ (50 μM) was incubated for five minutes with Caco-2 cells grown as a monolayer on a microscope slide, washed, and analyzed by fluorescent microscopy. Consistent with the flow cytometry analysis of the suspension cells, virtually every cell in the monolayer was fluorescent after five minutes.

Figure 33:
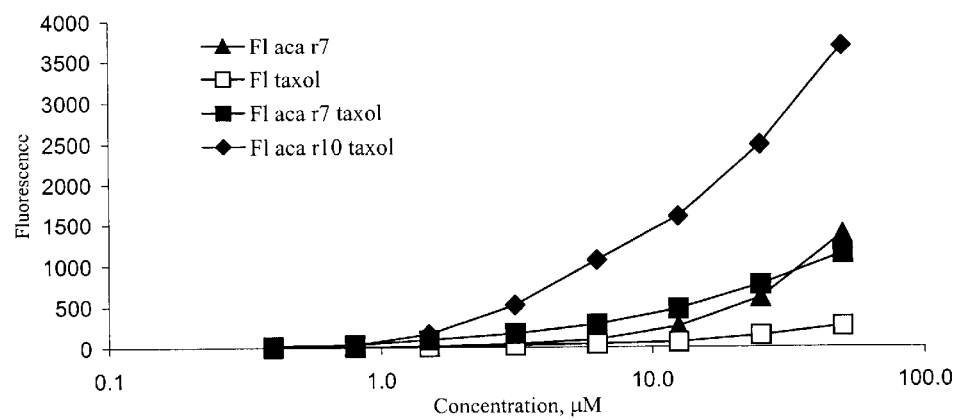
FIG. 33 displays the measured fluorescence of Caco-2 cells exposed to fluorescent taxol or fluorescent, nonreleasable taxol conjugates with either heptamers (r7) or decamers (r10) of D-arginine.

The ability of the peptides to rapidly enter Caco-2 cells was firmly established by placing a monolayer of Caco-2 cells as a membrane in a diffusion chamber and exposing it to fluorescent transporter drug conjugates between taxol and oligomers of arginine of different length. Varying concentrations of the taxol conjugates (50-0.08 μM) were added to the apical side and exposed to the monolayer of Caco-2 cells for three minutes. The membrane was removed from the apparatus, the cells trypsinized, and the resulting cell suspension was analyzed by flow cytometry (FIG. 33). As with the peptides alone, the drug conjugates quickly and efficiently entered the cells composing the monolayer with those containing more arginine subunits being more effective.

Without intending to limit the theory of the invention, these experiments provide strong support for the hypothesis that short oligomers of arginine, either conjugated to fluorescein or therapeutic drugs, such as taxol, rapidly enter Caco-2 cells both in suspension and when grown in monolayers.

Transport Across Caco-2 Monolayers

Figure 34:
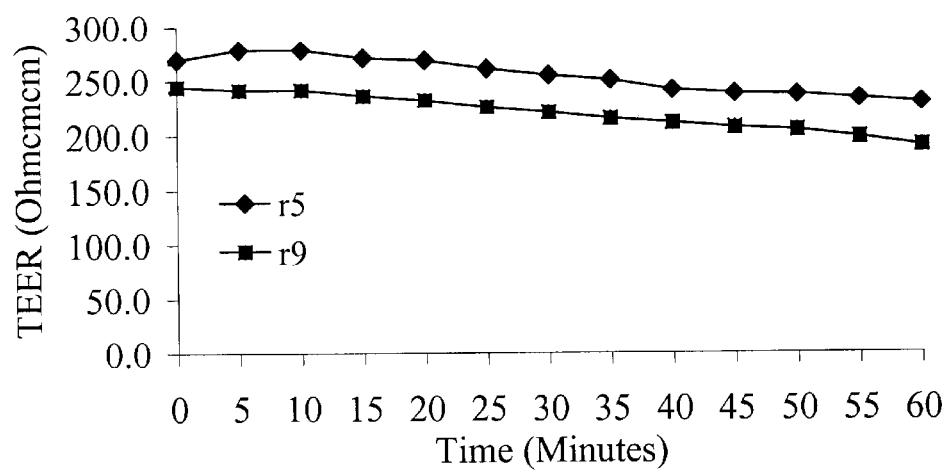
FIG. 34 demonstrates Caco-2 monolayer integrity by the measurement of a stable transepithlial electric resistance of greater than 100 ohm $cm^2$ for the duration of the experiments described in this report.

Crossing the luminal membrane of the gut epithelia is necessary to increase blood levels of a delivered (e.g., buccal administered) drug. To determine whether the transporters could cross the gut epithelia, monolayers of Caco-2 cells were grown in culture and placed as a membrane in a commercially available diffusion chamber. The integrity of the membranes was established by demonstrating that the transepithelial electronic resistance (TEER) was always greater than 100 ohm $cm^2$ (FIG. 34). Such a pattern of stable resistance only is observed when the membrane is intact with no significant spaces between the cells.

Figure 35:
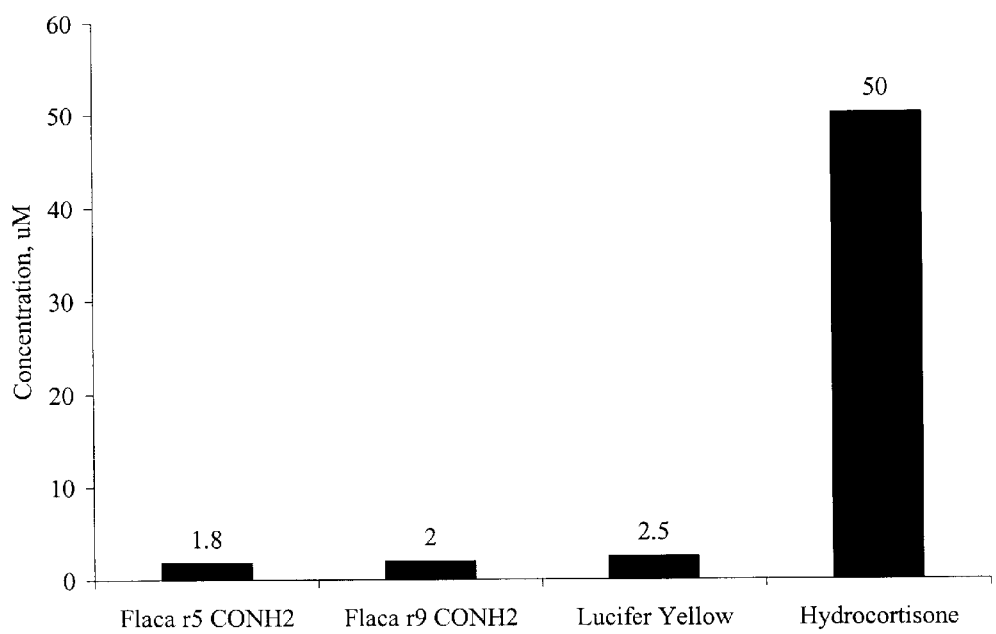
FIG. 35 shows the accumulation of either Fl aca r5, Fl aca r9, Lucifer Yellow, or hydrocortisone in the basolateral chamber of a diffusion apparatus after transport through a Caco-2 cell monolayer after one hour.

Additional evidence that the membrane was both viable and contiguous was that Lucifer Yellow (200 $\mu$M) was not transported across the monolayer, whereas hydrocortisone was transported at amounts consistent with published reports (FIG. 35).

When a variety of fluorescent oligomers of D- or L-arginine, ranging from four to 15 subunits, were placed in the apical chamber in multiple experiments with a large number of membranes, none were significantly transported into the basolateral chamber (FIG. 35).

Taken together, the data presented herein are consistent with the model that short oligomers of arginine either conjugated to delivered compounds such as fluorescein or taxol rapidly enter but are not transported across Caco-2 cell monolayers. This model also implies that the transporters of the invention do not enter Caco-2 cells by endosomes, which are transported across colonic epithelium and excreted on the basolateral side by a well understood pathway. CellGate transporters appear to enter the cytosol directly and do not have a high rate of efflux on the basolateral side.

Measurement of Drug Blood Levels after Intracolonic Injections

Although short oligomers of arginine labeled with fluorescein, either alone, or when conjugated to either taxol or cyclosporin, were unable to cross a monolayer of Caco-2 cells in vitro, the cell line may not precisely mimic the in vivo behavior of the colon. Furthermore, the pattern of fluorescence seen in colon tissue after incubation with short oligomers of arginine demonstrated that the peptides penetrated into layers known to be vascularized.

To determine whether the transporters of the invention could enhance the delivery of orally administered drugs, releasable conjugates of cyclosporin A and taxol were injected intracolonically and the resulting blood levels of the released drugs were measured by LC MS MS.

Figure 36:
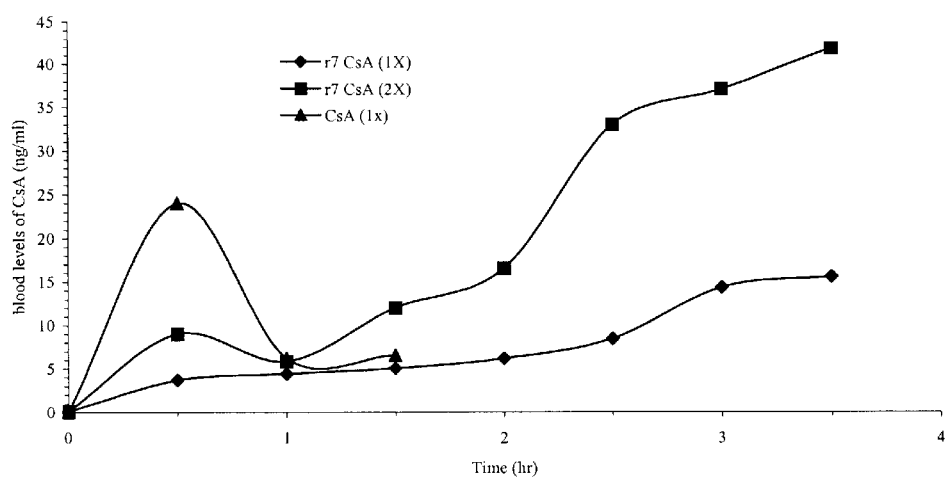
FIG. 36 displays the blood levels of CsA in rats measured by LC MS MS at thirty minute intervals after intracolonic injection. CsA was administered in Cremophor El: ethanol, 1:1, whereas the CsA conjugates were administered in PBS. The half life in PBS, pH 7.4 at 37° C., of the CsA conjugate (CGC1072) was 1.5 hours.

The first experiment was designed to measure blood levels of CsA after intracolonic injection of 5 mg/kg of CsA in Cremophor EL:ethanol compared with an equimolar amount of a releasable r7 conjugate of CsA dissolved in phosphate buffered saline. In the case of the parent drug, blood levels rose to approximately 25 ng/ml of CsA after thirty minutes, and then rapidly fell off to levels close to baseline levels (FIG. 36). No further data was obtained because after 90 minutes the animal died. In contrast, when an equimolar amount of CsA-r7 conjugate was injected, detectable levels of CsA in the blood were observed only after 3 hours (FIG. 36). To determine whether the altered pharmacokinetics of CsA when conjugated to a short oligomer of arginine was reproducible, a third rat was injected with 10 mg/kg equivalent of the water soluble, releasable conjugate. The rate of uptake of CsA in the blood of this animal resembled the animal injected with 5 mg/kg of the conjugate. With more conjugate administered a small increase was seen at 30 minutes, but larger amounts appeared in the blood only after two hours, with blood levels approaching 45 ng/ml after three hours. The overall pattern was similar in the two animals injected with the conjugate. In both cases the overall amount of CsA measured in the circulation was significantly greater than observed when CsA was injected.

The half-life of the CsA conjugate was approximately ninety minutes, which was consistent with the delay in the appearance of CsA in the blood relative to the parent compound. This fact combined with the histological data demonstrating rapid and efficient uptake in the columnar epithelium of the colon and the failure of nonreleasable conjugates of CsA or taxol to cross monolayers of colonic cells in vitro, leads to a sensible and simple model describing the phenomena. Without intending to limit the invention to a particular mechanism or theory, it appears that the conjugates enter the columnar epithelia of the colon with greater efficiency and more rapidly than CsA injected in Cremophor, but were retained in the epithelial cells and did not cross the endothelial cells surrounding the capillaries until the conjugate hydrolyzed. Once released, the CsA freely diffused, or was actively transported, into the blood.

To test this hypothesis, taxol and two different r7-taxol conjugates were injected into the colon and blood levels of the drug were measured at thirty minute intervals. The two r7-taxol conjugates had significantly different half-lives (10 minutes and 5 hours) and were used to test the hypothesis that the hydrolysis of the drug conjugate was the rate limiting step in appearance of the drug in the circulation. If true, the premise predicted that the r7-taxol conjugate with the ten minute half life would release taxol in the epithelia so that it could be detected in the circulation at the thirty minute time point. In contrast, taxol should not be released from the more stable r7 conjugate ($t_{1/2}$=5 hours) and should not be detected in the blood samples taken during the experiment.

Figure 37:
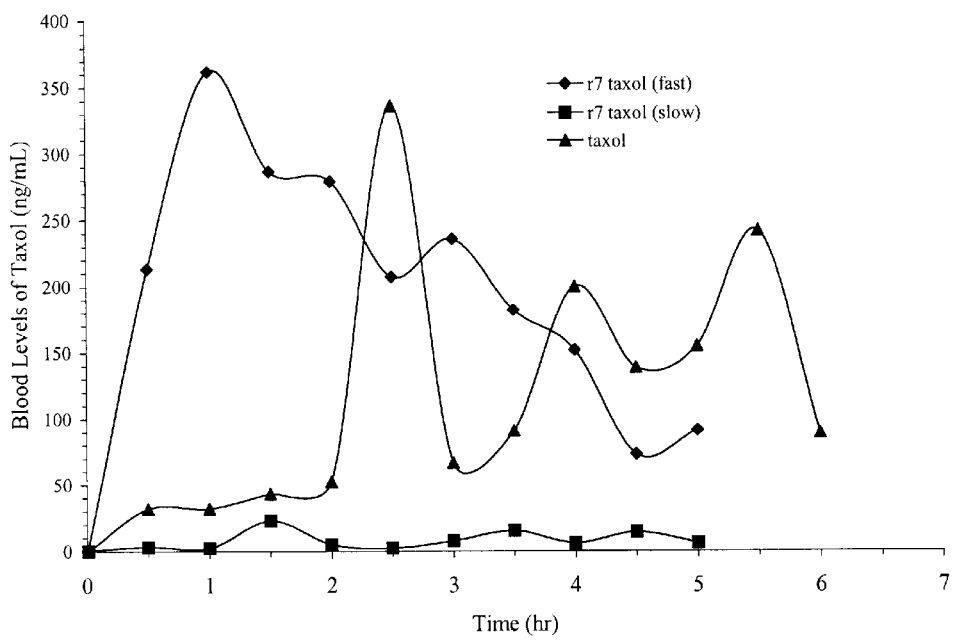
FIG. 37 displays the blood levels of taxol in rats measured by LC MS MS at thirty minute intervals after intracolonic injection. Taxol was administered in Cremophor EL:ethanol, 1:1, whereas the two taxol conjugates were administered in PBS. The half life in PBS, pH 7.4 at 37° C., of the slower releasing conjugate (14) was 5 hours, while that of the faster conjugate (13) was ten minutes. See, Example 18.

This premise was supported by the appearance of taxol in the blood (FIG. 37). Detectable levels of taxol did not appear in the blood when injected in the colon until 2.5 hours with subsequent waves at 4 and 5.5 hours. The oscillating levels of taxol in the blood as a function of time were consistent with published studies with the pattern being rationalized to the ability of Cremophor to sequester some of the material and act as a timed release vehicle. In contrast, when a labile, water soluble r7 conjugate of taxol (13) was administered, greater than 200 ng/ml of taxol was observed at the earliest time point (30 minutes) which continued to increase up to 1 hour, at which point the levels slowly diminished out to five hours. As predicted, injection of the more stable, water soluble r7 conjugate of taxol (14) did not result in significant blood levels of taxol within five hours. These data support the hypothesis that transporters of the invention enter, but do not transverse the colonic epithelium. They can improve oral bioavailability of drugs both by dramatically improving water solubility and by increasing the rate of uptake of the conjugate in the colon. Ultimate delivery of the drug into the blood stream appears to depend on the drug's inherent ability to diffuse through biological membranes and the rate of release from the conjugate.

Discussion

A significant discovery in the experiments described herein is the failure of the peptides to enter the epithelia of the duodenum. This represents the first example of the transporters not entering a cell type or tissue. The pattern of increasing uptake the further the tissue extended from the gastric pylorus was intriguing, most likely due to a gradient of an inhibitor, such as a negatively charged mucus. The failure to stain the upper regions of the small intestine was in stark contrast with the intense staining in the colon, leading to the speculation that transporters of the present invention could be used for selective delivery of therapeutics to the colon. Not only were all luminal surfaces of the colon highly fluorescent, but the staining pattern also revealed that the biotinylated compounds were able to penetrate multiple cell layers and reach vascularized regions of the tissue, suggesting that the transporters should enhance transport into the bloodstream.

However, separate studies using monolayers of the colonic cell line, Caco-2, suggests an alternative mechanism. In the Caco-2 system the transporters rapidly entered, but did not traverse the monolayer. There are several examples of the transporters exhibiting high rates of transport into, but limited rates of efflux from cells and tissue. This is the case for all suspension cell lines examined to date, the best studied being the human T cell line, Jurkat. Short oligomers of D-arginine rapidly enter these cells and exhibit very low exit rates, losing less than 5% of the fluorescent signal after one hour of incubation at 37° C. An even more relevant example of this phenomenon is the low levels of CsA measured in the blood stream of mice receiving multiple topical treatments of a releasable CsA r7 conjugate. As in the case for the colon, staining patterns in sections of skin treated with a biotinylated analog of the CsA conjugate established that the drug penetrated into highly vascularized regions of the dermis. In addition, staining with monoclonal antibodies established that one of the prominant cell types in the dermis that were highly fluorescent were the endothelial cells of the capillaries. Nevertheless, detectable levels of CsA in the blood of these animals were never observed even after ten days of treatment with a 4% ointment applied twice a day. This observation, although anecdotal, is consistent with results better studied in this report.

The ability of the peptides to enter and subsequently exit multiple layers of cells in the skin, the lungs, and the cardiovascular system is in marked contrast to their inability to exit from lymphocytes or Caco-2 cells. Without intending to limit the present invention to a particular theory or mechanism, one difference is the cells through which the peptides rapidly penetrate are connected by tight junctions and other membrane structures inherent in tissue architecture, whereas the individual cells in suspension and perhaps the side of the membrane of endothelial cells contacting the bloodstream lack these features. If structures such as tight or gap junctions modify the surrounding lipid to permit exit of the transporters, then they should be able to diffuse rapidly throughout a tissue, such as skin or the colon, but not be transported into the bloodstream. Consistent with this hypothesis is the model constructed to explain the variations in the rates of appearance of taxol and CsA in the circulation in this report. In this model, the short oligomers of arginine greatly promoted uptake into columnar epithelium of the colon or the squamous epithelium of the cheek, but did not transport the drug into the bloodstream. The blood levels observed were the result of the diffusion, or active transport, of the drug out of the epithelium into the circulation after hydrolysis of the conjugate.

Example 18

Buccal Delivery of Transporter Conjugates

Buccal delivery of taxol and CsA involved adding a concentrated solution (250λ of 5 mg/kg) to the oral cavity of an anesthetized rat lying on its side. Blood samples were taken from the tail vein at time zero (prior to drug injection), and every thirty minutes for the duration of the experiment, which was empirically determined. Clotting was inhibited by transferring the blood to glass tubes containing 100λ of 0.5% EDTA, and the blood was frozen.

The capacity of the transporters to enter the squamous epithelial layers of the oral cavity was examined. A mouse was anesthetized, its head was tipped so that a solution of biotinylated r9 could be administered. The animal was kept in this position for fifteen minutes, at which time it was sacrificed, and the tongue and cheek were dissected, frozen, sectioned, stained with streptavidin-fluorescein, and counterstained with propidium iodide. In both the cheek and the tongue the biotinylated peptides quickly and efficiently penetrated multiple layers of the epithelia and penetrated deep into the interior layers of the tissue, reminiscent of the staining of both the epidermis and dermis of the skin.

Figure 38:
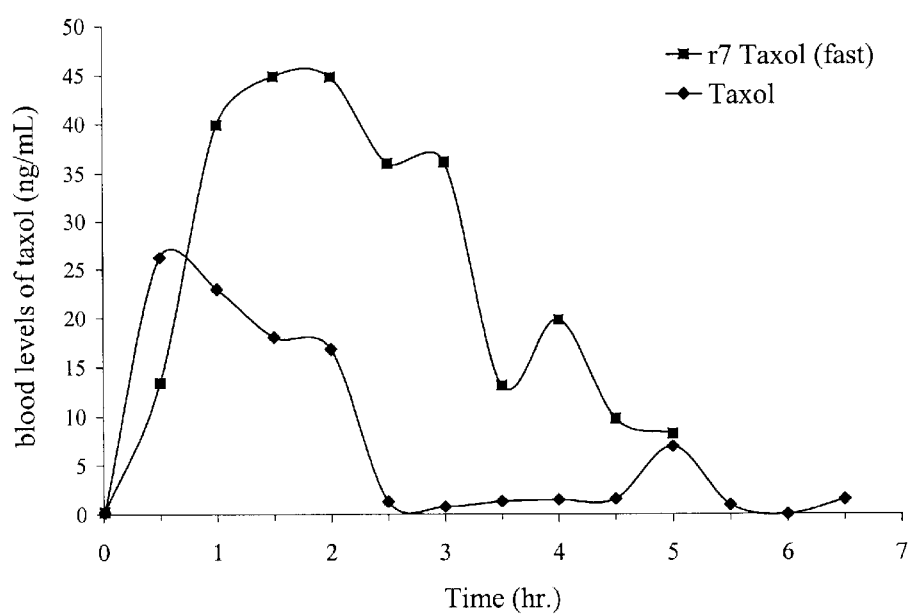
FIG. 38 displays the blood levels of taxol in rats measured by LC MS MS at thirty minute intervals after buccal delivery. Taxol was administered in Cremophor El: ethanol, 1:1, whereas the taxol conjugate was administered in PBS. The half life in PBS, pH 7.4 at 37° C., of the conjugate (13) was ten minutes.

In a second experiment, rats were anesthetized and solutions of both taxol and CsA (5 mg/kg) in Cremophor EL:ethanol 1:1 or equimolar amounts of the corresponding r7 conjugates of these drugs in PBS were simply incubated in the cheek pouch of the animal for the duration of the experiment. LC MS was used to determine the blood levels of only taxol and the fast releasing r7 conjugate. Both the amount and the kinetics of appearance of taxol in the blood when administered in the oral cavity (FIG. 38) differed from when it was injected into the colon. Buccal administration of taxol conjugates appeared to be less effective, with less than one eighth of the amount of taxol being observed in the circulation compared with intracolonic injection. Another difference was the rate of appearance of the unmodified drug. When administered in the oral cavity, taxol appeared in the blood stream by the first time point, whereas in the colonic injection detectable amounts of taxol did not appear for several hours. Even though there was no difference between taxol and the r7-taxol conjugate in the appearance of taxol in the circulation in buccal administration, approximately twice as much material reached the circulation when the conjugated was used.

Example 19

Ocular Delivery of Transporter Conjugates

The ability of the transporters of the invention to penetrate the tissues of the eye was examined. Biotinylated r8 was both injected into the eyes of rabbits and also applied as eyedrops to the outside of the eye.

Briefly, 5 drops of a 1 mM solution of biotinylated r8 in PBS was applied to both eyes of a rabbit and allowed to incubate 15 minutes. The animal was sacrificed and one eye was dissected intact with adjacent tissue, whereas the other was separated into each of its component parts, frozen and separately sectioned, stained with streptavidin-fluorescein and counterstained with propidium iodide. results demonstarted staining in the cornea and eyelid, but not the lens.

50 microliters of a 10 mM solution of biotinylated r8 in PBS was injected into the vitreus humor of another animal and the animal was sacrificed 30 minutes later and the injected eye was dissected. Again one orbital was frozen intact while the other was dissected and the components separately frozen. Results from the injection experiments demonstrated that all interior surfaces of the orb were stained.

Example 20

This example illustrates the conjugation of cyclosporin to a transport moiety using a pH sensitive linking group (see FIGS. 6A and 9B).

In this example, cyclosporin is converted to its chloroacetate ester using chloroacetic anhydride to provide 6i (see FIG. 6). The ester 6i is then treated with benzylamine to provide 6ii. Reaction of the amine with Boc-protected iminodiacetic acid anhydride provides the acid 6iii which is then converted to an activated ester (6iv) with N-hydroxysuccinimide. Coupling of 6iv with L-Arginine heptamer (SEQ ID NO:3) provides the BOC-protected conjugate 6v, which can be converted to conjugate 6vi by removal of the BOC protecting group according to established methods.

Transport moieties having arginine groups separated by, for example, glycine, ε-aminocaproic acid, or γ-aminobutyric acid can be used in place of the arginine heptamer in this and in the following examples that show oligoarginine transport groups.

Example 21

This example illustrates the conjugation of acyclovir to a transport moiety.

a. Conjugation of Acyclovir to $r_7CONH_2$

This example illustrates the conjugation of acyclovir to $r_7CONH_2$ via the linking group:

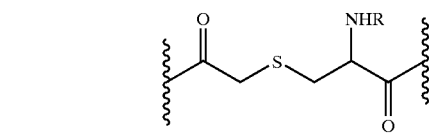

R = H or Ac i) Preparation of acyclovir α-chloroester:

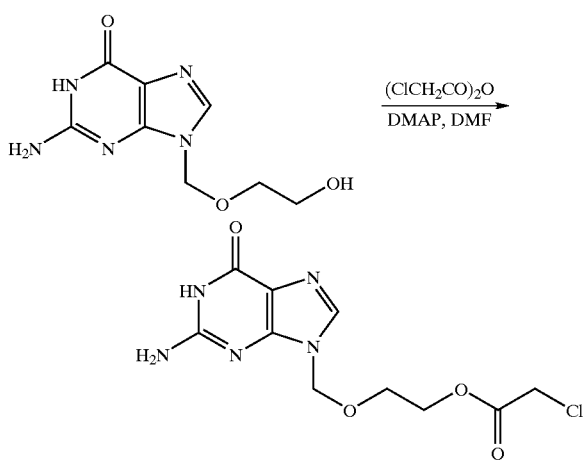

A solution of acyclovir (100 mg, 0.44 mmol), dimethylaminopyridine (5.4 mg, 0.044 mmol) and chloroacetic anhydride (226 mg, 1.32 mmol) in dimethylformamide (9 mL) was stirred at room temperature for 18 h. The dimethylformamide was removed by evaporation. The crude product was purified by reverse-phase HPLC (22 mm×250 mm C-18 column, a 5–25% $CH_3CN/H_2O$ gradient with 0.1% trifluoroacetic acid, 214 and 254 nm UV detection) and lyophilized. The product was obtained as a white powder (62 mg, 47%). $^1H$ NMR (300 MHz, DMSO-$d_6$) δ 10.67 (s, 1H), 7.88 (s, 1H), 6.53 (s, 1H), 5.27 (s, 2H), 4.35 (s, 2H), 4.21 (t, J=3 Hz, 2H), 3.70 (t, J=3 Hz, 2H); $^{13}C$ NMR (75 MHz, DMSO-$d_6$) δ 168.1, 157.6, 154.8, 152.3, 138.6, 117.1, 72.7, 67.1, 65.2, 41.8; TOF-MS (m/z): 302.0 [M+H].

ii) Conjugation of acyclovir α-chloroester to $H_2N$—C-r7-$CONH_2$

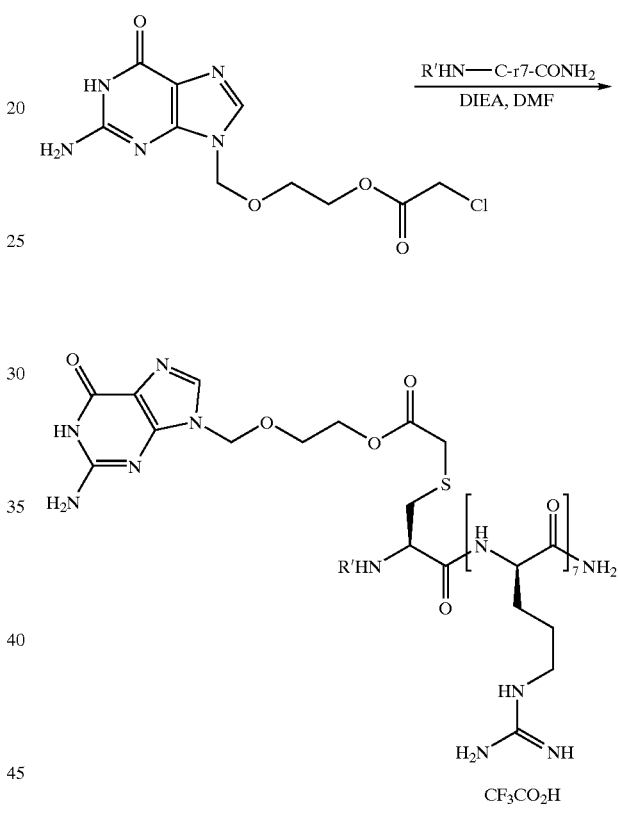

R' = H or Ac

A solution of acyclovir α-chloroester (7 mg, 0.024 mmol), $H_2N$—C-r7-$CONH_2$ (50 mg, 0.024 mmol) and diisopropylethylamine (6.4 μL, 0.036 mmol) in dimethylformamide (1 mL) was stirred for 18 h. The dimethylformamide was removed by evaporation. The crude product was purified by reverse-phase HPLC (22 mm×250 mm C-18 column, a 5–25% $CH_3CN/H_2O$ gradient with 0.1% trifluoroacetic acid, 214 and 254 nm UV detection) and lyophilized. The desired product was obtained as a white powder (24 mg, 69%). TOF-MS (m/z): 494.6 [(M+H)/3], 371.0 [(M+H)/4].

The yield could be increased by using 10 molar equivalents of diisopropylethylamine rather than 1.5 molar equivalents. Product was again obtained as a white powder (79%). TOF-MS (m/z): 508.7 [(M+H)/3], 381.5 [(M+H)/4], 305.5 [(M+H)/5].

b. Conjugation of Acyclovir to a Biotin-Containing Derivative of $r_5$-Cys-CONH$_2$

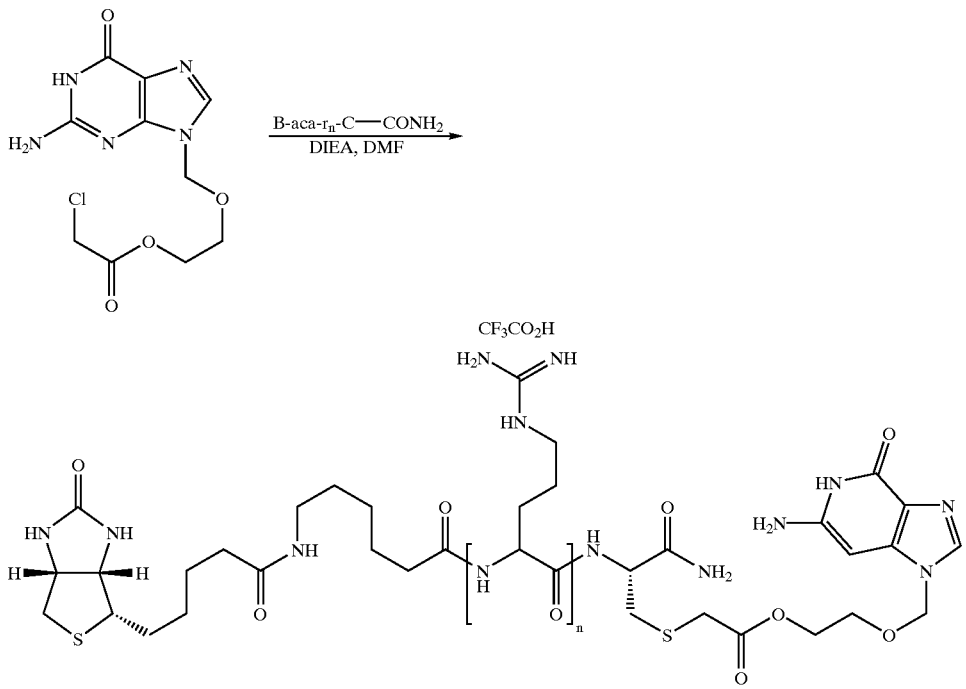

Reactions were carried out as illustrated above, using the synthetic techniques provided in the examples above.

i) Biotin-aminocaproic acid-r5-Cys(acyclovir)-CONH$_2$ was obtained as a white powder (36%). TOF-MS (m/z): 868.2 {(M+2 TFA)/2], 811.2 [(M+1 TFA)/2], 754.1 [(M+1 TFA)/3], 503.0 [(M+H)/3], 377.4 [(M+H)/4]. Similarly, ii) Biotin-aminocaproic acid-r7-C(acyclovir)-CONH$_2$— was obtained as a white powder (33%). TOF-MS (m/z):722.1 [(M+3 TFA)/3], 684.6 [(M+2 TFA)/3], 607.1 [(M+H)/3], 455.5 [(M+H)/4], 364.8 [(M+H)/5], 304.3 [(M+H)/6].

Example 22

This example illustrates the conjugation of hydrocortisone to a transport moiety.

a. Conjugation of Hydrocortisone to r$_7$CONH$_2$ i) Preparation of hydrocortisone a-chloroester

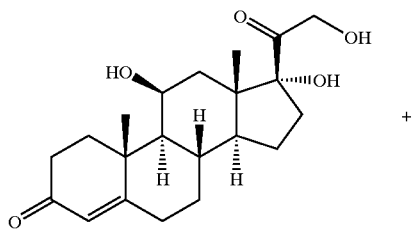

-continued

To a solution of hydrocortisone (500 mg, 1.38 mmol), scandium triflate (408 mg, 0.83 mmol) and chloroacetic anhydride (708 mg, 4.14 mmol) in dry THF was added dimethylaminopyridine (506 mg, 4.14 mmol). The solution turned bright yellow upon addition of dimethylaminopyridine. After 30 min the solvent was evaporated off and the crude material taken up into ethyl acetate (100 mL). The ethyl acetate layer was washed with 1.0 N HCl and brine. The organic phase was collected, dried (Na$_2$SO$_4$) and evaporated to provide the product as a white solid (533 mg, 88%). $^1$H NMR (300 MHz, DMSO-d$_6$) δ 5.56 (s, 1H), 5.46 (s, 1H), 5.20 (d, J=18 Hz, 1H), 4.85 (d, J=18 Hz, 1H), 4.51 (s, 2H), 4.37 (br s, 1H), 4.27 (br s, 1H), 2.54-2.33 (m, 2H), 2.22-2.03 (m, 3H), 1.99-1.61 (m, 8H), 1.52-1.24 (m, 5H), 1.02-0.98 (d, J=12 Hz, 1H), 0.88-0.85 (d, J=9 Hz, 1H), 0.77 (s, 3 H); $^{13}$C NMR (75 MHz, DMSO-d$_6$) δ 205.4, 198.8, 173.0, 167.6, 122.3, 89.5, 69.7, 67.3, 56.4, 52.4, 47.8, 41.6, 39.7, 35.0, 34.3, 34.0, 33.6, 32.3, 32.0, 24.2, 21.3, 17.4; TOF-MS (m/z): 439.1 (M+H).

(Reference for acetylation—Zhao, H.; Pendri, A.; Greenwald, R. B. *J. Org. Chem.* 1998, 63, 7559–7562.)

ii) Coupling to R'NH-Cys-$r_7$-CONH$_2$

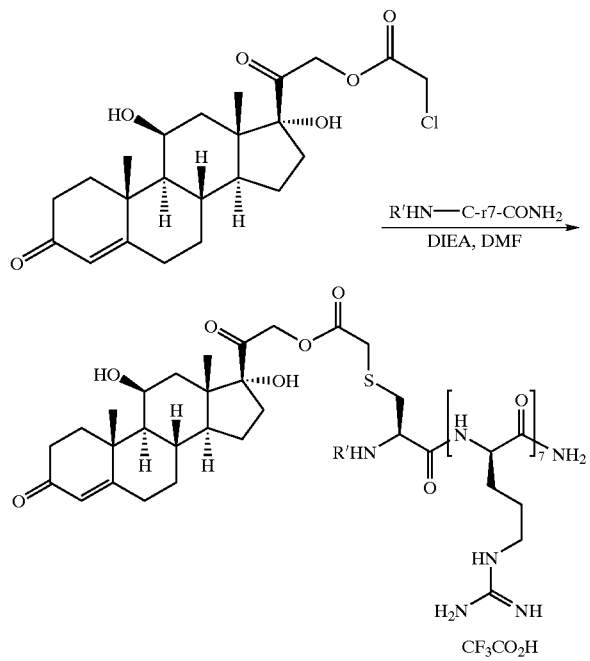

R' = H or Ac

A solution of hydrocortisone α-chloroester (31 mg, 0.071 mmol), H$_2$N—C-r7-CONH$_2$ (150 mg, 0.071 mmol) and diisopropylethylamine (15 μL, 0.085 mmol) in dimethylformamide (1 mL) was stirred for 18 h. The dimethylformamide was evaporated off. The crude product purified by reverse-phase HPLC (22 mm×250 mm C-18 column, a 5–30% CH$_3$CN/H$_2$O gradient with 0.1% trifluoroacetic acid, 214 and 254 nm UV detection) and lyophilized. The desired product was obtained as a white powder (25 mg, 14%). TOF-MS (m/z): 1037.4 [(M+4 TFA)/2], 616.1 [(M+2 TFA)/3], 578.3 [(M+1 TFA)/3], 540.5 [(M+H)/3], 405.7 [(M+H)/4], 324.5 [(M+H)/5].

The use of 10 molar equivalents of diisopropylethylamine rather than 1.2 molar equivalents provided the desired product as a yellow powder (52% yield). TOF-MS (m/z): 887.0 [(M+1TFA)/2], 830.6 [(M+H)/2], 553.7 [(M+H)/3], 415.5 [(M+H)/4].

b. Conjugation of Hydrocortisone to a Biotin-Containing Derivative of $r_5$-Cys-CONH$_2$

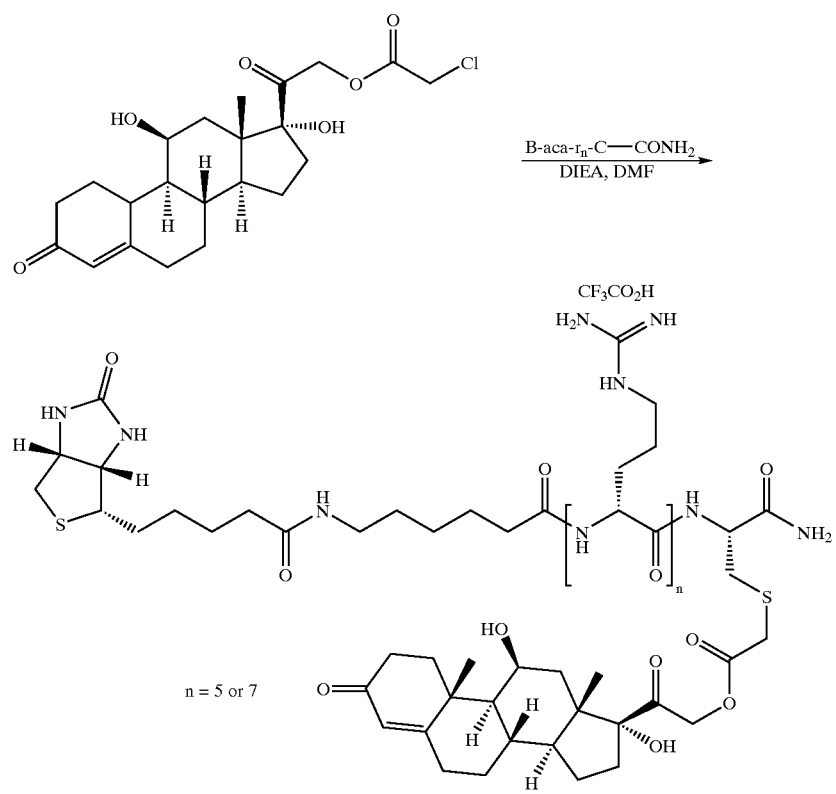

n = 5 or 7

Reactions were carried out as illustrated above, using the synthetic techniques provided in the examples above.

i) Biotin-aminocaproic acid-r5-C(hydrocortisone)-CONH$_2$—Used 10 molar equivalents of diisopropylethylamine rather than 1.2 molar equivalents. Product a white powder (65%). TOF-MS (m/z): 880.7 [(M+1 TFA)/2], 548.7 [(M+H)/3].

ii) Biotin-aminocaproic acid-r7-C(hydrocortisone)-CONH$_2$—Used 10 molar equivalents of diisopropylethylamine rather than 1.2 molar equivalents. Product a white powder (36%). TOF-MS (m/z): 692.3 [(M+1 TFA)/3], 652.8 [(M+H)/3], 520.0 [(M+1 TFA)/4], 490.0 [(M+H)/4], 392.5 [(M+H)/5].

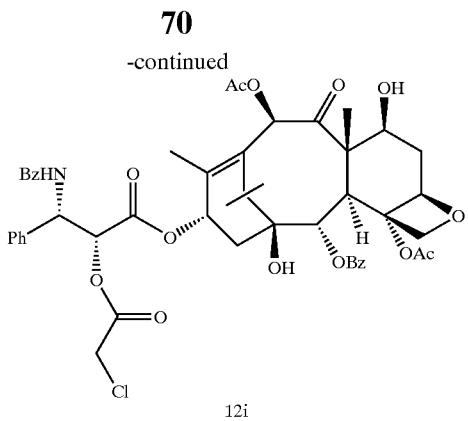

a) Cl—Ac$_2$O, DIEA, CH$_2$Cl$_2$, rt, 3 h

Taxol was treated with α-chloro acetic anhydride providing the C-2' chloro acetyl derivative 12i in essentially quantitative yield.

ii) Formation of taxol derivative

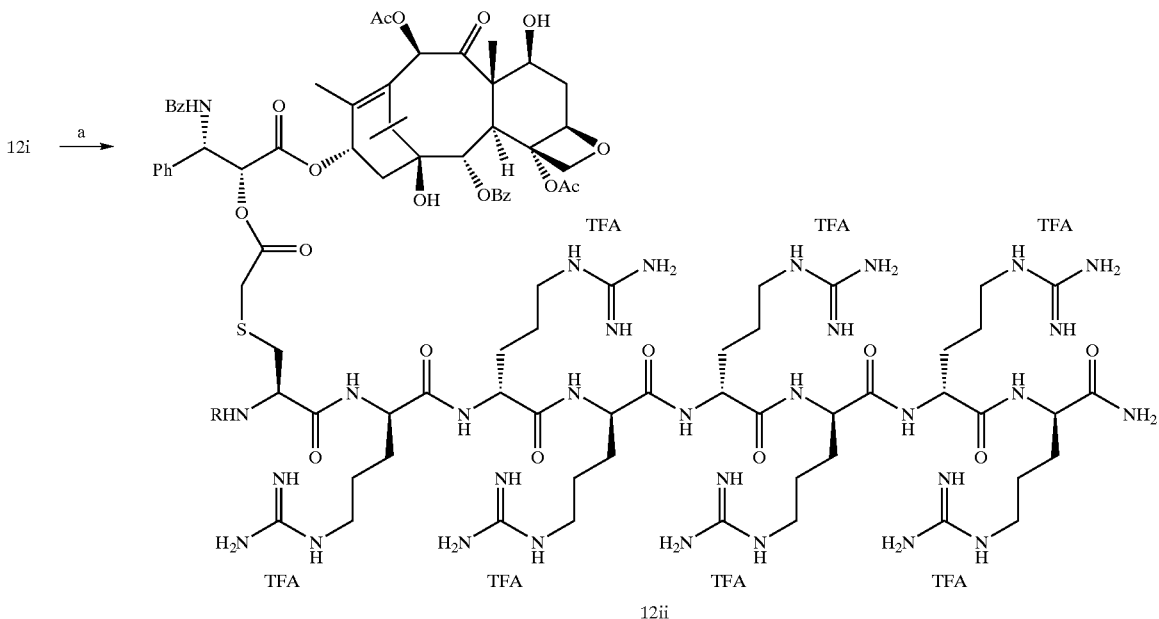

a) peptide, DIEA, DMF, rt
R = H 48%
R = Ac 87%

Example 23

This example illustrates the conjugation of taxol to a transport moiety.

a. Conjugation of Taxol to r$_7$-CONH$_2$

This example illustrates the application of methodology outlined above to the preparation of a taxol conjugate (see FIG. 12).

i) Preparation of taxol a-chloroacetate ester

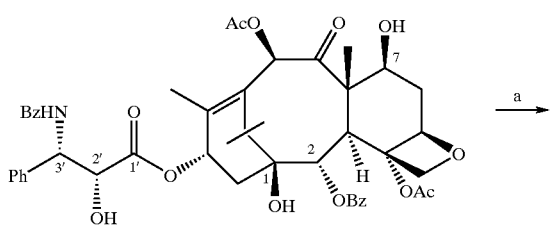

The halogen atom of the chloroacetate ester was displaced by the thiol of an N-terminal (L) cysteine containing heptamer of arginine. To avoid degradation of the transporter entity by proteases in-vivo, D-arginine was used as the building unit. Conjugation reactions were performed at room temperature in DMF in the presence of diisopropylethylamine. The final products were isolated by RP-HPLC and lyophilized to white powders. It is important to note that the native conjugate (R=H) is isolated as its TFA salt at the cysteine primary amine. The conjugates are generally quite hygroscopic and readily dissolve in water.

The conjugate wherein R=H was designed to release the parent drug via a nucleophilic attack of the N-terminal nitrogen onto the C2' ester carbonyl. The protonation state of this nitrogen is crucial for this mechanism, since only the free amine will be capable of this release. Additionally, both conjugates share a common α-hetero atom substituted acetate moiety making them susceptible to simple ester hydrolysis. This offers an additional release pathway.

Example 24

This example illustrates two methods of linking active agents to transport moieties. Illustration is provided for retinoic acid derivatives linked to poly-D-Arg derivatives but can be applied to linkages between other biological agents and the transport moieties of the present invention.

a. Linkage Between a Biological Agent Having an Aldehyde Functional Group

Figure 40:
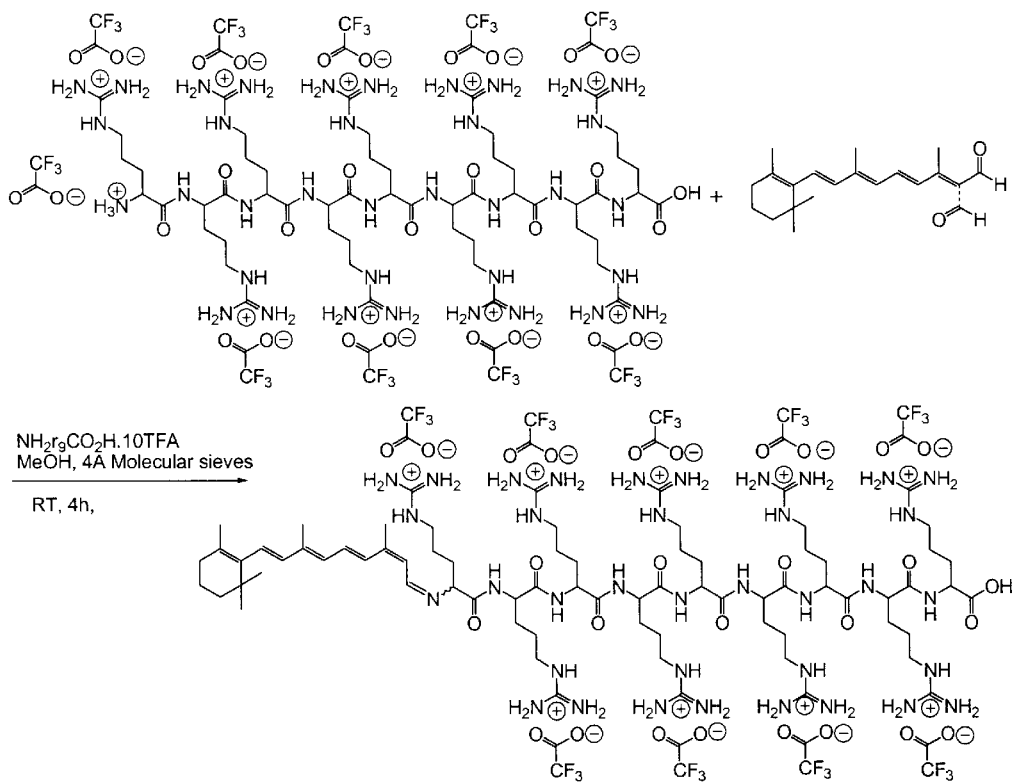
FIG. 40 illustrates the conjugate formed between a retinal and a r9 (shown without spacing amino acids).

This example illustrates the preparation of a conjugate between a nonamer of D-arginine ($H_2N$-$r_9$-$CO_2H$.10TFA) and either all trans-retinal or 13-cis-retinal. FIG. 40 provides a schematic presentation of the reactions. As seen in FIG. 40, condensation of either retinal with $H_2N$-$r_9$-$CO_2H$.10TFA in MeOH in the presence of 4 Å molecular seives at room temperature for four hours results in the formation of a Schiff base-type linkage between the retinal aldehyde and the amino terminal group. Purification of the conjugate can be accomplished by filtering the molecular sieves and removing methanol under reduced pressure.

b. Conjugation of Retinoic Acid to $r_7$-$CONH_2$

This example illustrates the preparation of a conjugate between retinoic acid and $r_7$-$CONH_2$ using the linking group

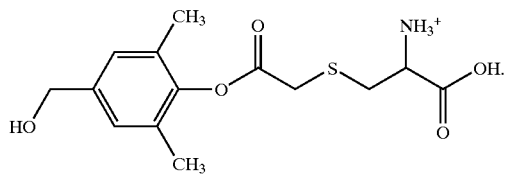

Figure 41:
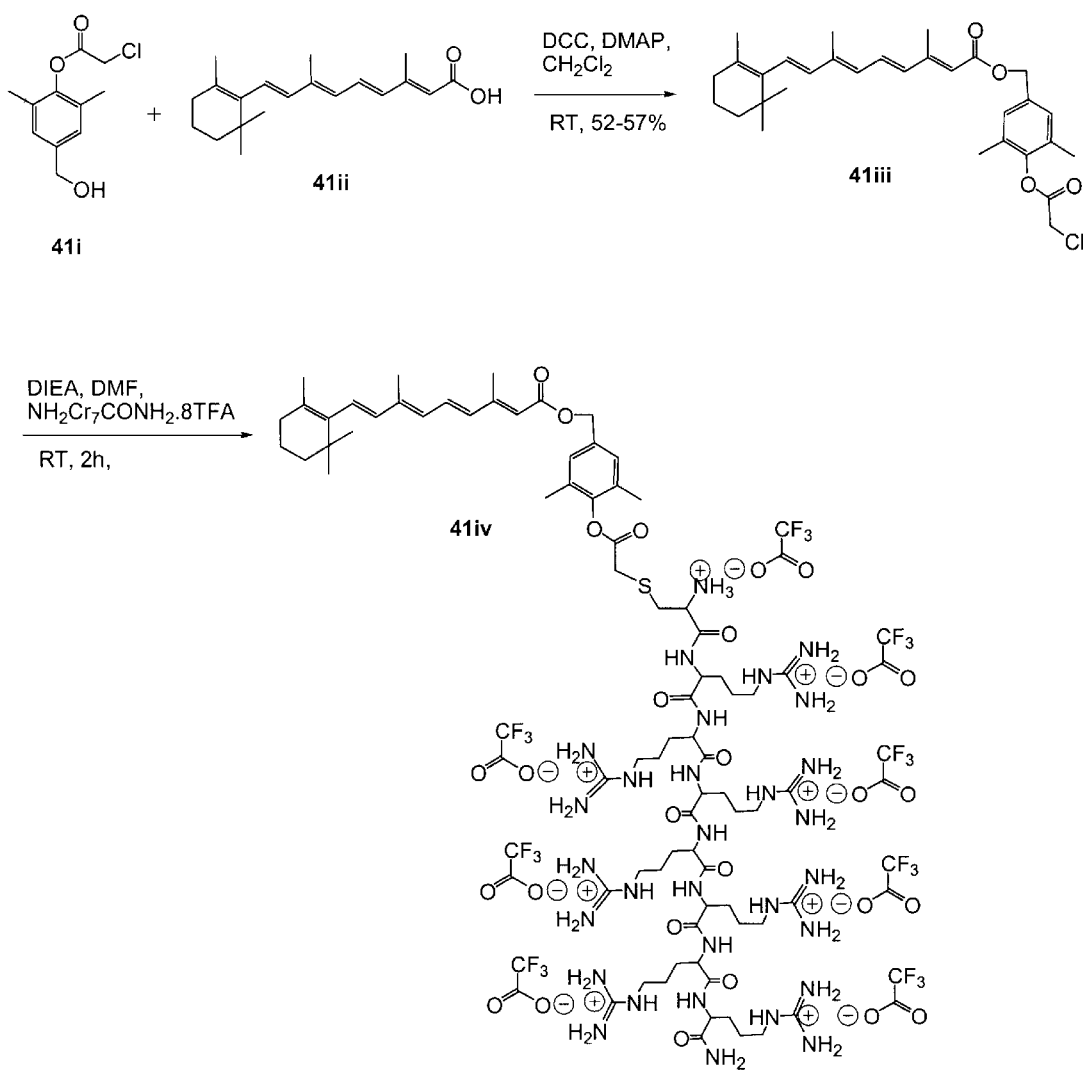
FIG. 41 illustrates the use of a cleavable linker in preparing a retinoic acid-r9 conjugate.

Here, preparation of the conjugate follows the scheme outlined in FIG. 41. In this scheme, retinoic acid (41ii) is first combined with the chloroacetate ester of 4-hydroxymethyl-2,6-dimethylphenol (41i) to provide the conjugate shown as 41iii. Combination of 41i with retinoic acid in methylene chloride in the presence of dicyclohexylcarbodiimide and a catalytic amount of 4-dimethylaminopyridine provided the retinoid derivative 41iii in 52–57% yield. Condensation of 41iii with $H_2N$Cys-$r_7CONH_2$.8TFA in the presence of diisopropylethylamine (DMF, room temperature, 2 h) provides the desired conjugated product 41iv.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

---

What is claimed is:

1. A method of targeting a compound to a gastrointestinal epithelium of an animal, the method comprising administering to the gastrointestinal epithelium a conjugate comprising the compound and a delivery-enhancing transporter, wherein:
 i. the delivery-enhancing transporter comprises fewer than 50 subunits and comprises at least 5 guanidino or amidino moieties; and
 ii. the conjugate has a structure selected from the group consisting of structures 3, 4, 5, and 6 as follows:

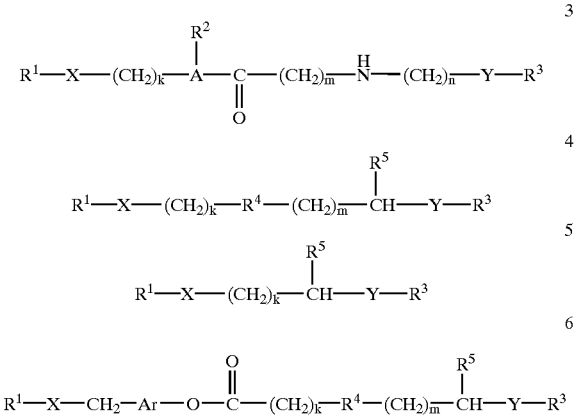

wherein:
 $R^1$ comprises the compound;
 X is a linkage formed between a functional group on the compound and a terminal functional group on the linking moiety;
 Y is a linkage formed from a functional group on the transport moiety and a functional group on the linking moiety;
 Ar is an aryl group having the attached radicals arranged in an ortho or para configuration, which aryl group can be substituted or unsubstituted;
 A is N or CH;
 $R^2$ is hydrogen, alkyl, aryl, acyl, or allyl;
 $R^3$ comprises the delivery-enhancing transporter;
 $R^4$ is S, O, $NR^6$ or $CR^7R^8$;
 $R^5$ is H, OH, SH or $NHR^6$;
 $R^6$ is hydrogen, alkyl, aryl, acyl or allyl;
 $R^7$ is hydrogen or an alkyl;
 $R^8$ is hydrogen or an alkyl;
 k and m are each independently selected from 1 and 2; and
 n is 1 to 10,
thereby increasing delivery of the conjugate into the gastrointestinal epithelium compared to delivery of the compound in the absence of the delivery-enhancing transporter.

2. The method of claim 1, wherein delivery of the conjugate into the gastrointestinal epithelium is increased at least two-fold compared to delivery of the compound in the absence of the delivery-enhancing transporter.

3. The method of claim 1, wherein delivery of the conjugate into the gastrointestinal epithelium is increased at least ten-fold compared to delivery of the compound in the absence of the delivery-enhancing transporter.

4. The method of claim 1, wherein the linker is a releasable linker.

5. The method of claim 1, wherein the subunits are amino acids.

6. The method of claim 1, wherein X is selected from the group consisting of —C(O)O—, —C(O)NH—, —OC(O)NH—, —S—S—, —C(S)O—, —C(S)NH—, —NHC(O)NR—, —$SO_2$NH—, —SONH—, phosphate, phosphonate, phosphinate, and $CR^7R^8$, wherein $R^7$ and $R^8$ are each independently selected from the group consisting of H and alkyl.

7. The method of claim 1, wherein the conjugate comprises structure 3, Y is NH, and $R^2$ is methyl, ethyl, propyl, butyl, allyl, benzyl or phenyl.

8. The method of claim 1, wherein the conjugate comprises structure 3, $R^2$ is benzyl; k, m, and n are each 1, and X is —OC(O)—.

9. The method of claim 1, wherein the conjugate comprises structure 4; $R^4$ is S; $R^5$ is $NHR^6$; and $R^6$ is hydrogen, methyl, allyl, butyl or phenyl.

10. The method of claim 1, wherein the conjugate comprises structure 4; $R^5$ is $NHR^6$; $R^6$ is hydrogen, methyl, allyl, butyl or phenyl; and k and m are each 1.

11. The method of claim 1, wherein the conjugate comprises structure 6, $R^4$ is S; $R^5$ is $NHR^6$; and $R^6$ is hydrogen, methyl, allyl, butyl or phenyl.

12. The method of claim 1, wherein the conjugate comprises at least two delivery-enhancing transporters.

13. The method of claim 1, wherein the conjugate is administered orally.

14. The method of claim 1, wherein the conjugate is administered as a suppository.

15. The method of claim 1, wherein the delivery-enhancing transporter comprises a non-peptide backbone.

16. The method of claim 1, wherein the delivery-enhancing transporter is not attached to an amino acid sequence to which the delivery enhancing transporter molecule is attached in a naturally occurring protein.

17. The method of claim 1, wherein the delivery-enhancing transporter comprises from 5 to 25 guanidino or amidino moieties.

18. The method of claim 17, wherein the delivery-enhancing transporter comprises between 7 and 15 guanidino moieties.

19. The method of claim 17, wherein the delivery-enhancing transporter comprises at least 6 contiguous guanidino and/or amidino moieties.

20. The method of claim 1, wherein the delivery-enhancing transporter consists essentially of 5 to 50 amino acids, at least 50 percent of which amino acids are arginines or analogs thereof.

21. The method of claim 20, wherein the delivery-enhancing transporter comprises 5 to 25 arginine residues or analogs thereof.

22. The method of claim 21, wherein at least one arginine is a D-arginine.

23. The method of claim 22, wherein all of the arginines are D-arginines.

24. The method of claim 20, wherein at least 70 percent of the amino acids that comprise the delivery-enhancing transporter are arginines or arginine analogs.

25. The method of claim 20, wherein the delivery-enhancing transporter is seven contiguous D-arginines.

26. The method of claim 1, wherein the compound is a therapeutic for the disease selected from the group consisting of inflammatory bowel disease, colon cancer, ulcerative colitis, gastrointestinal ulcers, constipation and imbalance of salt and water absorption.

27. The method of claim 1, wherein the compound is selected from the group consisting of immunosuppressiVes, ascomycins, corticosteroids, laxatives, antibiotics and antineoplastic agents.

28. The method of claim 1, wherein the compound is targeted to the iliem and/or colon.

29. A method for enhancing delivery of a compound into and across one or more layers of an animal ocular epithelial tissue, the method comprising:
  administering to the ocular epithelial tissue a conjugate comprising the compound and a delivery-enhancing transporter,
  wherein:
    i. the compound is attached to the delivery-enhancing transporter through a linker, and
    ii. the delivery-enhancing transporter comprises fewer than 50 subunits and comprises at least 5 guanidino or amidino moieties, thereby increasing delivery of the conjugate into and across the ocular epithelial tissue compared to delivery of the compound in the absence of the delivery-enhancing transporter.

30. The method of claim 29, wherein delivery of the conjugate into the ocular epithelial tissue is increased at least two-fold compared to delivery of the compound in the absence of the delivery-enhancing transporter.

31. The method of claim 29, wherein delivery of the conjugate into the ocular epithelial tissue is increased at least ten-fold compared to delivery of the compound in the absence of the delivery-enhancing transporter.

32. The method of claim 29, wherein the linker is a releasable linker.

33. The method of claim 29, wherein the subunits are amino acids.

34. The method of claim 4 wherein the conjugate has a structure selected from the group consisting of structures 3, 4, and 5, as follows:

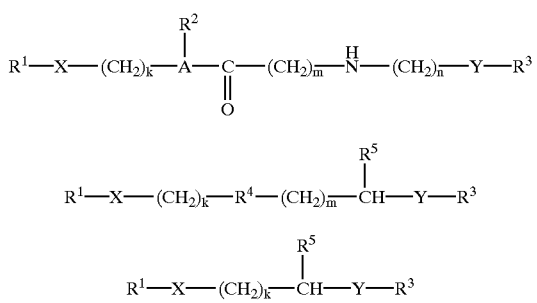

wherein:
  $R^1$ comprises the compound;
  X is a linkage formed between a functional group on the compound and a terminal functional group on the linking moiety;
  Y is a linkage formed from a functional group on the transport moiety and a functional group on the linking moiety;
  A is N or CH;
  $R^2$ is hydrogen, alkyl, aryl, acyl, or allyl;
  $R^3$ comprises the delivery-enhancing transporter;
  $R^4$ is S, O, $NR^6$ or $CR^7R^8$;
  $R^5$ is H, OH, SH or $NHR^6$;
  $R^6$ is hydrogen, alkyl, aryl, acyl or allyl;
  $R^7$ and $R^8$ are independently selected from hydrogen or alkyl;
  k and m are each independently selected from 1 and 2; and
  n is 1 to 10.

35. The method of claim 34, wherein X is selected from the group consisting of —C(O)O—, —C(O)NH—, —OC(O)NH—, —S—S—, —C(S)O—, —C(S)NH—, —NHC(O)NH—, —SO$_2$NH—, —SONH—, phosphate, phosphonate, phosphinate, and $CR^7R^8$, wherein $R^7$ and $R^8$ are each independently selected from the group consisting of H and alkyl.

36. The method of claim 34, wherein the conjugate comprises structure 3, Y is NH, and $R^2$ is methyl, ethyl, propyl, butyl, allyl, benzyl or phenyl.

37. The method of claim 34, wherein $R^2$ is benzyl; k, m, and n are each 1, and X is —OC(O)—.

38. The method of claim 34, wherein the conjugate comprises structure 4; $R^4$ is S; $R^5$ is $NHR^6$; and $R^6$ is hydrogen, methyl, allyl, butyl or phenyl.

39. The method of claim 34, wherein the conjugate comprises structure 4; $R^5$ is $NHR^6$; $R^6$ is hydrogen, methyl, allyl, butyl or phenyl; and k and m are each 1.

40. The method of claim 29, wherein the conjugate comprises structure 6 as follows:

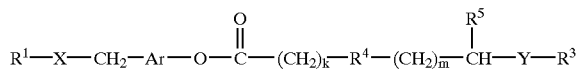

wherein:
  $R^1$ the compound;
  X is a linkage formed between a functional group on the compound and a terminal functional group on the linking moiety;
  Y is a linkage formed from a functional group on the transport moiety and a functional group on the linking moiety;
  Ar is an aryl group having the attached radicals arranged in an ortho or para configuration, which aryl group can be substituted or unsubstituted;
  $R^3$ comprises the delivery-enhancing transporter;
  $R^4$ is S, O, $NR^6$ or $CR^7R^8$;
  $R^5$ is H, OH, SH or $NHR^6$;
  $R^6$ is hydrogen, alkyl, aryl, arylalkyl, acyl or allyl;
  $R^7$ and $R^8$ are independently selected from hydrogen or alkyl; and
  k and m are each independently selected from 1 and 2.

41. The method of claim 40, wherein X is selected from the group consisting of —C(O)O—, —C(O)NH—, —OC(O)NH—, —S—S—, —C(S)O—, —C(S)NH—, —NHC(O)NH—, —SO$_2$NH—, —SONH—, phosphate, phosphonate, phosphinate, and $CR^7R^8$, wherein $R^7$ and $R^8$ are each independently selected from the group consisting of H and alkyl.

42. The method of claim 40, wherein $R^4$ is S; $R^5$ is $NHR^6$; and $R^6$ is hydrogen, methyl, allyl, butyl or phenyl.

43. The method of claim 29, wherein the conjugate comprises at least two delivery-enhancing transporters.

44. The method of claim 29, wherein the conjugate is administered as an eye drop.

45. The method of claim 29, wherein the conjugate is administered as an injection.

46. The method of claim 29, wherein the delivery-enhancing transporter comprises a non-peptide backbone.

47. The method of claim 29, wherein the delivery-enhancing transporter is not attached to an amino acid sequence to which the delivery enhancing transporter molecule is attached in a naturally occurring protein.

48. The method of claim 29, wherein the delivery-enhancing transporter comprises from 5 to 25 guanidino or amidino moieties.

49. The method of claim 48, wherein the delivery-enhancing transporter comprises between 7 and 15 guanidino moieties.

50. The method of claim 48, wherein the delivery-enhancing transporter comprises at least 6 contiguous guanidino and/or amidino moieties.

51. The method of claim 29, wherein the delivery-enhancing transporter consists essentially of 5 to 50 amino acids, at least 50 percent of which amino acids are arginines or analogs thereof.

52. The method of claim 51, wherein the delivery-enhancing transporter comprises 5 to 25 arginine residues or analogs thereof.

53. The method of claim wherein at least one arginine is a D-arginine.

54. The method of claim 53, wherein all of the arginines are D-arginines.

55. The method of claim 51, wherein at least 70 percent of the amino acids that comprise the delivery-enhancing transporter are arginines or arginine analogs.

56. The method of claim 51, wherein the delivery-enhancing transporter is seven contiguous D-arginines.

57. The method of claim 29, wherein the compound is a therapeutic for the disease selected from the group consisting of conjunctivitis, bacterial infections, viral infections, dry eye, and glaucoma.

58. The method of claim 29, wherein the compound is selected from the group consisting of antibacterial compounds, antiviral compounds, cyclosporin, ascomycins, and corticosteroids.

59. A method of targeting a compound to a gastrointestinal epithelium of an animal, the method comprising administering to the gastrointestinal epithelium a conjugate comprising the compound and a delivery-enhancing transporter, wherein:
   i. the compound is attached to the delivery-enhancing transporter through a linker;
   ii. the compound is a therapeutic for the disease selected from the group consisting of inflammatory bowel disease, colon cancer, ulcerative colitis, gastrointestinal ulcers, constipation and imbalance of salt and water absorption; and
   ii. the delivery-enhancing transporter comprises fewer than 50 subunits and comprises at least 5 guanidino or amidino moieties, thereby increasing delivery of the conjugate into the gastrointestinal epithelium compared to delivery of the compound in the absence of the delivery-enhancing transporter.

60. The method of claim 59, wherein the compound is therapeutic for inflammatory bowel disease.

61. The method of claim 59, wherein the compound is therapeutic for colon cancer.

62. The method of claim 59, wherein the compound is therapeutic for ulcerative colitis.

63. The method of claim 59, wherein the compound is therapeutic for gastrointestinal ulcers.

64. The method of claim 59, wherein the compound is therapeutic for constipation.

65. The method of claim 59, wherein the compound is therapeutic for an imbalance of salt and water absorption.

66. A method for enhancing delivery of a compound into and across one or more layers of an animal epithelial tissue, the method comprising buccally administering a conjugate comprising the compound and a delivery-enhancing transporter, wherein:
   i. the compound is attached to the delivery-enhancing transporter through a linker; and
   ii. the delivery-enhancing transporter comprises fewer than 50 subunits and comprises at least 5 guanidino or amidino moieties, thereby increasing delivery of the conjugate into and across one or more layers of the animal epithelial tissue compared to delivery of the compound in the absence of the delivery-enhancing transporter.

67. The method of claim 66, wherein the linker is a releasable linker.

68. The method of claim 66, wherein the subunits are amino acids.

69. The method of claim 66, wherein the conjugate has a structure selected from the group consisting of structures 3, 4, 5 and 6, as follows:

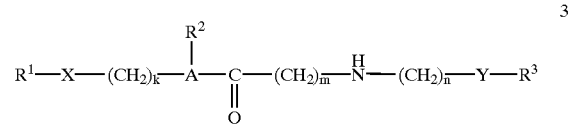

3

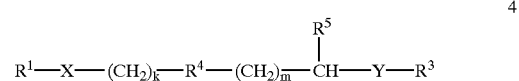

4

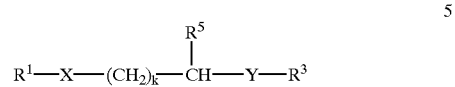

5

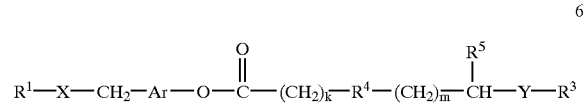

6 wherein:

$R^1$ comprises the compound;

X is a linkage formed between a functional group on the compound and a terminal functional group on the linking moiety;

Y is a linkage formed from a functional group on the transport moiety and a functional group on the linking moiety;

Ar is an aryl group having the attached radicals arranged in an ortho or para configuration, which aryl group can be substituted or unsubstituted;

A is N or CH;

$R^2$ is hydrogen, alkyl, aryl, acyl, or allyl;

$R^3$ comprises the delivery-enhancing transporter;

$R^4$ is S, O, $NR^6$ or $CR^7R^8$;

$R^5$ is H, OH, SH or $NHR^6$;

R⁶ is hydrogen, alkyl, aryl, acyl or allyl;

R⁷ is hydrogen or an alkyl;

R⁸ is hydrogen or an alkyl;

k and m are each independently selected from 1 and 2; and n is 1 to 10.

70. The method of claim 69, wherein X is selected from the group consisting of —C(O)O—, —C(O)NH—, —OC(O)NH—, —S—S—, —C(S)O—, —C(S)NH—, —NHC(O)NH—, —SO$_2$NH—, —SONH—, phosphate, phosphonate, phosphinate, and CR$^7$R$^8$, wherein R$^7$ and R$^8$ are each independently selected from the group consisting of H and alkyl.

71. The method of claim 69, wherein the conjugate comprises structure 3, Y is NH, and R$^2$ is methyl, ethyl, propyl, butyl, allyl, benzyl or phenyl.

72. The method of claim 69, wherein R$^2$ is benzyl; k, m, and n are each 1, and X is —OC(O)—.

73. The method of claim 69, wherein the conjugate comprises structure 4; R$^4$ is S; R$^5$ is NHR6; and R$^6$ is hydrogen, methyl, allyl, butyl or phenyl.

74. The method of claim 69, wherein the conjugate comprises structure 4; R$^5$ is NHR$^6$; R$^6$ is hydrogen, methyl, allyl, butyl or phenyl; and k and m are each 1.

75. The method of claim 69, wherein the conjugate comprises structure 6, R$^4$ is S; R$^5$ is NHR$^6$; and R$^6$ is hydrogen, methyl, allyl, butyl or phenyl.

76. The method of claim 66, wherein the conjugate comprises at least two delivery-enhancing transporters.

77. The method of claim 69, wherein the delivery-enhancing transporter comprises a non-peptide backbone.

78. The method of claim 66, wherein the delivery-enhancing transporter is not attached to an amino acid sequence to which the delivery enhancing transporter molecule is attached in a naturally occurring protein.

79. The method of claim 66, wherein the delivery-enhancing transporter comprises from 5 to 25 guanidino or amidino moieties.

80. The method of claim 66, wherein the delivery-enhancing transporter comprises between 7 and 15 guanidino moieties.

81. The method of claim 66, wherein the delivery-enhancing transporter comprises at least 6 contiguous guanidino and/or amidino moieties.

82. The method of claim 66, wherein the delivery-enhancing transporter consists essentially of 5 to 50 amino acids, at least 50 percent of which amino acids are arginines or analogs thereof.

83. The method of claim 66, wherein the delivery-enhancing transporter comprises 5 to 25 arginine residues or analogs thereof.

84. The method of claim 83, wherein at least one arginine is a D-arginine.

85. The method of claim 84, wherein all of the arginines are D-arginines.

86. The method of claim 82, wherein at least 70 percent of the amino acids that comprise the delivery-enhancing transporter are arginines or arginine analogs.

87. The method of claim 66, wherein the delivery-enhancing transporter is seven contiguous D-arginines.

88. The method of claim 29, wherein the conjugate is transported into an ocular tissue selected from the group consisting of cornea, iris, lens, vitreus, vitreus humor, aqueous humor, sclera, and optic nerve.

* * * * *